United States Patent
Reicher et al.

(10) Patent No.: US 10,929,508 B2
(45) Date of Patent: Feb. 23, 2021

(54) DATABASE SYSTEMS AND INTERACTIVE USER INTERFACES FOR DYNAMIC INTERACTION WITH, AND INDICATIONS OF, DIGITAL MEDICAL IMAGE DATA

(71) Applicant: MERGE HEALTHCARE SOLUTIONS INC., Hartland, WI (US)

(72) Inventors: Murray A. Reicher, Rancho Santa Fe, CA (US); Evan K. Fram, Paradise Valley, AZ (US)

(73) Assignee: MERGE HEALTHCARE SOLUTIONS INC., Hartland, WI (US)

( * ) Notice: Subject to any disclaimer, the term of this patent is extended or adjusted under 35 U.S.C. 154(b) by 988 days.

(21) Appl. No.: 15/140,348

(22) Filed: Apr. 27, 2016

(65) Prior Publication Data

US 2017/0039322 A1    Feb. 9, 2017

Related U.S. Application Data

(60) Provisional application No. 62/155,362, filed on Apr. 30, 2015, provisional application No. 62/171,866, filed on Jun. 5, 2015.

(51) Int. Cl.
*G06F 16/245* (2019.01)
*G06F 16/583* (2019.01)
(Continued)

(52) U.S. Cl.
CPC ........ *G06F 19/321* (2013.01); *G06F 3/04845* (2013.01); *G06F 3/04847* (2013.01);
(Continued)

(58) Field of Classification Search
CPC .. G06F 19/321; G06F 3/0482; G06F 3/04842; G06F 3/04845; G06F 17/30274;
(Continued)

(56) References Cited

U.S. PATENT DOCUMENTS

| 4,672,683 A | 6/1987 | Matsueda |
| 5,123,056 A | 6/1992 | Wilson |
| (Continued) | | |

FOREIGN PATENT DOCUMENTS

WO    WO 2007/131157    11/2007

OTHER PUBLICATIONS

US 7,801,341 B2, 09/2010, Fram et al. (withdrawn)
(Continued)

*Primary Examiner* — Robert W Beausoliel, Jr.
*Assistant Examiner* — Pedro J Santos
(74) *Attorney, Agent, or Firm* — Michael Best & Friedrich LLP

(57) ABSTRACT

Database systems and techniques are disclosed for accessing data stores of digital medical images, processing the digital images, and displaying the digital images to efficiently provide information in an interactive user interface. The disclosure may advantageously provide efficient and rapid dynamic interaction with digital images accessed from one or more databases to enable user detection of differences between related digital images. Interactive user interfaces may be dynamically updated to provide rapid comparison of digital images. Further, digital images from multiple data sources may be automatically sorted by the system according to attributes associated with the images and rules and/or preferences of the user. In an embodiment the user may select a digital image from a first data source, and the system automatically determines and displays one or more comparison images from other image data sources. Images may additionally be automatically registered and/or matched to enable more efficient comparison and evaluation.

23 Claims, 21 Drawing Sheets

(51) Int. Cl.
*G06F 19/00* (2018.01)
*G06F 16/2457* (2019.01)
*G06F 3/0484* (2013.01)

(52) U.S. Cl.
CPC ...... *G06F 16/245* (2019.01); *G06F 16/24573* (2019.01); *G06F 16/583* (2019.01)

(58) Field of Classification Search
CPC ......... G06F 17/30424; G06F 17/30525; G06F 16/24573; G06F 16/245; G06F 16/583; G16H 30/00; G16H 30/20; G16H 30/40
USPC ........................................ 707/728, 756, 758
See application file for complete search history.

(56) References Cited

U.S. PATENT DOCUMENTS

| | | |
|---|---|---|
| 5,172,419 A | 12/1992 | Manian |
| 5,179,651 A | 1/1993 | Taaffe et al. |
| 5,431,161 A | 7/1995 | Ryals et al. |
| 5,452,416 A | 9/1995 | Hilton et al. |
| 5,515,375 A | 5/1996 | DeClerck |
| 5,542,003 A | 7/1996 | Wofford |
| 5,734,915 A | 3/1998 | Roewer |
| 5,740,267 A | 4/1998 | Echerer et al. |
| 5,779,634 A | 7/1998 | Ema et al. |
| 5,807,256 A | 9/1998 | Taguchi |
| 5,835,030 A | 11/1998 | Tsutsui et al. |
| 5,852,646 A | 12/1998 | Klotz et al. |
| 5,857,030 A | 1/1999 | Gaborski |
| 5,867,322 A | 2/1999 | Morton |
| 5,926,568 A | 7/1999 | Chaney et al. |
| 5,954,650 A | 9/1999 | Saito et al. |
| 5,976,088 A | 11/1999 | Urbano et al. |
| 5,986,662 A | 11/1999 | Argiro et al. |
| 5,987,345 A | 11/1999 | Engelmann et al. |
| 5,995,644 A | 11/1999 | Lai et al. |
| 6,008,813 A | 12/1999 | Lauer et al. |
| 6,115,486 A | 9/2000 | Cantoni |
| 6,128,002 A | 10/2000 | Leiper |
| 6,130,671 A | 10/2000 | Agiro |
| 6,151,581 A | 11/2000 | Kraftson et al. |
| 6,175,643 B1 | 1/2001 | Lai et al. |
| 6,177,937 B1 | 1/2001 | Stockham et al. |
| 6,185,320 B1 | 2/2001 | Bick et al. |
| 6,211,795 B1 | 4/2001 | Izuta |
| 6,211,884 B1 | 4/2001 | Knittel et al. |
| 6,219,059 B1 | 4/2001 | Argiro |
| 6,219,061 B1 | 4/2001 | Lauer et al. |
| 6,243,095 B1 | 6/2001 | Shile et al. |
| 6,243,098 B1 | 6/2001 | Lauer et al. |
| 6,262,740 B1 | 7/2001 | Lauer et al. |
| 6,266,733 B1 | 7/2001 | Knittel et al. |
| 6,269,379 B1 | 7/2001 | Hiyama et al. |
| 6,297,799 B1 | 10/2001 | Knittel et al. |
| 6,304,667 B1 | 10/2001 | Reitano |
| 6,310,620 B1 | 10/2001 | Lauer et al. |
| 6,313,841 B1 | 11/2001 | Ogata et al. |
| 6,342,885 B1 | 1/2002 | Knittel et al. |
| 6,347,329 B1 | 2/2002 | Evans |
| 6,351,547 B1 | 2/2002 | Johnson et al. |
| 6,356,265 B1 | 3/2002 | Knittel et al. |
| 6,369,816 B1 | 4/2002 | Knittel et al. |
| 6,383,135 B1 | 5/2002 | Chikovani et al. |
| 6,388,687 B1 | 5/2002 | Brackett et al. |
| 6,404,429 B1 | 6/2002 | Knittel |
| 6,407,737 B1 | 6/2002 | Zhao et al. |
| 6,411,296 B1 | 6/2002 | Knittel et al. |
| 6,421,057 B1 | 7/2002 | Lauer et al. |
| 6,424,346 B1 | 7/2002 | Correll et al. |
| 6,424,996 B1 | 7/2002 | Killcommons et al. |
| 6,426,749 B1 | 7/2002 | Knittel et al. |
| 6,427,022 B1 | 7/2002 | Craine et al. |
| 6,438,533 B1 | 8/2002 | Spackman et al. |
| 6,463,169 B1 | 10/2002 | Ino et al. |
| 6,476,810 B1 | 11/2002 | Simha et al. |
| 6,512,517 B1 | 1/2003 | Knittel et al. |
| 6,532,299 B1 | 3/2003 | Sachdeva et al. |
| 6,532,311 B1 | 3/2003 | Pritt |
| 6,556,695 B1 | 4/2003 | Packer et al. |
| 6,556,724 B1 | 4/2003 | Chang et al. |
| 6,563,950 B1 | 5/2003 | Wiskott et al. |
| 6,574,629 B1 | 6/2003 | Cooke et al. |
| 6,577,753 B2 | 6/2003 | Ogawa |
| 6,603,494 B1 | 8/2003 | Banks et al. |
| 6,606,171 B1 | 8/2003 | Renk et al. |
| 6,614,447 B1 | 9/2003 | Bhatia et al. |
| 6,618,060 B1 | 9/2003 | Brackett |
| 6,621,918 B1 | 9/2003 | Hu et al. |
| 6,630,937 B2 | 10/2003 | Kallergi et al. |
| 6,650,766 B1 | 11/2003 | Rogers |
| 6,654,012 B1 | 11/2003 | Lauer et al. |
| 6,678,764 B2 | 1/2004 | Parvelescu et al. |
| 6,680,735 B1 | 1/2004 | Seiler et al. |
| 6,683,933 B2 | 1/2004 | Saito et al. |
| 6,697,067 B1 | 2/2004 | Callahan et al. |
| 6,697,506 B1 | 2/2004 | Oian et al. |
| 6,734,880 B2 | 5/2004 | Chang et al. |
| 6,760,755 B1 | 7/2004 | Brackett |
| 6,775,402 B2 | 8/2004 | Bacus et al. |
| 6,778,689 B1 | 8/2004 | Aksit et al. |
| 6,785,410 B2 | 8/2004 | Vining et al. |
| 6,820,093 B2 | 11/2004 | de la Huerga |
| 6,820,100 B2 | 11/2004 | Funahashi |
| 6,826,297 B2 | 11/2004 | Saito et al. |
| 6,829,377 B2 | 12/2004 | Milioto |
| 6,864,794 B2 | 3/2005 | Betz |
| 6,886,133 B2 | 4/2005 | Bailey et al. |
| 6,891,920 B1 | 5/2005 | Minyard et al. |
| 6,894,707 B2 | 5/2005 | Nemoto |
| 6,909,436 B1 | 6/2005 | Pianykh et al. |
| 6,909,795 B2 | 6/2005 | Tecotzky et al. |
| 6,917,696 B2 | 7/2005 | Soenksen |
| 6,988,075 B1 | 1/2006 | Hacker |
| 6,996,205 B2 | 2/2006 | Capolunghi et al. |
| 7,016,952 B2 | 3/2006 | Mullen et al. |
| 7,022,073 B2 | 4/2006 | Fan et al. |
| 7,027,633 B2 | 4/2006 | Foran et al. |
| 7,031,504 B1 | 4/2006 | Argiro et al. |
| 7,031,846 B2 | 4/2006 | Kaushikkar et al. |
| 7,039,723 B2 | 5/2006 | Hu et al. |
| 7,043,474 B2 | 5/2006 | Mojsilovic |
| 7,050,620 B2 | 5/2006 | Heckman |
| 7,054,473 B1 | 5/2006 | Roehrig et al. |
| 7,058,901 B1 | 6/2006 | Hafey et al. |
| 7,092,572 B2 | 8/2006 | Huang et al. |
| 7,103,205 B2 | 9/2006 | Wang et al. |
| 7,106,479 B2 | 9/2006 | Roy et al. |
| 7,110,616 B2 | 9/2006 | Ditt et al. |
| 7,113,186 B2 | 9/2006 | Kim et al. |
| 7,123,684 B2 | 10/2006 | Jing et al. |
| 7,136,064 B2 | 11/2006 | Zuiderveld |
| 7,139,416 B2 | 11/2006 | Vuylsteke |
| 7,149,334 B2 | 12/2006 | Dehmeshki |
| 7,155,043 B2 | 12/2006 | Daw |
| 7,162,623 B2 | 1/2007 | Yngvesson |
| 7,170,532 B2 | 1/2007 | Sako |
| 7,174,054 B2 | 2/2007 | Manber et al. |
| 7,209,149 B2 | 4/2007 | Jogo |
| 7,209,578 B2 | 4/2007 | Saito et al. |
| 7,212,661 B2 | 5/2007 | Samara et al. |
| 7,218,763 B2 | 5/2007 | Belykh et al. |
| 7,224,852 B2 | 5/2007 | Lipton et al. |
| 7,236,558 B2 | 6/2007 | Saito et al. |
| 7,260,249 B2 | 8/2007 | Smith |
| 7,263,710 B1 | 8/2007 | Hummel et al. |
| 7,272,610 B2 | 9/2007 | Torres |
| 7,346,199 B2 | 3/2008 | Pfaff |
| 7,366,992 B2 | 4/2008 | Thomas, III |
| 7,379,578 B2 | 5/2008 | Soussaline et al. |
| 7,412,111 B2 | 8/2008 | Battle et al. |
| 7,450,747 B2 | 11/2008 | Jabri et al. |
| 7,492,970 B2 | 2/2009 | Saito et al. |
| 7,505,782 B2 | 3/2009 | Chu |

(56) References Cited

U.S. PATENT DOCUMENTS

| | | |
|---|---|---|
| 7,516,417 B2 | 4/2009 | Amador et al. |
| 7,523,505 B2 | 4/2009 | Menschik et al. |
| 7,525,554 B2 | 4/2009 | Morita et al. |
| 7,526,114 B2 | 4/2009 | Seul et al. |
| 7,526,132 B2 | 4/2009 | Koenig |
| 7,545,965 B2 | 6/2009 | Suzuki et al. |
| 7,574,029 B2 | 8/2009 | Peterson et al. |
| 7,583,861 B2 | 9/2009 | Hanna et al. |
| 7,590,272 B2 | 9/2009 | Brejl et al. |
| 7,599,534 B2 | 10/2009 | Krishnan |
| 7,613,335 B2 | 11/2009 | McLennan et al. |
| 7,634,121 B2 | 12/2009 | Novatzky et al. |
| 7,636,413 B2 | 12/2009 | Toth |
| 7,639,879 B2 | 12/2009 | Goto et al. |
| 7,656,543 B2 | 2/2010 | Atkins |
| 7,660,413 B2 | 2/2010 | Partovi et al. |
| 7,660,481 B2 | 2/2010 | Schaap et al. |
| 7,660,488 B2 | 2/2010 | Reicher et al. |
| 7,668,352 B2 | 2/2010 | Tecotzky et al. |
| 7,683,909 B2 | 3/2010 | Takekoshi |
| 7,698,152 B2 | 4/2010 | Reid |
| 7,716,277 B2 | 5/2010 | Yamatake |
| 7,787,672 B2 | 8/2010 | Reicher et al. |
| 7,834,891 B2 | 11/2010 | Yarger et al. |
| 7,835,560 B2 | 11/2010 | Vining et al. |
| 7,885,440 B2 | 2/2011 | Fram et al. |
| 7,885,828 B2 | 2/2011 | Glaser-Seidnitzer et al. |
| 7,899,514 B1 | 3/2011 | Kirkland |
| 7,920,152 B2 | 4/2011 | Fram et al. |
| 7,941,462 B2 | 5/2011 | Akinyemi et al. |
| 7,953,614 B1 | 5/2011 | Reicher et al. |
| 7,970,188 B2 | 6/2011 | Mahesh et al. |
| 7,970,625 B2 | 6/2011 | Reicher et al. |
| 7,991,210 B2 | 8/2011 | Peterson et al. |
| 7,992,100 B2 | 8/2011 | Lundstrom et al. |
| 7,995,821 B2 | 8/2011 | Nakamura |
| 8,019,138 B2 | 9/2011 | Reicher et al. |
| 8,046,044 B2 | 10/2011 | Stazzone et al. |
| 8,050,938 B1 | 11/2011 | Green, Jr. et al. |
| 8,065,166 B2 | 11/2011 | Maresh et al. |
| 8,073,225 B2 | 12/2011 | Hagen et al. |
| 8,094,901 B1 | 1/2012 | Reicher et al. |
| 8,150,708 B2 | 4/2012 | Kotula et al. |
| 8,214,756 B2 | 7/2012 | Salazar-Ferrer et al. |
| 8,217,966 B2 | 7/2012 | Fram et al. |
| 8,244,014 B2 | 8/2012 | Reicher et al. |
| 8,249,687 B2 | 8/2012 | Peterson et al. |
| 8,262,572 B2 | 9/2012 | Chono |
| 8,292,811 B2 | 10/2012 | Relkuntwar et al. |
| 8,298,147 B2 | 10/2012 | Huennekens et al. |
| 8,370,293 B2 | 2/2013 | (Wase et al. |
| 8,379,051 B2 | 2/2013 | Brown |
| 8,380,533 B2 | 2/2013 | Reicher et al. |
| 8,391,643 B2 | 3/2013 | Melbourne et al. |
| 8,406,491 B2 | 3/2013 | Gee et al. |
| 8,452,063 B2 | 5/2013 | Wojton et al. |
| 8,457,990 B1 | 6/2013 | Reicher et al. |
| 8,520,978 B2 | 8/2013 | Jakobovits |
| 8,554,576 B1 | 10/2013 | Reicher et al. |
| 8,560,050 B2 | 10/2013 | Martin et al. |
| 8,610,746 B2 | 12/2013 | Fram et al. |
| 8,626,527 B1 | 1/2014 | Reicher et al. |
| 8,693,757 B2 | 4/2014 | Gundel |
| 8,712,120 B1 | 4/2014 | Reicher et al. |
| 8,731,259 B2 | 5/2014 | Reicher et al. |
| 8,751,268 B1 | 6/2014 | Reicher et al. |
| 8,771,189 B2 | 7/2014 | Lonasec et al. |
| 8,797,350 B2 | 8/2014 | Fram |
| 8,879,807 B2 | 11/2014 | Fram et al. |
| 8,913,808 B2 | 12/2014 | Reicher et al. |
| 8,954,884 B1 * | 2/2015 | Barger .................. G06F 3/0485 715/792 |
| 8,976,190 B1 | 3/2015 | Westerhoff et al. |
| 9,042,617 B1 | 5/2015 | Reicher et al. |
| 9,075,899 B1 | 7/2015 | Reicher |
| 9,092,551 B1 | 7/2015 | Reicher |
| 9,092,727 B1 | 7/2015 | Reicher |
| 9,324,188 B1 | 4/2016 | Fram et al. |
| 9,386,084 B1 | 7/2016 | Reicher et al. |
| 9,471,210 B1 | 10/2016 | Fram et al. |
| 9,495,604 B1 | 11/2016 | Fram |
| 9,501,617 B1 | 11/2016 | Reicher et al. |
| 9,501,627 B2 | 11/2016 | Reicher et al. |
| 9,501,863 B1 | 11/2016 | Fram et al. |
| 9,536,324 B1 | 1/2017 | Fram |
| 9,542,082 B1 | 1/2017 | Reicher et al. |
| 9,672,477 B1 | 6/2017 | Reicher et al. |
| 9,684,762 B2 | 6/2017 | Reicher et al. |
| 9,727,938 B1 | 8/2017 | Reicher et al. |
| 9,734,576 B2 | 8/2017 | Fram et al. |
| 9,754,074 B1 | 9/2017 | Reicher et al. |
| 9,836,202 B1 | 12/2017 | Reicher et al. |
| 9,892,341 B2 | 2/2018 | Reicher et al. |
| 9,934,568 B2 | 4/2018 | Reicher et al. |
| 10,096,111 B2 | 10/2018 | Fram et al. |
| 10,157,686 B1 | 12/2018 | Reicher et al. |
| 10,387,612 B2 | 8/2019 | Wu et al. |
| 10,437,444 B2 | 10/2019 | Reicher et al. |
| 10,438,352 B2 | 10/2019 | Fram et al. |
| 10,540,763 B2 | 1/2020 | Wu et al. |
| 10,579,903 B1 | 3/2020 | Reicher |
| 10,592,688 B2 | 3/2020 | Reicher et al. |
| 10,607,341 B2 | 3/2020 | Reicher et al. |
| 10,614,615 B2 | 4/2020 | Fram et al. |
| 10,665,342 B2 | 5/2020 | Fram |
| 10,672,512 B2 | 6/2020 | Fram |
| 10,782,862 B2 | 9/2020 | Reicher et al. |
| 10,790,057 B2 | 9/2020 | Reicher et al. |
| 2001/0016822 A1 | 8/2001 | Bessette |
| 2001/0041991 A1 | 11/2001 | Segal et al. |
| 2001/0042124 A1 | 11/2001 | Barron |
| 2002/0016718 A1 | 2/2002 | Rothschild et al. |
| 2002/0021828 A1 | 2/2002 | Papier et al. |
| 2002/0039084 A1 | 4/2002 | Yamaguchi |
| 2002/0044696 A1 | 4/2002 | Sirohey et al. |
| 2002/0054038 A1 | 5/2002 | Nemoto |
| 2002/0070970 A1 | 6/2002 | Wood et al. |
| 2002/0073429 A1 | 6/2002 | Beane et al. |
| 2002/0090118 A1 | 7/2002 | Olschewski |
| 2002/0090119 A1 | 7/2002 | Saito et al. |
| 2002/0090124 A1 | 7/2002 | Soubelet et al. |
| 2002/0091659 A1 | 7/2002 | Beaulieu et al. |
| 2002/0099273 A1 | 7/2002 | Bocionek et al. |
| 2002/0103673 A1 | 8/2002 | Atwood |
| 2002/0103827 A1 | 8/2002 | Sesek |
| 2002/0106119 A1 | 8/2002 | Foran et al. |
| 2002/0106373 A1 | 8/2002 | Hillman et al. |
| 2002/0110285 A1 | 8/2002 | Wang et al. |
| 2002/0144697 A1 | 10/2002 | Betz |
| 2002/0145941 A1 | 10/2002 | Poland et al. |
| 2002/0172408 A1 | 11/2002 | Saito et al. |
| 2002/0172409 A1 | 11/2002 | Saito et al. |
| 2002/0180883 A1 | 12/2002 | Tomizawa et al. |
| 2002/0186820 A1 | 12/2002 | Saito et al. |
| 2002/0188637 A1 | 12/2002 | Bailey et al. |
| 2002/0190984 A1 | 12/2002 | Seiler et al. |
| 2003/0005464 A1 | 1/2003 | Gropper et al. |
| 2003/0013951 A1 | 1/2003 | Stefanescu |
| 2003/0016850 A1 | 1/2003 | Kaufman et al. |
| 2003/0028402 A1 | 2/2003 | Ulrich et al. |
| 2003/0034973 A1 | 2/2003 | Zuiderveld |
| 2003/0037054 A1 | 2/2003 | Dutta et al. |
| 2003/0053668 A1 | 3/2003 | Ditt et al. |
| 2003/0055896 A1 | 3/2003 | Hu et al. |
| 2003/0065613 A1 | 4/2003 | Smith |
| 2003/0071829 A1 | 4/2003 | Bodicker et al. |
| 2003/0101291 A1 | 5/2003 | Mussack et al. |
| 2003/0115083 A1 | 6/2003 | Masarie et al. |
| 2003/0120516 A1 | 6/2003 | Perednia |
| 2003/0130973 A1 | 7/2003 | Sumner, II et al. |
| 2003/0140044 A1 | 7/2003 | Mok et al. |
| 2003/0140141 A1 | 7/2003 | Mullen et al. |
| 2003/0156745 A1 | 8/2003 | Saito et al. |
| 2003/0160095 A1 | 8/2003 | Segal |

(56) References Cited

U.S. PATENT DOCUMENTS

| | | |
|---|---|---|
| 2003/0164860 A1 | 9/2003 | Shen et al. |
| 2003/0184778 A1 | 10/2003 | Chiba |
| 2003/0187689 A1 | 10/2003 | Barnes et al. |
| 2003/0190062 A1 | 10/2003 | Noro et al. |
| 2003/0195416 A1 | 10/2003 | Toth |
| 2003/0204420 A1 | 10/2003 | Wilkes et al. |
| 2003/0215120 A1 | 11/2003 | Uppaluri et al. |
| 2003/0215122 A1 | 11/2003 | Tanaka |
| 2004/0008900 A1 | 1/2004 | Jabri et al. |
| 2004/0015703 A1 | 1/2004 | Madison et al. |
| 2004/0024303 A1 | 2/2004 | Banks et al. |
| 2004/0027359 A1 | 2/2004 | Aharon et al. |
| 2004/0061889 A1 | 4/2004 | Wood et al. |
| 2004/0068170 A1 | 4/2004 | Wang et al. |
| 2004/0077952 A1 | 4/2004 | Rafter et al. |
| 2004/0086163 A1 | 5/2004 | Moriyama et al. |
| 2004/0088192 A1 | 5/2004 | Schmidt et al. |
| 2004/0105030 A1 | 6/2004 | Yamane |
| 2004/0105574 A1 | 6/2004 | Pfaff |
| 2004/0114714 A1 | 6/2004 | Minyard et al. |
| 2004/0122705 A1 | 6/2004 | Sabol et al. |
| 2004/0122787 A1 | 6/2004 | Avinash et al. |
| 2004/0141661 A1 | 7/2004 | Hanna et al. |
| 2004/0143582 A1 | 7/2004 | Vu |
| 2004/0161139 A1 | 8/2004 | Samara et al. |
| 2004/0161164 A1 | 8/2004 | Dewaele |
| 2004/0165791 A1 | 8/2004 | Kaltanji |
| 2004/0172306 A1 | 9/2004 | Wohl et al. |
| 2004/0174429 A1 | 9/2004 | Chu |
| 2004/0190780 A1 | 9/2004 | Shiibashi et al. |
| 2004/0197015 A1 | 10/2004 | Fan et al. |
| 2004/0202387 A1 | 10/2004 | Yngvesson |
| 2004/0243435 A1 | 12/2004 | Williams |
| 2004/0252871 A1 | 12/2004 | Tecotzky et al. |
| 2004/0254816 A1 | 12/2004 | Myers |
| 2004/0255252 A1 | 12/2004 | Rodriguez et al. |
| 2005/0010531 A1 | 1/2005 | Kushalnagar et al. |
| 2005/0027569 A1 | 2/2005 | Gollogly et al. |
| 2005/0027570 A1 | 2/2005 | Maier et al. |
| 2005/0043970 A1 | 2/2005 | Hsieh |
| 2005/0063575 A1 | 3/2005 | Ma et al. |
| 2005/0065424 A1 | 3/2005 | Shah et al. |
| 2005/0074150 A1 | 4/2005 | Bruss |
| 2005/0074157 A1 | 4/2005 | Thomas, III |
| 2005/0075544 A1 | 4/2005 | Shapiro et al. |
| 2005/0088534 A1 | 4/2005 | Shen et al. |
| 2005/0107689 A1 | 5/2005 | Sasano |
| 2005/0108058 A1 | 5/2005 | Weidner et al. |
| 2005/0110791 A1 | 5/2005 | Krishnamoorthy et al. |
| 2005/0111733 A1 | 5/2005 | Fors et al. |
| 2005/0113681 A1 | 5/2005 | DeFreitas et al. |
| 2005/0114178 A1 | 5/2005 | Krishnamurthy et al. |
| 2005/0114179 A1 | 5/2005 | Brackett et al. |
| 2005/0114283 A1 | 5/2005 | Pearson et al. |
| 2005/0143654 A1 | 6/2005 | Zuiderveld et al. |
| 2005/0171818 A1 | 8/2005 | McLaughlin |
| 2005/0184988 A1 | 8/2005 | Yanof et al. |
| 2005/0197860 A1 | 9/2005 | Joffe et al. |
| 2005/0203775 A1 | 9/2005 | Chesbrough |
| 2005/0238218 A1 | 10/2005 | Nakamura |
| 2005/0244041 A1 | 11/2005 | Tecotzky et al. |
| 2005/0251013 A1 | 11/2005 | Krishnan |
| 2005/0254729 A1 | 11/2005 | Saito et al. |
| 2005/0259118 A1 | 11/2005 | Mojaver et al. |
| 2005/0273009 A1 | 12/2005 | Deischinger et al. |
| 2006/0008181 A1 | 1/2006 | Takekoshi |
| 2006/0031097 A1 | 2/2006 | Lipscher et al. |
| 2006/0050152 A1 | 3/2006 | Rai et al. |
| 2006/0058603 A1 | 3/2006 | Dave et al. |
| 2006/0061570 A1 | 3/2006 | Cheryauka et al. |
| 2006/0093027 A1 | 5/2006 | Draving et al. |
| 2006/0093139 A1 | 5/2006 | Quan |
| 2006/0093198 A1 | 5/2006 | Fram et al. |
| 2006/0093199 A1 | 5/2006 | Fram et al. |
| 2006/0093207 A1 | 5/2006 | Reicher et al. |
| 2006/0095423 A1 | 5/2006 | Reicher et al. |
| 2006/0095426 A1 | 5/2006 | Takachio et al. |
| 2006/0106642 A1 | 5/2006 | Reicher et al. |
| 2006/0111937 A1 | 5/2006 | Yarger et al. |
| 2006/0111941 A1 | 5/2006 | Blom |
| 2006/0122482 A1 | 6/2006 | Mariotti et al. |
| 2006/0171574 A1 | 8/2006 | DelMonego et al. |
| 2006/0181548 A1 | 8/2006 | Hafey |
| 2006/0188134 A1 | 8/2006 | Quist |
| 2006/0230072 A1 | 10/2006 | Partovi et al. |
| 2006/0238546 A1 | 10/2006 | Handley et al. |
| 2006/0239573 A1 | 10/2006 | Novatzky et al. |
| 2006/0241979 A1 | 10/2006 | Sato et al. |
| 2006/0267976 A1 | 11/2006 | Saito et al. |
| 2006/0274145 A1 | 12/2006 | Reiner |
| 2006/0276708 A1 | 12/2006 | Peterson et al. |
| 2006/0277075 A1 | 12/2006 | Salwan |
| 2006/0282408 A1 | 12/2006 | Wisely et al. |
| 2006/0282447 A1 | 12/2006 | Hollebeek |
| 2007/0009078 A1 | 1/2007 | Saito et al. |
| 2007/0021977 A1 | 1/2007 | Elsholz |
| 2007/0050701 A1 | 3/2007 | El Emam et al. |
| 2007/0055550 A1 | 3/2007 | Courtney et al. |
| 2007/0064984 A1 | 3/2007 | Vassa et al. |
| 2007/0067124 A1 | 3/2007 | Kimpe et al. |
| 2007/0073556 A1 | 3/2007 | Lau et al. |
| 2007/0106535 A1 | 5/2007 | Matsunaga |
| 2007/0106633 A1 | 5/2007 | Reiner |
| 2007/0109299 A1 | 5/2007 | Peterson |
| 2007/0109402 A1 | 5/2007 | Niwa |
| 2007/0110294 A1 | 5/2007 | Schaap et al. |
| 2007/0116345 A1 | 5/2007 | Peterson et al. |
| 2007/0116346 A1 | 5/2007 | Peterson et al. |
| 2007/0122016 A1 | 5/2007 | Brejl et al. |
| 2007/0124541 A1 | 5/2007 | Lang et al. |
| 2007/0140536 A1 | 6/2007 | Sehnert |
| 2007/0159962 A1 | 7/2007 | Mathavu et al. |
| 2007/0162308 A1 | 7/2007 | Peters |
| 2007/0165917 A1 | 7/2007 | Cao et al. |
| 2007/0174079 A1 | 7/2007 | Kraus |
| 2007/0192138 A1 | 8/2007 | Saito et al. |
| 2007/0192140 A1 | 8/2007 | Gropper |
| 2007/0237380 A1 | 10/2007 | Iwase et al. |
| 2007/0239481 A1 | 10/2007 | DiSilvestro et al. |
| 2007/0245308 A1 | 10/2007 | Hill et al. |
| 2007/0270695 A1 | 11/2007 | Keen |
| 2008/0016111 A1 | 1/2008 | Keen |
| 2008/0019581 A1 | 1/2008 | Gkanatsios et al. |
| 2008/0021877 A1 | 1/2008 | Saito et al. |
| 2008/0031507 A1 | 2/2008 | Uppaluri et al. |
| 2008/0059245 A1 | 3/2008 | Sakaida et al. |
| 2008/0097186 A1 | 4/2008 | Biglieri et al. |
| 2008/0100612 A1 | 5/2008 | Dastmalchi et al. |
| 2008/0103828 A1 | 5/2008 | Squilla et al. |
| 2008/0118120 A1 | 5/2008 | Wegenkittl et al. |
| 2008/0125846 A1 | 5/2008 | Battle et al. |
| 2008/0126982 A1* | 5/2008 | Sadikali ............... G06F 19/321 |
| | | 715/810 |
| 2008/0130966 A1 | 6/2008 | Crucs |
| 2008/0133526 A1 | 6/2008 | Haitani et al. |
| 2008/0136838 A1 | 6/2008 | Goede et al. |
| 2008/0136868 A1 | 6/2008 | Goede et al. |
| 2008/0275913 A1 | 11/2008 | van Arragon et al. |
| 2008/0279439 A1 | 11/2008 | Minyard et al. |
| 2008/0300484 A1 | 12/2008 | Wang et al. |
| 2009/0005668 A1 | 1/2009 | West et al. |
| 2009/0022375 A1 | 1/2009 | Fidrich |
| 2009/0022386 A1 | 1/2009 | Karau et al. |
| 2009/0028410 A1 | 1/2009 | Shimazaki |
| 2009/0080719 A1 | 3/2009 | Watt |
| 2009/0091566 A1 | 4/2009 | Turney et al. |
| 2009/0094513 A1 | 4/2009 | Bay |
| 2009/0123052 A1 | 5/2009 | Ruth et al. |
| 2009/0129643 A1 | 5/2009 | Natanzon et al. |
| 2009/0129651 A1* | 5/2009 | Zagzebski ........... G01S 7/52046 |
| | | 382/131 |
| 2009/0132586 A1 | 5/2009 | Napora et al. |
| 2009/0150481 A1 | 6/2009 | Garcia et al. |
| 2009/0164247 A1 | 6/2009 | Dobler et al. |

(56) References Cited

U.S. PATENT DOCUMENTS

| | | |
|---|---|---|
| 2009/0182577 A1 | 7/2009 | Squilla et al. |
| 2009/0198514 A1 | 8/2009 | Rhodes |
| 2009/0213034 A1 | 8/2009 | Wu et al. |
| 2009/0248442 A1 | 10/2009 | Pacheco et al. |
| 2009/0268986 A1 | 10/2009 | Holstein et al. |
| 2009/0297013 A1 | 12/2009 | Chaudhuri |
| 2009/0326373 A1 | 12/2009 | Boese et al. |
| 2010/0053353 A1 | 3/2010 | Hunter et al. |
| 2010/0086182 A1 | 4/2010 | Hui |
| 2010/0119027 A1 | 5/2010 | Peterson et al. |
| 2010/0131887 A1 | 5/2010 | Salazar-Ferrer et al. |
| 2010/0138239 A1 | 6/2010 | Reicher et al. |
| 2010/0138240 A1 | 6/2010 | Leib et al. |
| 2010/0198608 A1 | 8/2010 | Kaboff et al. |
| 2010/0201714 A1 | 8/2010 | Reicher et al. |
| 2010/0211409 A1* | 8/2010 | Kotula .............. G06Q 10/06 705/3 |
| 2010/0246981 A1 | 9/2010 | Hu et al. |
| 2010/0299157 A1 | 11/2010 | Fram et al. |
| 2011/0016430 A1 | 1/2011 | Fram et al. |
| 2011/0019886 A1 | 1/2011 | Mizuno |
| 2011/0110572 A1 | 5/2011 | Guehring et al. |
| 2011/0267339 A1 | 11/2011 | Fram et al. |
| 2011/0293162 A1 | 12/2011 | Pajeau |
| 2011/0316873 A1 | 12/2011 | Reicher et al. |
| 2012/0070048 A1 | 3/2012 | Van Den Brink |
| 2012/0130729 A1 | 5/2012 | Raizada et al. |
| 2012/0136794 A1 | 5/2012 | Kushalnagar et al. |
| 2012/0163684 A1 | 6/2012 | Natanzon et al. |
| 2012/0183191 A1 | 7/2012 | Nakamura |
| 2012/0194540 A1 | 8/2012 | Reicher et al. |
| 2012/0196258 A1 | 8/2012 | Geijsen et al. |
| 2012/0208592 A1 | 8/2012 | Davis et al. |
| 2012/0284657 A1 | 11/2012 | Hafey et al. |
| 2012/0320093 A1 | 12/2012 | Zhu et al. |
| 2012/0324400 A1 | 12/2012 | Caliendo, Jr. et al. |
| 2013/0070998 A1 | 3/2013 | Shibata |
| 2013/0076681 A1 | 3/2013 | Sirpal et al. |
| 2013/0083023 A1 | 4/2013 | Fram et al. |
| 2013/0129198 A1 | 5/2013 | Sherman et al. |
| 2013/0129231 A1* | 5/2013 | Dale .............. G06K 9/6254 382/224 |
| 2013/0159019 A1 | 6/2013 | Reicher |
| 2013/0169661 A1 | 7/2013 | Reicher et al. |
| 2013/0195329 A1 | 8/2013 | Canda et al. |
| 2013/0198682 A1 | 8/2013 | Matas et al. |
| 2013/0297331 A1 | 11/2013 | Zuehlsdorff et al. |
| 2014/0022194 A1 | 1/2014 | Ito |
| 2014/0096049 A1 | 4/2014 | Vonshak et al. |
| 2014/0119514 A1 | 5/2014 | Miyazawa |
| 2014/0142983 A1 | 5/2014 | Backhaus et al. |
| 2014/0378810 A1 | 12/2014 | Davis et al. |
| 2015/0046349 A1 | 2/2015 | Michael, Jr. et al. |
| 2015/0101066 A1 | 4/2015 | Fram |
| 2015/0160848 A1 | 6/2015 | Gkanatsios et al. |
| 2015/0363104 A1 | 12/2015 | Ichioka et al. |
| 2016/0034110 A1 | 2/2016 | Edwards |
| 2016/0270746 A1 | 9/2016 | Foos et al. |
| 2016/0335395 A1 | 11/2016 | Wu et al. |
| 2017/0038951 A1 | 2/2017 | Reicher et al. |
| 2017/0039321 A1 | 2/2017 | Reicher et al. |
| 2017/0039350 A1 | 2/2017 | Reicher et al. |
| 2017/0039705 A1 | 2/2017 | Fram et al. |
| 2017/0046014 A1 | 2/2017 | Fram |
| 2017/0046483 A1 | 2/2017 | Reicher et al. |
| 2017/0046485 A1 | 2/2017 | Reicher et al. |
| 2017/0046495 A1 | 2/2017 | Fram |
| 2017/0046870 A1 | 2/2017 | Fram et al. |
| 2017/0053404 A1 | 2/2017 | Reicher et al. |
| 2017/0200064 A1 | 7/2017 | Reicher et al. |
| 2017/0200269 A1 | 7/2017 | Reicher et al. |
| 2017/0200270 A1 | 7/2017 | Reicher et al. |
| 2017/0206324 A1 | 7/2017 | Reicher et al. |
| 2017/0239720 A1 | 8/2017 | Levin et al. |
| 2017/0293720 A1 | 10/2017 | Reicher et al. |
| 2017/0301090 A1 | 10/2017 | Fram et al. |
| 2017/0308647 A1 | 10/2017 | Reicher et al. |
| 2018/0059918 A1 | 3/2018 | Reicher et al. |
| 2018/0225824 A1 | 8/2018 | Fram et al. |
| 2019/0009371 A1 | 1/2019 | Veerasamy et al. |

OTHER PUBLICATIONS

US 8,208,705 B2, 06/2012, Reicher et al. (withdrawn)

U.S. Appl. No. 14/540,830, Systems and Methods for Viewing Medical Images, filed Nov. 13, 2014.

U.S. Appl. No. 14/502,055, Systems and Methods for Interleaving Series of Medical Images, filed Sep. 13, 2014.

U.S. Appl. No. 14/095,123, Systems and Methods for Retrieval of Medical Data, filed Dec. 3, 2013.

U.S. Appl. No. 14/081,225, Systems and Methods for Viewing Medical 3D Imaging Volumes, filed Nov. 15, 2013.

U.S. Appl. No. 14/244,431, Systems and Methods for Matching, Naming, and Displaying Medical Images, filed Apr. 3, 2014.

U.S. Appl. No. 14/298,806, Smart Placement Rules, filed Jun. 6, 2013.

U.S. Appl. No. 14/043,165, Automated Document Filing, filed Oct. 1, 2013.

U.S. Appl. No. 11/942,687, Smart Forms, filed Nov. 19, 2007.

U.S. Appl. No. 14/043,165, Automated Document Filing, dated Oct. 1, 2013.

U.S. Appl. No. 11/944,000, Exam Scheduling With Customer Configured Notifications, filed Nov. 21, 2007.

U.S. Appl. No. 13/768,765, System and Method of Providing Dynamic and Customizable Medical Examination Forms, filed Feb. 15, 2013.

U.S. Appl. No. 14/687,853, Selective Processing of Medical Images, filed Apr. 15, 2015.

U.S. Appl. No. 15/163,600, Selective Display of Medical Images, filed May 24, 2016.

U.S. Appl. No. 14/792,210, Dynamic Montage Reconstruction, filed Jul. 6, 2015.

U.S. Appl. No. 15/140,346, Database Systems and Interactive User Interfaces for Dynamic Interaction Wiith, and Sorting of, Digital Medical Image Data, filed Apr. 27, 2016.

U.S. Appl. No. 15/140,363, Database Systems and Interactive User Interfaces for Dynamic Interation With, and Comparison of, Digital Medical Image Data, filed Apr. 27, 2016.

U.S. Appl. No. 15/140,351, Database Systems and Interactive User Interfaces for Dynamic Interaction With, and Review of, Digital Medical Image Data, filed Apr. 27, 2016.

U.S. Appl. No. 14/540,830, filed Nov. 13, 2014 including its ongoing prosecution history, including without limitation Office Actions, Amendments, Remarks, and any other potentially relevant documents., Reicher et al.

U.S. Appl. No. 14/502,055, filed Sep. 30, 2014 including its ongoing prosecution history, including without limitation Office Actions, Amendments, Remarks, and any other potentially relevant documents., Fram et al.

U.S. Appl. No. 14/095,123, filed Dec. 3, 2013 including its ongoing prosecution history, including without limitation Office Actions, Amendments, Remarks, and any other potentially relevant documents., Reicher et al.

U.S. Appl. No. 14/081,225, filed Nov. 15, 2013 including its ongoing prosecution history, including without limitation Office Actions, Amendments, Remarks, and any other potentially relevant documents, Fram et al.

U.S. Appl. No. 14/244,431, filed Apr. 3, 2014 including its ongoing prosecution history, including without limitation Office Actions, Amendments, Remarks, and any other potentially relevant documents., Reicher et al.

U.S. Appl. No. 14/298,806, filed Jun. 6, 2014 including its ongoing prosecution history, including without limitation Office Actions, Amendments, Remarks, and any other potentially relevant documents., Reicher et al.

(56) References Cited

OTHER PUBLICATIONS

U.S. Appl. No. 11/942,687, filed Nov. 19, 2007 including its ongoing prosecution history, including without limitation Office Actions, Amendments, Remarks, and any other potentially relevant documents., Reicher, et al.
U.S. Appl. No. 14/043,165, filed Oct. 1, 2013 including its ongoing prosecution history, including without limitation Office Actions, Amendments, Remarks, and any other potentially relevant documents., Reicher, et al.
U.S. Appl. No. 11/944,000, filed Nov. 21, 2007 including its ongoing prosecution history, including without limitation Office Actions, Amendments, Remarks, and any other potentially relevant documents., Reicher, et al.
U.S. Appl. No. 12/437,522, filed May 7, 2009, Fram.
U.S. Appl. No. 14/687,853, filed Apr. 15, 2015 including its ongoing prosecution history, including without limitation Office Actions, Amendments, Remarks, and any other potentially relevant documents., Reicher, et al.
U.S. Appl. No. 14/792,210, filed Jul. 6, 2015 including its ongoing prosecution history, including without limitation Office Actions, Amendments, Remarks, and any other potentially relevant documents., Reicher.
Non-Final Office Action dated Aug. 28, 2007 in U.S. Appl. No. 11/179,384.
Final Office Action dated Jun. 26, 2008 in U.S. Appl. No. 11/179,384.
Non-Final Office Action dated Dec. 29, 2008 in U.S. Appl. No. 11/179,384.
Final Office Action dated Jul. 24, 2009, in U.S. Appl. No. 11/179,384.
Notice of Allowance dated Nov. 3, 2009, in U.S. Appl. No. 11/179,384.
Non-Final Office Action dated Aug. 18, 2010 in U.S. Appl. No. 12/702,976.
Interview Summary dated Dec. 1, 2010, in U.S. Appl. No. 12/702,976.
Final Office Action dated Feb. 17, 2011 in U.S. Appl. No. 12/702,976.
Interview Summary dated May 31, 2011 in U.S. Appl. No. 12/702,976.
Notice of Allowance dated Jul. 20, 2011, in U.S. Appl. No. 12/702,976.
Office Action dated Dec. 1, 2011, in U.S. Appl. No. 13/228,349.
Notice of Allowance dated Feb. 6, 2012, in U.S. Appl. No. 13/228,349.
Notice of Allowance dated Jul. 20, 2012, in U.S. Appl. No. 13/228,349.
Office Action dated Dec. 11, 2013, in U.S. Appl. No. 13/477,853.
Interview Summary dated Mar. 14, 2014, in U.S. Appl. No. 13/477,853.
Final Office Action dated Jun. 13, 2014, in U.S. Appl. No. 13/477,853.
Notice of Allowance dated Aug. 15, 2014, in U.S. Appl. No. 13/477,853.
Non-Final Office Action dated Oct. 1, 2009, in U.S. Appl. No. 11/268,261.
Notice of Allowance dated Feb. 2, 2010, in U.S. Appl. No. 11/268,261.
Interview Summary dated Jan. 25, 2010, in U.S. Appl. No. 11/268,261.
Interview Summary dated May 14, 2010, in U.S. Appl. No. 11/268,261.
Notice of Allowance dated May 17, 2010, in U.S. Appl. No. 11/268,261.
Supplemental Notice of Allowance dated Aug. 6, 2010, in U.S. Appl. No. 11/268,261.
Notice of Allowance dated Oct. 8, 2010, in U.S. Appl. No. 11/268,261.
Notice of Allowance dated Dec. 3, 2010, in U.S. Appl. No. 11/268,261.
Notice of Allowance dated Jan. 6, 2011, in U.S. Appl. No. 11/268,261.
Office Action dated May 16, 2011, in U.S. Appl. No. 12/857,915.
Interview Summary dated Sep. 6, 2011, in U.S. Appl. No. 12/857,915.
Final Office Action dated Dec. 15, 2011, in U.S. Appl. No. 12/857,915.
Office Action dated Jun. 12, 2012, in U.S. Appl. No. 12/857,915.
Office Action dated Aug. 23, 2013, in U.S. Appl. No. 12/857,915.
Interview Summary dated Feb. 4, 2014, in U.S. Appl. No. 12/857,915.
Notice of Allowance dated Jul. 3, 2014, in U.S. Appl. No. 12/857,915.
"Corrected" Notice of Allowance dated Aug. 15, 2014, in U.S. Appl. No. 12/857,915.
Non-Final Office Action dated Jan. 20, 2016, in U.S. Appl. No. 14/502,055.
Interview Summary dated Apr. 14, 2016, in U.S. Appl. No. 14/502,055.
Non-Final Office Action dated May 13, 2009, in U.S. Appl. No. 11/265,979.
Final Office Action dated Dec. 22, 2009 in U.S. Appl. No. 11/265,979.
Non-Final Office Action dated Jul. 8, 2010 in U.S. Appl. No. 11/265,979.
Interview Summary dated Mar. 4, 2010 in U.S. Appl. No. 11/265,979.
Interview Summary dated Nov. 16, 2010 in U.S. Appl. No. 11/265,979.
Final Office Action dated Dec. 23, 2010 in U.S. Appl. No. 11/265,979.
Interview Summary dated Mar. 17, 2011 in U.S. Appl. No. 11/265,979.
Notice of Allowance dated May 26, 2011 in U.S. Appl. No. 11/265,979.
Office Action dated Jun. 8, 2012 in U.S. Appl. No. 13/171,081.
Interview Summary dated Jul. 31, 2012 in U.S. Appl. No. 13/171,081.
Final Office Action dated Oct. 12, 2012 in U.S. Appl. No. 13/171,081.
Interview Summary dated Nov. 6, 2012 in U.S. Appl. No. 13/171,081.
Notice of Allowance, dated Sep. 4, 2013, in U.S. Appl. No. 13/171,081.
Office Action dated Mar. 3, 2015 in U.S. Appl. No. 14/095,123.
Interview Summary dated May 1, 2015 in U.S. Appl. No. 14/095,123.
Final Office Action dated Jul. 23, 2015 in U.S. Appl. No. 14/095,123.
Interview Summary dated Aug. 27, 2015 in U.S. Appl. No. 14/095,123.
Office Action dated Feb. 23, 2016 in U.S. Appl. No. 14/095,123.
Non-Final Office Action dated Aug. 24, 2009 in U.S. Appl. No. 11/268,262.
Non-Final Office Action dated Apr. 16, 2010 in U.S. Appl. No. 11/268,262.
Interview Summary dated Nov. 24, 2009 in U.S. Appl. No. 11/268,262.
Interview Summary dated May 12, 2010 in U.S. Appl. No. 11/268,262.
Final Office Action dated Oct. 28, 2010 in U.S. Appl. No. 11/268,262.
Interview Summary dated Dec. 1, 2010 in U.S. Appl. No. 11/268,262.
Notice of Allowance dated Dec. 1, 2010 in U.S. Appl. No. 11/268,262.
Notice of Allowance dated Feb. 25, 2011 in U.S. Appl. No. 11/268,262.
Non-Final Office Action dated Jan. 11, 2012 in U.S. Appl. No. 13/079,597.
Notice of Allowance dated Apr. 25, 2012, in U.S. Appl. No. 13/079,597.
Non-Final Office Action dated Apr. 4, 2013 in U.S. Appl. No. 13/535,758.
Notice of Allowance, dated Aug. 23, 2013 in U.S. Appl. No. 13/535,758.
Office Action dated Mar. 10, 2016 in U.S. Appl. No. 14/081,225.
Non-Final Office Action dated Jul. 27, 2009 in U.S. Appl. No. 11/265,978.
Notice of Allowance dated Nov. 19, 2009 in U.S. Appl. No. 11/265,978.
Notice of Allowance dated Apr. 19, 2010 in U.S. Appl. No. 11/265,978.
Supplemental Notice of Allowance dated May 3, 2010 in U.S. Appl. No. 11/265,978.
Supplemental Notice of Allowance dated Aug. 3, 2010 in U.S. Appl. No. 11/265,978.
Non-Final Office Action dated May 5, 2011 in U.S. Appl. No. 12/870,645.
Non-Final Office Action dated May 31, 2013, in U.S. Appl. No. 13/345,606.
Interview Summary dated Aug. 15, 2013, in U.S. Appl. No. 13/345,606.
Notice of Allowance, dated Jan. 9, 2014 in U.S. Appl. No. 13/345,606.
Non-Final Office Action dated Mar. 18, 2016 in U.S. Appl. No. 14/244,431.
Non-Final Office Action dated May 26, 2010 in U.S. Appl. No. 11/942,674.
Interview Summary dated Jul. 26, 2010 in U.S. Appl. No. 11/942,674.
Final Office Action dated Nov. 26, 2010 in U.S. Appl. No. 11/942,674.
Interview Summary dated Mar. 2, 2011 in U.S. Appl. No. 11/942,674.
Notice of Allowance, dated Apr. 1, 2011 in U.S. Appl. No. 11/942,674.
Non Final Office Action dated Nov. 10, 2011 in U.S. Appl. No. 13/118,085.
Interview Summary, dated Feb. 17, 2012, in U.S. Appl. No. 13/118,085.
Final Office Action, dated Apr. 13, 2012, in U.S. Appl. No. 13/118,085.
Notice of Allowance, dated Feb. 6, 2013, in U.S. Appl. No. 13/118,085.

(56) References Cited

OTHER PUBLICATIONS

Non Final Office Action dated Aug. 23, 2013 in U.S. Appl. No. 13/907,128.
Final Office Action dated Oct. 9, 2013 in U.S. Appl. No. 13/907,128.
Interview Summary dated Nov. 22, 2013 in U.S. Appl. No. 13/907,128.
Notice of Allowance dated Jan. 31, 2014 in U.S. Appl. No. 13/907,128.
Office Action, dated Dec. 29, 2014 in U.S. Appl. No. 14/298,806.
Interview Summary, dated Mar. 2, 2015 in U.S. Appl. No. 14/298,806.
Final Office Action, dated Jun. 17, 2015 in U.S. Appl. No. 14/298,806.
Office Action, dated Feb. 16, 2016 in U.S. Appl. No. 14/298,806.
Non Final Office Action dated Sep. 16, 2010 in U.S. Appl. No. 11/942,687.
Interview Summary dated Dec. 3, 2010 in U.S. Appl. No. 11/942,687.
Final Office Action, dated Apr. 5, 2011 in U.S. Appl. No. 11/942,687.
Office Action, dated Mar. 13, 2014 in U.S. Appl. No. 11/942,687.
Interview Summary, dated Jun. 17, 2014 in U.S. Appl. No. 11/942,687.
Office Action, dated Jul. 18, 2014 in U.S. Appl. No. 11/942,687.
Final Office Action, dated Jan. 5, 2015 in U.S. Appl. No. 11/942,687.
Interview Summary, dated Mar. 4, 2015 in U.S. Appl. No. 11/942,687.
PTAB Examiner's Answer, dated Feb. 25, 2016 in U.S. Appl. No. 11/942,687.
Non-Final Office Action dated Apr. 14, 2010 in U.S. Appl. No. 11/944,027.
Interview Summary dated May 13, 2010 in U.S. Appl. No. 11/944,027.
Final Office Action dated Dec. 23, 2010 in U.S. Appl. No. 11/944,027.
Interview Summary dated Mar. 31, 2011 in U.S. Appl. No. 11/944,027.
Office Action dated Apr. 19, 2012 in U.S. Appl. No. 11/944,027.
Interview Summary dated Jun. 28, 2012 in U.S. Appl. No. 11/944,027.
Final Office Action dated Oct. 22, 2012 in U.S. Appl. No. 11/944,027.
Notice of Allowance dated Jun. 5, 2013 in U.S. Appl. No. 11/944,027.
Office Action dated Oct. 14, 2014 in U.S. Appl. No. 14/043,165.
Final Office Action dated Apr. 1, 2015 in U.S. Appl. No. 14/043,165.
Office Action dated Oct. 2, 2015 in U.S. Appl. No. 14/043,165.
Interview Summary dated Dec. 21, 2015 in U.S. Appl. No. 14/043,165.
Final Office Action dated Feb. 17, 2016 in U.S. Appl. No. 14/043,165.
Non-Final Office Action dated Sep. 29, 2010 in U.S. Appl. No. 11/944,000.
Final Office Action dated Apr. 20, 2011 in U.S. Appl. No. 11/944,000.
Interview Summary dated Jun. 7, 2011 in U.S. Appl. No. 11/944,000.
Appeal Brief dated Mar. 4, 2013 in U.S. Appl. No. 11/944,000.
Examiner's Answer dated Jun. 26, 2013 in U.S. Appl. No. 11/944,000.
Board Decision dated Mar. 23, 2016 in U.S. Appl. No. 11/944,000.
Office Action dated Feb. 3, 2012 in U.S. Appl. No. 12/622,404.
Interview Summary dated May 8, 2012 in U.S. Appl. No. 12/622,404.
Final Office Action dated Aug. 6, 2012 in U.S. Appl. No. 12/622,404.
Notice of Allowance dated Oct. 15, 2012 in U.S. Appl. No. 12/622,404.
Office Action dated Mar. 17, 2015 in U.S. Appl. No. 13/768,765.
Interview Summary dated Jun. 11, 2015 in U.S. Appl. No. 13/768,765.
Notice of Allowance dated Aug. 28, 2015 in U.S. Appl. No. 13/768,765.
Notice of Allowability dated Nov. 20, 2015 in U.S. Appl. No. 13/768,765.
Office Action dated Mar. 4, 2013 in U.S. Appl. No. 12/891,543.
Interview Summary dated Apr. 5, 2013 in U.S. Appl. No. 12/891,543.
Notice of Allowance dated Nov. 14, 2013 in U.S. Appl. No. 12/891,543.
Office Action dated Sep. 11, 2014 in U.S. Appl. No. 14/179,328.
Notice of Allowance dated Jan. 14, 2015 in U.S. Appl. No. 14/179,328.
Office Action dated Aug. 13, 2015 in U.S. Appl. No. 14/687,853.
Notice of Allowance dated Feb. 25, 2016 in U.S. Appl. No. 14/687,853.
Office Action dated Jun. 27, 2014 in U.S. Appl. No. 13/572,397.
Final Office Action dated Jan. 13, 2015 in U.S. Appl. No. 13/572,397.
Notice of Allowance dated Mar. 19, 2015, 2015 in U.S. Appl. No. 13/572,397.
Office Action dated Aug. 6, 2014 in U.S. Appl. No. 13/572,547.
Notice of Allowance, dated Mar. 3, 2015 in U.S. Appl. No. 13/572,547.
Corrected Notice of Allowance, dated Apr. 10, 2015 in U.S. Appl. No. 13/572,547.
Corrected Notice of Allowance, dated May 21, 2015 in U.S. Appl. No. 13/572,547.
Office Action dated Jul. 30, 2014 in U.S. Appl. No. 13/572,552.
Interview Summary dated Sep. 3, 2014 in U.S. Appl. No. 13/572,552.
Final Office Action dated Jan. 28, 2015 in U.S. Appl. No. 13/572,552.
Interview Summary dated Apr. 23, 2015 in U.S. Appl. No. 13/572,552.
Notice of Allowance, dated May 8, 2015 in U.S. Appl. No. 13/572,552.
Crowley, Rebecca et al., Development of Visual Diagnostic Expertise in Pathology: an Information-processing Study, Jan. 2003, Journal of the American medical Informatics Association, vol. 10, No. 1, pp. 39-51.
Erickson, et al.: "Effect of Automated Image Registration on Radiologist Interpretation," Journal of Digital Imaging, vol. 20, No. 2 Jun. 2007; pp. 105-113.
Erickson, et al.: "Image Registration Improves Confidence and Accuracy of Image Interpretation," Special Issue-Imaging Informatics, Cancer Informatics 2007:1 19-24.
Mendelson, et al., "Informatics in Radiology—Image Exchange: IHE and the Evolution of Image Sharing," RadioGraphics, Nov.-Dec. 2008, vol. 28, No. 7.
Rosset et al.: "OsiriX: An Open-Source Software for Navigating in Multidimensional DICOM Images," Journal of digital Imaging, Sep. 2004, pp. 205-216.
Schellingerhout, Dawid, MD, et al.: "Coregistration of Head CT Comparison Studies: Assessment of Clinical Utility," Acad Radiol 2003; 10:242-248.
Ivetic, D., and Dragan, D., Medical Image on the Go!, 2009, J Med Syst, vol. 35, pp. 499-516.
Tahmoush, D. and Samet, H., A New Database for Medical Images and Information, 2007, Medical Imaging 2007; PACS and Imaging Informatics, vol. 6516. pp. 1-9.
U.S. Appl. No. 15/140,346, filed Apr. 27, 2016 including its ongoing prosecution history, including without limitation Office Actions, Amendments, Remarks, and any other potentially relevant documents., Reicher et al.
U.S. Appl. No. 15/140,363, filed Apr. 27, 2016 including its ongoing prosecution history, including without limitation Office Actions, Amendments, Remarks, and any other potentially relevant documents., Reicher et al.
U.S. Appl. No. 15/140,351, filed Apr. 27, 2016 including its ongoing prosecution history, including without limitation Office Actions, Amendments, Remarks, and any other potentially relevant documents., Reicher et al.
AGFA HealthCare, color brochure "IMPAX 6: Digital Image and Information Management," © 2012 Agfa HealthCare N.V. Downloaded from http://www.agfahealthcare.com/global/en/he/library/libraryopen?ID=32882925. Accessed on Feb. 9, 2015.
AGFA HealthCare, IMPAX 6.5 Datasheet (US)2012. © 2012 Agfa HealthCare N.V. Downloaded from http://www.agfahealthcare.com/global/en/he/library/libraryopen?ID=37459801. Accessed on Feb. 9, 2015.
AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.
ASPYRA's Imaging Solutions, 3 page color print out. Accessed at http://www.aspyra.com/imaging-solutions. Accessed on Feb. 9, 2015.
AVREO, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.
BRIT Systems, BRIT PACS View Viewer, 2 page color brochure, (BPB-BPV-0001). Downloaded from http://www.brit.com/pdfs/britpacsview.pdf. Accessed on Feb. 9, 2015.
BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.

(56) References Cited

OTHER PUBLICATIONS

BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.
CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.
Carestream, Cardiology PACS, 8 page color brochure. (CAT 866 6075 06/12). © Carestream Health, Inc., 2012. Downloaded from http://www.carestream.com/cardioPACS_brochure_M1-877.pdf. Accessed on Feb. 9, 2015.
Carestream, Vue PACS, 8 page color brochure. (CAT 300 1035 05/14). © Carestream Health, Inc., 2014. Downloaded from http://www.carestream.com/csPACS_brochure_M1-876.pdf. Accessed on Feb. 9, 2015.
Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.
CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.
DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015.
DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.
FUJIFILM Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.
FUJIFILM Medical Systems, SYNAPSE® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.
FUJIFILM Medical Systems, SYNAPSE® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.
GE Healthcare, Centricity PACS, in 8 page printout. Accessed at http://www3.gehealthcare.com/en/products/catagories/healthcare_it/medical_imaging_informatics_-_ris-pacs-cvis/centricity_pacs. Accessed on Feb. 9, 2015.
Handylife.com—Overview of Handy Patients Enterprise, in 2 page printout. Accessed from http://www.handylife.com/en/software/overview.html. Accessed on Feb. 18, 2015.
Handylife.com—Features of Handy Patients Enterprise, in 4 page printout. Accessed from http://www.handylife.com/en/software/features.html. Accessed on Feb. 18, 2015.
Handylife.com—Screenshots of Handy Patients Enterprise, in 2 page printout. Accessed from http://www.handylife.com/en/software/screenshots.html. Accessed on Feb. 18, 2015.
iCRco, I See the Future, in 12 pages, color brochure, (BR080809AUS), © 2009 iCRco.ClarityPACS. Downloaded from http://www.claritypacs.com/pdfs/ISeeFuture_26_Web.pdf. Accessed on Feb. 9, 2015.
Imageanalysis, dynamika, 2 page color brochure. Downloaded from http://www.imageanalysis.org.uk/what-we-do. Accessed on Feb. 9, 2015.
Imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#products-services/ctnu. Accessed on Feb. 9, 2015.
Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incorporated. Downloaded http://www.intelerad.com/wp-content/uploads/sites/2/2014/08/IntelePACS-brochure.pdf. Accessed on Feb. 9, 2015.
Intelerad, InteleViewer, 2 page color brochure, © 2014 Intelerad Medical Systems Incorporated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page in color printout. Accessed at http://www.lumedx..com/pacs.aspx. Accessed on Feb. 9, 2015.
McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.
Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.
NOVARAD Enterprise Imaging Solutions, NOVAPACS, 2 page (color) printout. Accessed at http://ww1.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/products_01.html. Accessed on Feb. 9, 2015.
PHILIPS IntelliSpace PACS, in 2 color page printout. Accessed at https://www.healthcare.philips.com/main/products/healthcare_informatics/products/enterprise_imaging_informatics/isite_pacs. Accessed on Feb. 9, 2015.
Philips, IntelliSpace: Multi-modality tumor tracking application versus manual PACS methods, A time study for Response Evaluation Criteria in Solid Tumors (RECIST). 2012, Koninklijke Philips Electronics N.V., in four pages.
RamSoft, RIS PACS Teleradiology, PowerServer PACS, Lite PACS, XU PACS Compare RamSoft PACS Products, 2 color page printout. Accessed at http://www.ramsoft.com/procducts/powerserver-pacs-overview. Accessed on Feb. 9, 2015.
Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.
ScImage, Cardiology PACS, in 8 color page printout. Accessed at http://www.scimage.com/solutions/clinical-solutions/cardiology. Accessed on Feb. 9, 2015.
Sectra RIS PACS, in 2 color page printout. Accessed at http://www/sectra.com/medical/diagnostic_imaging/solutions/ris-pacs/. Accessed on Feb. 9, 2015.

(56) References Cited

OTHER PUBLICATIONS

Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.
Stryker, OfficePACS Power—Digital Imaging, 8 page color brochure, (MPP-022 Rev 4 BC/MP 300 1/07). © 2007 Stryker. Downloaded from http://www/stryker.com/emea/Solutions/Imaging/OfficePACSPowerDigitalImaging/ssLINK/emea/1557/02268. Accessed on Feb. 9, 2015.
UltraRAD—ultra VISION, 1 page (color). Downloaded from http://www.ultraradcorp.com/pdf/UltraVISION.pdf. Accessed on Feb. 9, 2015.
VioStream for VitreaView, 2 color pages printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
VIZTEK Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager PACS, 3 page color brochure. Downloaded from http://www.intellirad.com.au/index.php/assets/Uploads/Voyager-Pacs3.pdf. Accessed on Feb. 9, 2015.
U.S. Appl. No. 15/254,627, Systems and Methods for Interleaving Series of Medical Images, filed Sep. 1, 2016.
U.S. Appl. No. 15/292,006, Systems and Methods for Viewing Medical 3D Imaging Volumes, filed Oct. 12, 2016.
U.S. Appl. No. 15/346,530, Systems and Methods for Matching, Naming, and Displaying Medical Images, filed Nov. 8, 2016.
U.S. Appl. No. 14/043,165, Automated Document Filings, filed Oct. 1, 2013.
U.S. Appl. No. 15/292,014, System and Method of Providing Dynamic and Customizable Medical Examination for, filed Oct. 12, 2016.
U.S. Appl. No. 15/292,023, Selective Display of Medical Images, filed Oct. 12, 2016.
U.S. Appl. No. 15/188,872, Intelligent Management of Computerized Advanced Processing, filed Jun. 21, 2016.
U.S. Appl. No. 15/188,819, Intelligent Management of Computerized Advanced Processing, filed Jun. 21, 2016.
U.S. Appl. No. 15/140,346, Database Systems and Interactive User Interfaces for Dynamic Interaction With, and Sorting of, Digital Medical Image Data, filed Apr. 27, 2016.
U.S. Appl. No. 15/140,351, Database Systems and Interactive User Interfaces for Dynamic Interation With, and Comparison of, Digital Medical Image Data, filed Apr. 27, 2016.
Office Action dated Jan. 17, 2017, in U.S. Appl. No. 14/540,830.
Notice of Allowance dated Jun. 2, 2016, in U.S. Appl. No. 14/502,055.
Notice of Corrected Allowability dated Jul. 14, 2016, in U.S. Appl. No. 14/502,055.
Notice of Corrected Allowability dated Sep. 19, 2016, in U.S. Appl. No. 14/502,055.
Office Action dated Dec. 12, 2016, in U.S. Appl. No. 15/254,627.
Final Office Action dated Jul. 20, 2016 in U.S. Appl. No. 14/095,123.
Corrected Notice of Allowance dated Jun. 27, 2016, in U.S. Appl. No. 14/502,055.
Notice of Allowance dated Sep. 2, 2016 in U.S. Appl. No. 14/081,225.

Corrected Notice of Allowance dated Oct. 21, 2016 in U.S. Appl. No. 14/081,225.
Interview Summary dated Jun. 17, 2016 in U.S. Appl. No. 14/244,431.
Notice of Allowance dated Aug. 18, 2016 in U.S. Appl. No. 14/244,431.
Corrected Notice of Allowance dated Nov. 16, 2016 in U.S. Appl. No. 14/244,431.
Final Office Action, dated Jul. 21, 2016 in U.S. Appl. No. 14/298,806.
Appeal Brief dated Jul. 15, 2016 in U.S. Appl. No. 14/043,165.
Examiner's Answer dated Nov. 14, 2016, in U.S. Appl. No. 14/043,165.
Office Action, dated Jul. 15, 2016 in U.S. Appl. No. 11/944,000.
Notice of Allowability dated Jul. 28, 2016 in U.S. Appl. No. 13/768,765.
Supplemental Notice of Allowance dated Jun. 2, 2016 in U.S. Appl. No. 14/687,853.
Notice of Allowance dated Aug. 11, 2016 in U.S. Appl. No. 15/163,600.
Supplemental Notice of Allowance dated Sep. 14, 2016 in U.S. Appl. No. 15/163,600.
Office Action, dated Jan. 12, 2017 in U.S. Appl. No. 15/292,023.
Restriction Requirement, dated Jul. 28, 2015 in U.S. Appl. No. 14/139,068.
Office Action, dated Mar. 11, 2016 in U.S. Appl. No. 14/139,068.
Notice of Allowance, dated Sep. 21, 2016 in U.S. Appl. No. 14/139,068.
Sprawls, "Image Characteristics and Quality," Physical Principles of Medical Imaging, http://www.sprawls.org/resources pp. 1-14.
TeraRecon iNtuition pamphlet in 20 pages, retrieved on Nov. 8, 2013, available at http://int.terarecon.com/wp-content/uploads/2013/11/brochure_english2013.pdf.
TeraRecon iNtuition—Workflow. <www.terarecon.com/wordpress/our-solutions/intuition-workflow> Last accessed Nov. 8, 2013. 2 pages.
Non-Final Office Action from the U.S. Patent and Trademark Office for U.S. Appl. No. 15/140,351 dated Jul. 30, 2018 (25 pages).
Notice of Allowance from the U.S. Patent and Trademark Office for U.S. Appl. No. 15/188,872 dated Aug. 23, 2019 (10 pages).
Notice of Allowance from the U.S. Patent and Trademark Office for U.S. Appl. No. 14/792,210 dated Jun. 17, 2019 (10 pages).
Corrected Notice of Allowability from the U.S. Patent and Trademark Office for U.S. Appl. No. 14/792,210 dated Sep. 5, 2019 (2 pages).
Non-Final Office Action from the U.S. Patent and Trademark Office for U.S. Appl. No. 15/140,346 dated May 28, 2019 (39 pages).
Non-Final Office Action from the U.S. Patent and Trademark Office for U.S. Appl. No. 15/140,351 dated May 21, 2019 (14 pages).
Non-Final Office Action from the U.S. Patent and Trademark Office for U.S. Appl. No. 15/140,363 dated Jun. 3, 2019 (33 pages).
Final Office Action from the U.S. Patent and Trademark Office for U.S. Appl. No. 15/140,346 dated Oct. 31, 2019 (41 pages).
Final Office Action from the U.S. Patent and Trademark Office for U.S. Appl. No. 15/140,351 dated Nov. 14, 2019 (14 pages).
Notice of Allowance from the U.S. Patent and Trademark Office for U.S. Appl. No. 14/792,210 dated Oct. 11, 2019 (9 pages).
Examiner Interview Summary from the U.S. Patent and Trademark Office for U.S. Appl. No. 11/179,384 dated Sep. 24, 2008 (4 pages).
Examiner Interview Summary from the U.S. Patent and Trademark Office for U.S. Appl. No. 11/179,384 dated Feb. 18, 2009 (2 pages).
Advisory Action from the U.S. Patent and Trademark Office for U.S. Appl. No. 11/179,384 dated Sep. 17, 2009 (3 pages).
Notice of Allowance from the U.S. Patent and Trademark Office for U.S. Appl. No. 11/265,979 dated May 13, 2011 (14 pages).
Issue Notice from the U.S. Patent and Trademark Office for U.S. Appl. No. 11/268,261 dated Sep. 1, 2010 (1 page).
Interview Summary from the U.S. Patent and Trademark Office for U.S. Appl. No. 11/942,687 dated Jun. 10, 2011 (3 pages).
Patent Board Decision from the U.S. Patent and Trademark Office for U.S. Appl. No. 11/942,687 dated Dec. 22, 2017 (13 pages).
Examiner Interview Summary from the U.S. Patent and Trademark Office for U.S. Appl. No. 11/944,000 dated Feb. 4, 2011 (3 pages).
Advisory Action from the U.S. Patent and Trademark Office for U.S. Appl. No. 11/944,000 dated Aug. 1, 2011 (3 pages).

(56) References Cited

OTHER PUBLICATIONS

Non-Final Office Action from the U.S. Patent and Trademark Office for U.S. Appl. No. 11/944,000 dated Oct. 5, 2012 (11 pages).
Notice of Allowance from the U.S. Patent and Trademark Office for U.S. Appl. No. 11/944,000 dated Jan. 30, 2017 (12 pages).
Examiner-Initiated Interview Summary from the U.S. Patent and Trademark Office for U.S. Appl. No. 12/857,915 dated Jul. 3, 2014 (1 page).
Examiner Interview Summary from the U.S. Patent and Trademark Office for U.S. Appl. No. 12/870,645 dated Jun. 10, 2011 (2 pages).
Notice of Allowance from the U.S. Patent and Trademark Office for U.S. Appl. No. 12/870,645 dated Sep. 13, 2011 (8 pages).
Notice of Allowance from the U.S. Patent and Trademark Office for U.S. Appl. No. 12/870,645 dated Dec. 7, 2011 (4 pages).
Notice of Allowance from the U.S. Patent and Trademark Office for U.S. Appl. No. 12/891,543 dated Nov. 14, 2013 (14 pages).
Non-Final Office Action from the U.S. Patent and Trademark Office for U.S. Appl. No. 13/079,597 dated Jan. 11, 2012 (8 pages).
Examiner-Initiated Interview Summary from the U.S. Patent and Trademark Office for U.S. Appl. No. 13/171,081 dated Sep. 4, 2013 (1 page).
Applicant Summary of Interview of Examiner from the U.S. Patent and Trademark Office for U.S. Appl. No. 13/345,606 dated Oct. 21, 2013 (8 pages).
Summary of Interview from the U.S. Patent and Trademark Office for U.S. Appl. No. 13/345,606 dated Oct. 21, 2013 (1 page).
Notice of Allowance from the U.S. Patent and Trademark Office for U.S. Appl. No. 13/572,397 dated Jun. 29, 2015 (2 pages).
Examiner-Initiated Interview Summary from the U.S. Patent and Trademark Office for U.S. Appl. No. 13/768,765 dated Aug. 28, 2015 (1 page).
Advisory Action from the U.S. Patent and Trademark Office for U.S. Appl. No. 13/907,128 dated Dec. 13, 2013 (2 pages).
Advisory Action from the U.S. Patent and Trademark Office for U.S. Appl. No. 14/043,165 dated Jul. 9, 2015 (3 pages).
Patent Board Decision from the U.S. Patent and Trademark Office for U.S. Appl. No. 14/043,165 dated Dec. 20, 2017 (11 page).
Notice of Allowance from the U.S. Patent and Trademark Office for U.S. Appl. No. 14/043,165 dated Mar. 19, 2018 (11 pages).
Notice of Allowance from the U.S. Patent and Trademark Office for U.S. Appl. No. 14/043,165 dated Aug. 6, 2018 (11 pages).
Notice of Allowance from the U.S. Patent and Trademark Office for U.S. Appl. No. 14/095,123 dated Mar. 30, 2017 (10 pages).
Applicant-Initiated Interview Summary from the U.S. Patent and Trademark Office for U.S. Appl. No. 14/179,328 dated Dec. 11, 2014 (3 pages).
Notice of Allowance from the U.S. Patent and Trademark Office for U.S. Appl. No. 14/298,806 dated Apr. 12, 2017 (10 pages).
Applicant-Initiated Interview Summary from the U.S. Patent and Trademark Office for U.S. Appl. No. 14/540,830 dated Mar. 24, 2017 (3 pages).
Final Office Action from the U.S. Patent and Trademark Office for U.S. Appl. No. 14/540,830 dated May 15, 2017 (42 pages).
Applicant-Initiated Interview Summary from the U.S. Patent and Trademark Office for U.S. Appl. No. 14/540,830 dated Jul. 28, 2017 (3 page).
Notice of Allowance from the U.S. Patent and Trademark Office for U.S. Appl. No. 14/540,830 dated Aug. 15, 2017 (8 pages).
Non-Final Office Action from the U.S. Patent and Trademark Office for U.S. Appl. No. 14/792,210 dated Aug. 27, 2018 (53 pages).
Final Office Action from the U.S. Patent and Trademark Office for U.S. Appl. No. 14/792,210 dated Mar. 5, 2019 (17 pages).
Final Office Action from the U.S. Patent and Trademark Office for U.S. Appl. No. 15/140,351 dated Dec. 6, 2018 (21 pages).
Advisory Action from the U.S. Patent and Trademark Office for U.S. Appl. No. 15/140,351 dated Mar. 5, 2019 (4 pages).
Examiner-Initiated Interview Summary from the U.S. Patent and Trademark Office for U.S. Appl. No. 15/140,351 dated Mar. 5, 2019 (2 pages).
Applicant-Initiated Interview Summary from the U.S. Patent and Trademark Office for U.S. Appl. No. 15/140,351 dated Jul. 15, 2019 (3 pages).
Notice of Allowance from the U.S. Patent and Trademark Office for U.S. Appl. No. 15/140,351 dated Mar. 5, 2020 (16 pages).
Examiner-Initiated Interview Summary from the U.S. Patent and Trademark Office for U.S. Appl. No. 15/140,351 dated Mar. 5, 2020 (1 pages).
Examiner-Initiated Interview Summary from the U.S. Patent and Trademark Office for U.S. Appl. No. 15/163,600 dated Sep. 14, 2016 (1 page).
Non-Final Office Action from the U.S. Patent and Trademark Office for U.S. Appl. No. 15/188,819 dated Jul. 3, 2018 (7 pages).
Applicant-Initiated Interview Summary from the U.S. Patent and Trademark Office for U.S. Appl. No. 15/188,819 dated Sep. 24, 2018 (4 pages).
Notice of Allowance from the U.S. Patent and Trademark Office for U.S. Appl. No. 15/188,819 dated Jan. 25, 2019 (7 pages).
Notice of Allowance from the U.S. Patent and Trademark Office for U.S. Appl. No. 15/188,819 dated Mar. 15, 2019 (5 pages).
Notice of Allowance from the U.S. Patent and Trademark Office for U.S. Appl. No. 15/188,819 dated Aug. 21, 2019 (8 pages).
Notice of Allowance from the U.S. Patent and Trademark Office for U.S. Appl. No. 15/188,819 dated Oct. 2, 2019 (4 pages).
Notice of Allowance from the U.S. Patent and Trademark Office for U.S. Appl. No. 15/188,819 dated Jan. 24, 2020 (8 pages).
Notice of Allowance from the U.S. Patent and Trademark Office for U.S. Appl. No. 15/188,819 dated Mar. 20, 2020 (4 pages).
Non-Final Office Action from the U.S. Patent and Trademark Office for U.S. Appl. No. 15/188,872 dated Oct. 19, 2018 (12 pages).
Final Office Action from the U.S. Patent and Trademark Office for U.S. Appl. No. 15/188,872 dated May 8, 2019 (14 pages).
Applicant-Initiated Interview Summary from the U.S. Patent and Trademark Office for U.S. Appl. No. 15/188,872 dated Jul. 15, 2019 (4 pages).
Notice of Allowance from the U.S. Patent and Trademark Office for U.S. Appl. No. 15/188,872 dated Oct. 28, 2019 (5 pages).
Notice of Allowance from the U.S. Patent and Trademark Office for U.S. Appl. No. 15/188,872 dated Jan. 23, 2020 (9 pages).
Notice of Allowance from the U.S. Patent and Trademark Office for U.S. Appl. No. 15/188,872 dated Mar. 20, 2020 (5 pages).
Notice of Allowance from the U.S. Patent and Trademark Office for U.S. Appl. No. 15/254,627 dated Apr. 3, 2017 (11 pages).
Notice of Allowance from the U.S. Patent and Trademark Office for U.S. Appl. No. 15/254,627 dated Jul. 13, 2017 (4 pages).
Non-Final Office Action from the U.S. Patent and Trademark Office for U.S. Appl. No. 15/292,006 dated May 9, 2018 (17 pages).
Final Office Action from the U.S. Patent and Trademark Office for U.S. Appl. No. 15/292,006 dated Oct. 17, 2018 (18 pages).
Examiner-Initiated Interview Summary from the U.S. Patent and Trademark Office for U.S. Appl. No. 15/292,006 dated Nov. 29, 2018 (1 page).
Notice of Allowance from the U.S. Patent and Trademark Office for U.S. Appl. No. 15/292,006 dated Nov. 29, 2018 (12 pages).
Notice of Allowance from the U.S. Patent and Trademark Office for U.S. Appl. No. 15/292,006 dated Jan. 28, 2019 (3 pages).
Notice of Allowance from the U.S. Patent and Trademark Office for U.S. Appl. No. 15/292,006 dated Apr. 10, 2019 (6 pages).
Notice of Allowance from the U.S. Patent and Trademark Office for U.S. Appl. No. 15/292,006 dated Aug. 7, 2019 (6 pages).
Notice of Allowance from the U.S. Patent and Trademark Office for U.S. Appl. No. 15/292,006 dated Aug. 22, 2019 (3 pages).
Notice of Allowance from the U.S. Patent and Trademark Office for U.S. Appl. No. 15/292,006 dated Sep. 4, 2019 (7 pages).
Notice of Allowance from the U.S. Patent and Trademark Office for U.S. Appl. No. 15/292,006 dated Oct. 29, 2019 (6 pages).
Notice of Allowance from the U.S. Patent and Trademark Office for U.S. Appl. No. 15/292,006 dated Dec. 12, 2019 (3 pages).
Notice of Allowance for U.S. Appl. No. 15/292,006 dated Feb. 10, 2020 (3 pages).
Non-Final Office Action from the U.S. Patent and Trademark Office for U.S. Appl. No. 15/292,014 dated Jan. 24, 2019 (7 pages).

(56) References Cited

OTHER PUBLICATIONS

Notice of Allowance from the U.S. Patent and Trademark Office for U.S. Appl. No. 15/292,014 dated Jul. 11, 2019 (8 pages).
Notice of Allowance from the U.S. Patent and Trademark Office for U.S. Appl. No. 15/292,014 dated Nov. 15, 2019 (7 pages).
Notice of Allowance from the U.S. Patent and Trademark Office for U.S. Appl. No. 15/292,014 dated Dec. 5, 2019 (4 pages).
Notice of Allowance from the U.S. Patent and Trademark Office for U.S. Appl. No. 15/292,014 dated Jan. 8, 2020 (4 pages).
Notice of Allowance from the U.S. Patent and Trademark Office for U.S. Appl. No. 15/292,014 dated Jan. 23, 2020 (4 pages).
Notice of Allowance from the U.S. Patent and Trademark Office for U.S. Appl. No. 15/292,023 dated Apr. 11, 2017 (11 pages).
Non-Final Office Action from the U.S. Patent and Trademark Office for U.S. Appl. No. 15/346,530 dated Mar. 26, 2018 (12 pages).
Applicant-Initiated Interview Summary from the U.S. Patent and Trademark Office for U.S. Appl. No. 15/346,530 dated May 17, 2018 (3 pages).
Final Office Action from the U.S. Patent and Trademark Office for U.S. Appl. No. 15/346,530 dated Sep. 6, 2018 (14 pages).
Advisory Action from the U.S. Patent and Trademark Office for U.S. Appl. No. 15/346,530 dated Nov. 21, 2018 (4 pages).
Notice of Allowance from the U.S. Patent and Trademark Office for U.S. Appl. No. 15/346,530 dated May 15, 2019 (8 pages).
Notice of Allowance from the U.S. Patent and Trademark Office for U.S. Appl. No. 15/346,530 dated Aug. 27, 2019 (7 pages).
Notice of Allowance from the U.S. Patent and Trademark Office for U.S. Appl. No. 15/346,530 dated Oct. 9, 2019 (4 pages).
Notice of Allowance from the U.S. Patent and Trademark Office for U.S. Appl. No. 15/346,530 dated Dec. 17, 2019 (4 pages).
Bergstrom, Patrik. "Automated setup of display protocols" (2015).
Radcliffe, et al., "Comparison of Stereo Disc Photographs and Alternation Flicker Using a Novel Matching Technology for Detecting Glaucoma Progression", Ophthalmic Surgery, Lasers & Imaging, Jun. 9, 2010.
Sandberg et al., "Automatic detection and notification of "wrong patient-wrong location" errors in the operating room," Surgical Innovation, Sep. 2005, vol. 12, No. 3, pp. 253-260.
Syed, et al., "Automated alternation flicker for the detection of optic disc haemorrhages", ACTA Ophthalmologica 2012, accepted for publication on Nov. 26, 2010.
Syed, et al., "Detection of Progressive Glaucomatous Optic Neuropathy Using Automated Alternation Flicker With Stereophotography," Research Letter, Arch Ophthalmol., published online Dec. 13, 2010. 2010 American Medical Association.
Tay, et al., "Assessing Signal Intensity Change on Well-registered Images: Comparing Subtraction, Color-encoded Subtraction, and Parallel Display Formats", Original Research: Computer Applications Radiology, vol. 260: No. 2—Aug. 2011.
VanderBeek, et al., "Comparing the detection and agreement of parapapillary atrophy progression using digital optic disk photographs and alternation flicker", Glaucoma, Graefes Arch Clin Exp Ophthalmol (2010) 248:1313-1317, Apr. 15, 2010.
Notice of Allowance from the U.S. Patent and Trademark Office for U.S. Appl. No. 15/140,351 dated Sep. 22, 2020 (8 pages).
Notice of Allowance from the U.S. Patent and Trademark Office for U.S. Appl. No. 15/140,351 dated Oct. 19, 2020 (2 pages).

* cited by examiner

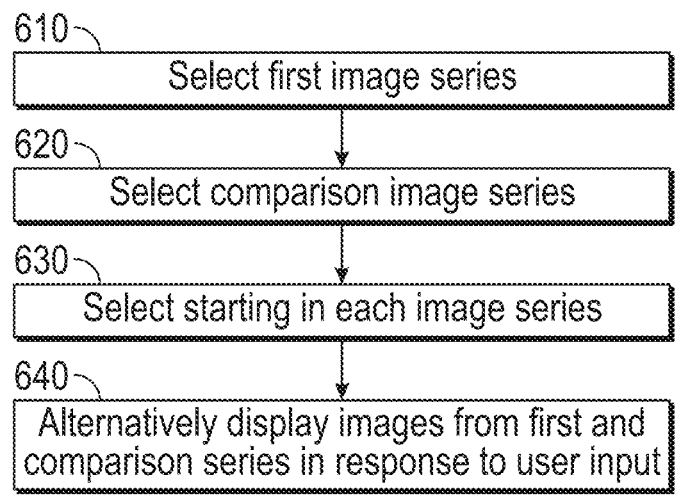
FIG. 6
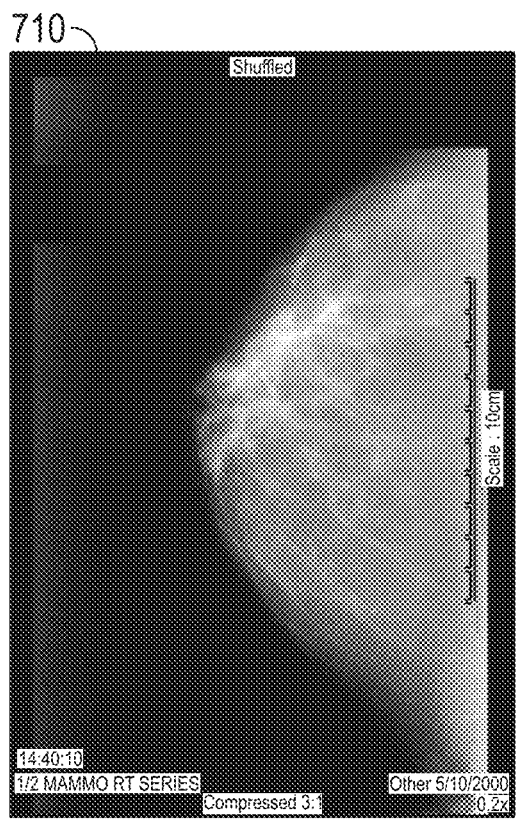 
FIG. 7A  FIG. 7B

Example Series to be Sorted

| Series | Attributes | Images in Series |
|---|---|---|
| Series A (from Exam I) | Date: 2012-10-01<br>Modality: Dual-Energy X-Ray<br>View Type: Traditional View | A1,A2,A3 |
| Series B (from Exam I) | Date: 2012-10-01<br>Modality: Dual-Energy X-Ray<br>View Type: Bones Out View | B1,B2,B3 |
| Series C (from Exam II) | Date: 2013-01-20<br>Modality: Dual-Energy X-Ray<br>View Type: Traditional View | C1,C2,C3 |
| Series D (from Exam II) | Date: 2013-01-20<br>Modality: Dual-Energy X-Ray<br>View Type: Bones Out View | D1,D2,D3 |

FIG.15B

DATABASE SYSTEMS AND INTERACTIVE USER INTERFACES FOR DYNAMIC INTERACTION WITH, AND INDICATIONS OF, DIGITAL MEDICAL IMAGE DATA

CROSS-REFERENCE TO RELATED APPLICATIONS

Any and all applications for which a foreign or domestic priority claim is identified in the Application Data Sheet as filed with the present application are hereby incorporated by reference under 37 CFR 1.57.

This application claims benefit of U.S. Provisional Patent Application No. 62/155,362, filed Apr. 30, 2015, and titled "SYSTEMS AND USER INTERFACES FOR DYNAMIC INTERACTION WITH, AND COMPARISON OF, MEDICAL IMAGE DATA," and also claims benefit of U.S. Provisional Patent Application No. 62/171,866, filed Jun. 5, 2015, and titled "SYSTEMS AND USER INTERFACES FOR DYNAMIC INTERACTION WITH, AND COMPARISON OF, MEDICAL IMAGE DATA."

This application is also related to U.S. patent application Ser. No. 15/140,346, filed on Apr. 27, 2016, and titled "DATABASE SYSTEMS AND INTERACTIVE USER INTERFACES FOR DYNAMIC INTERACTION WITH, AND SORTING OF, DIGITAL MEDICAL IMAGE DATA," U.S. patent application Ser. No. 15/140,363, filed on Apr. 27, 2016, and titled "DATABASE SYSTEMS AND INTERACTIVE USER INTERFACES FOR DYNAMIC INTERACTION WITH, AND COMPARISON OF, DIGITAL MEDICAL IMAGE DATA," U.S. patent application Ser. No. 15/140,351, filed on Apr. 27, 2016, and titled "DATABASE SYSTEMS AND INTERACTIVE USER INTERFACES FOR DYNAMIC INTERACTION WITH, AND REVIEW OF, DIGITAL MEDICAL IMAGE DATA."

The entire disclosure of each of the above items is hereby made part of this specification as if set forth fully herein and incorporated by reference for all purposes, for all that it contains.

TECHNICAL FIELD

Embodiments of the present disclosure relate to systems and techniques for accessing one or more databases and providing user interfaces for dynamic interactions with digital medical image data.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Medical images are typically viewed by radiologists and other physicians, patients, and/or others by interaction with desktop computer systems with stationary monitors. When comparison of related images is required, subtle differences between images may be difficult to detect. For example, if a lung radiograph from two months previous, and a current lung radiograph are to be compared in order to determine if any changes have occurred in the lungs over the previous two months, the viewer or reader typically views the two x-rays side by side. For example, the viewer or reader may have two monitors placed side by side, wherein each of the monitors displays a chest radiographic image. Alternatively, the viewer may view the two images side by side on a single monitor. However, as those of skill in the art will recognize, identifying differences in related images in this manner is often tedious and difficult. Some imaging modalities, such as CT and MRI, produce a large number of images, hundreds to even thousands of images per exam. In many cases, comparison of different series of images within the exam is required. For example, comparison of pre and post contrast images to detect areas of enhancement or comparison of PET and CT images for localization of activity is often necessary. Further, these often large exams may need to be compared to multiple prior exams to detect subtle, progressive changes over time, for example to detect a small, growing tumor.

SUMMARY

The systems, methods, and devices described herein each have several aspects, no single one of which is solely responsible for its desirable attributes. Without limiting the scope of this disclosure, several non-limiting features will now be described briefly.

Embodiments of the present disclosure relate to database systems and techniques for accessing data stores of medical images and displaying the medical images to efficiently provide information in an interactive user interface. Previous systems for display of, and interaction with, image data were typically inefficient at enabling detection of differences between images and evaluation of images. Disclosed herein are systems that, according to various embodiments, advantageously provide highly efficient, intuitive, and rapid dynamic interaction with medical images (including two-dimensional images and images rendered from three-dimensional image data) to enable detection of differences between related medical images and evaluation of medical images. The systems may include interactive user interfaces that are dynamically updated to provide rapid comparison of images. Further, images from multiple series and/or exams, and/or images from other sources, may be automatically sorted (e.g., in one embodiment, interleaved) by the system according to attributes associated with the images and rules and/or preferences of the user.

In an embodiment, the user may select an image from a series of a first exam, and the system automatically determines and displays one or more comparison images from another image series and/or exams. Images selected for comparison, and/or images that are sorted, may additionally be automatically registered and/or matched to enable more efficient comparison and evaluation by the user. Accordingly, a user may use the systems described herein to more quickly, thoroughly, and efficiently interact with medical images, as compared to previous systems. The features and advantages noted above, as well as others, are discussed in further detail below.

In various embodiments, systems and methods are disclosed for matching related medical images and/or medical image series from multiple exams, automatically displaying medical images in particular arrangements, and automatically sorting medical images from related exams. In one example, a user selects a medical image, and the system automatically identifies related images and/or medical image series from 2, 3, or 4 (or more) other exams and displays the images next to one another in a grid arrangement, and/or sorts the images and displays them sequentially in an image pane.

Accordingly, in various embodiments, large amounts of data are automatically and dynamically calculated interactively in response to user inputs, and the calculated data is efficiently and compactly presented to a user by the system. Thus, in some embodiments, the user interfaces described herein are more efficient as compared to previous user interfaces in which data is not dynamically updated and compactly and efficiently presented to the user in response to interactive inputs.

Further, as described herein, the system may be configured and/or designed to generate user interface data useable for rendering the various interactive user interfaces described. The user interface data may be used by the system, and/or another computer system, device, and/or software program (for example, a browser program), to render the interactive user interfaces. The interactive user interfaces may be displayed on, for example, electronic displays (including, for example, touch-enabled displays).

It has been noted that design of computer user interfaces "that are useable and easily learned by humans is a non-trivial problem for software developers." (Dillon, A. (2003) User Interface Design. MacMillan Encyclopedia of Cognitive Science, Vol. 4, London: MacMillan, 453-458.) The present disclosure describes various embodiments of interactive and dynamic user interfaces that are the result of significant development. This non-trivial development has resulted in the user interfaces described herein which may provide significant cognitive and ergonomic efficiencies and advantages over previous systems. The interactive and dynamic user interfaces include improved human-computer interactions that may provide reduced mental workloads, improved decision-making, reduced work stress, and/or the like, for a user. For example, user interaction with the interactive user interface via the inputs described herein may provide an optimized display of, and interaction with, image data (including medical images) and may enable a user to more quickly and accurately access, navigate, assess, and digest the image data than previous systems.

Further, the interactive and dynamic user interfaces described herein are enabled by innovations in efficient interactions between the user interfaces and underlying systems and components. For example, disclosed herein are improved methods of receiving user inputs (including methods of interacting with, and selecting, images), translation and delivery of those inputs to various system components, automatic and dynamic execution of complex processes in response to the input delivery, automatic interaction among various components and processes of the system, and automatic and dynamic updating of the user interfaces (to, for example, display the relevant medical images). The interactions and presentation of data via the interactive user interfaces described herein may accordingly provide cognitive and ergonomic efficiencies and advantages over previous systems.

Various embodiments of the present disclosure provide improvements to various technologies and technological fields. For example, as described above, existing medical image interaction technology (including, e.g., Picture Archiving and Communication Systems, Electronic Medical Record Systems, and/or the like) is limited in various ways (e.g., image review is slow and cumbersome, comparison of images is inefficient, etc.), and various embodiments of the disclosure provide significant improvements over such technology. Additionally, various embodiments of the present disclosure are inextricably tied to computer technology. In particular, various embodiments rely on detection of user inputs via graphical user interfaces, calculation of updates to displayed electronic data based on those user inputs, automatic processing of related electronic medical images, and presentation of the updates to displayed medical images via interactive graphical user interfaces. Such features and others (e.g., generation of 2D medical images from a 3D imaging volume and/or other 2D images, such as at automatically selected or user-selected planes) are intimately tied to, and enabled by, computer technology, and would not exist except for computer technology. For example, the interactions with displayed data described below in reference to various embodiments cannot reasonably be performed by humans alone, without the computer technology upon which they are implemented. Further, the implementation of the various embodiments of the present disclosure via computer technology enables many of the advantages described herein, including more efficient interaction with, and presentation of, various types of electronic image data.

The inventors have found that users using the system to flip through medical images (e.g., to analyze the images and perform diagnoses based on the images) are faster (e.g., 15% faster or more) and more accurate than users using traditional methods of comparing images.

In an embodiment, a method of viewing medical images from two or more image series on a display device coupled to a computing device comprises the actions of selecting a first image series comprising two or more medical images, selecting at least one comparison image series, each of the comparison image series comprising two or more medical images, interleaving images of the first image series and the comparison image series in order to form an interleaved image series, and sequentially displaying the images of the interleaved image series at a single location on the display device.

In another embodiment, a method of viewing a series of medical images on a display device coupled to a computing device comprises the actions of (a) selecting a first image series for viewing, the first image series comprising a plurality X of medical images, (b) selecting a second image series for viewing, the second image series comprising a plurality Y of medical images, (c) displaying at a predetermined location on the display device a Nth image of the first image series, (d) replacing the Nth image of the first image series with a Mth image of the second image series at the predetermined location, (e) incrementing N and M, and (f) repeating steps (c) to (f).

In yet another embodiment, a system for enhancing a viewer's ability to detect differences between medical images in two or more sets of medical images comprises a display device, a graphical user interface displayed on the display device and comprising an image pane configured to display a single medical image at a time, an image selection module to select two or more sets of medical images, each of the sets of medical images comprising two or more medical images, and a user interface to receive commands from a user, wherein in response to receiving a first command from the user, the image pane sequentially displays a first medical image from each of the image sets and, after displaying the first medical image from each image set, the image pane sequentially displays a second medical image from each image set. This process of displaying images from images series alternatively continues through subsequent images in the image series.

In another embodiment, a system of viewing medical images from two or more image series on a display device coupled to a computing device comprises means for selecting a first image series comprising two or more medical images, means for selecting at least one comparison image series, each of the comparison image series comprising two or more medical images, means for interleaving images of the first image series and the comparison image series in order to form an interleaved image series, and means for sequentially displaying the images of the interleaved image series at a single location on the display device.

In yet another embodiment, a method of forming an interleaved image series comprises selecting N groups of images, each of the groups of images comprising two or more images, determining a starting image of each of the groups of images, creating an interleaved image series comprising images from each of the selected N groups of images, wherein the images of the interleaved image series are ordered so that an image from each of the N groups of images is included in each sequential Nth group of images, and providing the interleaved image series to a user interface for sequential display in a predetermined location of a display device.

In another embodiment, a method of viewing medical images from two or more image series on a display device comprises: selecting a first image series comprising two or more medical images of a first portion of a human anatomy; selecting at least one comparison image series, each of the comparison image series comprising two or more medical images of the first portion of the human anatomy; interleaving images of the first image series and the comparison image series in order to form an interleaved image series such that the interleaved images series is ordered to include a single image of each of the comparison images series after each single image of the first image series; and sequentially displaying the images of the interleaved image series at a single location on the display device, wherein the method is performed by a computing system comprising one or more computing devices.

According to an aspect, the single location on the display device comprises a comparison pane.

According to another aspect, the method further comprises selecting a starting image in one or more of the first and comparison image series, wherein the starting images indicate respective first images from the one or more first and comparison image series that are to be included in the interleaved image series.

According to yet another aspect, selecting the at least one comparison image series is performed by the computing device based on predefined comparison rules.

According to another aspect, the predefined comparison rules indicate that image series with substantially the same name as a name of the first image series are selected for comparison with the first image series.

According to yet another aspect, the method further comprises: displaying a list of image series identifiers associated with one or more image series that satisfy the comparison rules; and selecting one or more of the image series identifiers, wherein the image series associated with the selected image series identifiers are selected as comparison image series.

According to another aspect, the sequentially displaying is controlled by an input device coupled to the computing device so that when a predetermined input is received by the computing device, the image displayed at the single location is replaced by an adjacent image in the interleaved image series.

According to yet another aspect, the predetermined input comprises moving a scroll bar on a mouse.

According to another aspect, the method further comprises displaying information regarding the medical image currently displayed at the single location.

According to yet another aspect, the method further comprises selecting a zoom level for each of the medical images in the first image series by adjusting a zoom level on one of the medical images of the first image series.

According to another aspect, the method further comprises selecting an image characteristic of the images in the first image series by adjusting the image characteristic on one of the medical images of the first image series.

According to yet another aspect, the method further comprises selecting a zoom level for each of the images in the comparison image series by adjusting a zoom level on one of the medical images of the respective comparison image series.

According to another aspect, the method further comprises automatically selecting an image characteristic of the images in the first image series according to differences in the image characteristics of the images detected by the computing device.

In yet another embodiment, a method of viewing a series of medical images on a display device comprises: (a) selecting a first image series for viewing, the first image series comprising a plurality X of medical images; (b) selecting a second image series for viewing, the second image series comprising a plurality Y of medical images; (c) displaying at a predetermined location on the display device a Nth image of the first image series; (d) replacing the Nth image of the first image series with a Mth image of the second image series at the predetermined location; (e) incrementing or decrementing N and M; and (f) repeating steps (c) to (f), wherein the method is performed by a computing system comprising one or more computing devices.

According to an aspect, the method further comprises displaying a user interface on the display device, wherein the predetermined location comprises a comparison pane within the user interface.

According to another aspect, the values of N and M are selected by a user of the computing device.

According to yet another aspect, the medical images comprise at least one of X-ray, mammogram, MRI, radiograph, computed tomography, magnetic resonance imaging, Ultrasound, positron emission tomography scan, angiogram, and nuclear scan images.

According to another aspect, the method further comprises: selecting a third image series for viewing, the third image series comprising a plurality Z of medical images; replacing the Mth image of the second image series with a Lth image of the third image series at the predetermined location; and incrementing or decrementing L.

According to yet another aspect, timing of the actions of displaying and replacing is controlled by an input device to the computing system, wherein the user may determine a speed at which images from the first and second image series are alternatively displayed at the predetermined location using the input device.

According to another aspect, the input device comprises at least one of: a mouse, a trackball, and a keyboard.

In another embodiment, a computerized method comprises: transmitting from a computing device to a display device data associated with two or more image panes, each depicting an image from a respective image series; receiving at the computing device selections of at least two image panes from an input device, in response to said receiving, interleaving by the computing device the images of the image series associated with the selected at least two selected image panes in order to form an interleaved image series; and initiating by the computing device display of an image of the interleaved image series in a comparison pane on the display device.

According to an aspect, a user of the computing device selects the image panes by clicking a mouse button after moving a pointer onto each of the image panes.

According to another aspect, a user of the computing device selects the image panes by clicking a mouse button after moving a pointer onto a border between the image panes.

According to yet another aspect, the comparison pane covers substantially all of a display area of the display device.

According to another aspect, the comparison pane is sized substantially equal to a size of the image panes.

According to yet another aspect, the displaying action comprises displaying from 2 to 40 image panes.

In yet another embodiment, a method of viewing medical images from two or more image series on a display device coupled to a computing device, wherein the method is performed by the computing device comprises: automatically selecting at least two comparison image series based on predefined user rules; interleaving images of the at least two comparison image series in order to form an interleaved image series; and sequentially displaying the images of the interleaved image series in a comparison pane on the display device.

According to an aspect, the user rules define criteria for selecting image series for comparison.

According to another aspect, the user rules include criteria related to DICOM header file information associated with medical images, wherein comparison image series are selected according to DICOM header file information.

In yet another embodiment, a method of viewing medical images from two or more image series on a display device, wherein the method is performed by a computing system comprising one or more computing devices comprises: selecting a first image series comprising two or more medical images; selecting at least one comparison image series, each of the comparison image series comprising two or more medical images; interleaving images of the first image series and the comparison image series in order to form two or more interleaved image series; and sequentially displaying the images of each of the interleaved image series in corresponding two or more comparison panes that are concurrently displayed on the display device.

According to an aspect, images in each respective interleaved image series are each of a particular projection so that a first interleaved image series comprises images of a first projection and a second interleaved image series comprises images of a second projection.

In another embodiment, a computing system comprises: an electronic display device; an input device; a non-transitory computer-readable storage medium configured to store software instructions; and one or more computing devices in communication with the electronic display device, the input device, and the non-transitory computer-readable medium, the one or more computing devices configured to execute the software instructions in order to: receive, at the computing system, a selection of a first image series comprising two or more medical images; receive, at the computing system, a selection of a second image series comprising two or more medical images obtained at a different time than the first image series; determine a first medical image of the first image series and a second medical image of the second image series that depict a same anatomical position; display the first medical image of the first image series at a first position on the electronic display device of the computing system; and in response to receiving a first command from a user of the computing system via the input device, replace at the same first position on the display the first medical image with the second medical image of the second image series; and in response to receiving a second command from the user of the computing device via the input device, replace the second medical image with the first medical image.

According to an aspect, the first medical image of the first image series is not an initial image of the first image series and/or the second medical image of the second image series is not an initial image of the second image series.

According to another aspect, the first command is triggered in response to input from one or more of a keyboard, a mouse, or a touchpad.

According to yet another aspect, the computing system further comprises: wherein the first command is triggered by the user pressing a button of a mouse or other input device and the second command is triggered by the user releasing the button.

In yet another embodiment, a method comprises: receiving, at a computing device, a selection of a first image series comprising two or more medical images; receiving, at the computing device, a selection of a second image series comprising two or more medical images obtained at a different time than the first image series; displaying a first medical image of the first image series at a first position on a display device of the computing device; in response to receiving a first command from a user of the computing device via an input device, replacing at the same first position on the display, by the computing device, the first medical image with a second medical image of the second image series; and in response to receiving a second command from the user of the computing device via the input device, replacing the second medical image with the first medical image, wherein the first command is triggered by the user moving a scroll wheel of a mouse or other input device in a first direction and the second command is triggered by the user moving the scroll wheel in a second direction that is opposite the first direction.

According to an aspect, the first image series is acquired at a first time associated with a first exam of a patient and the second image series is acquired at a later time associated with a second exam of the patient.

According to another aspect, the first images series and the second image series are related so that when images of the image series are compared, meaningful distinctions may be detected.

According to yet another aspect, the first image series and second image series are acquired using a common type of imaging device.

According to another aspect, the first image series and second image series are acquired using different types of imaging devices.

In another embodiment, a method comprises: displaying, by a computing device comprising hardware, a medical image of a first image series at a first position on a display device of the computing device; in response to receiving a first command from a user of the computing device via an input device, replacing, by the computing device, the medical image of the first image series acquired during a first time period with a comparison medical image of a second image series acquired during a second time period different than the first time period; and in response to receiving a second command from the user via the input device, replacing, by the computing device, the comparison medical image of the second image series with the medical image of the first image series, wherein the first command is triggered by the user moving a scroll wheel of the input device in a first direction and the second command is triggered by the user moving the scroll wheel in a second direction that is opposite the first direction.

According to an aspect, at least one of the first image series or the second image series is automatically selected by the computing device.

According to another aspect, at least one of the first image series or the second image series is automatically selected based on DICOM header information associated with the image series.

According to yet another aspect, at least one of the first image series or the second image series is automatically selected based on filenames associated with the image series.

According to another aspect, the comparison medical image is selected from a plurality of images in the second image series such that the comparison image and the medical image of the first image series depict the same anatomical position.

According to yet another aspect, the computing device automatically selects the comparison medical image.

According to another aspect, the computing device receives an indication of one or more of the medical image and/or the comparison medical image from the user of the computing device.

According to yet another aspect, a first value associated with a first image characteristic of the medical images of the first image series is different than a second value associated with the first image characteristic of the second image series.

According to another aspect, the first image characteristic comprises one or more of size, rotation, location, zoom level, cropping, or color characteristics.

According to yet another aspect, the first value associated with the first image characteristic of the first image series or the second value associated with the first image characteristic of the second image series is automatically adjusted such that the first value and the second value are equivalent.

According to another aspect, the method further comprises receiving input from the user indicating adjustments to at least a centering and a window level of one or more of the medical image of the first image series or the comparison medical image of the second image series.

According to yet another aspect, one or more values associated with image characteristics of the comparison medical image are adjusted in response to user input via the input device.

According to another aspect, the one or more values associated with the image characteristics that are adjusted for the comparison medical image are applied to at least some other images of the second image series.

According to yet another aspect, one or more values associated with image characteristics of images of the first and/or second image series are automatically adjusted so that similar anatomical features depicted in images of the first and second image series are aligned.

According to another aspect, the first command comprises positioning a cursor near a border between the first medical image of the first image series and the second medical image of the second image series.

In yet another embodiment, a non-transitory computer-readable medium storing software code is disclosed that is configured for execution by a computing system in order to cause the computing system to perform operations including: displaying a medical image of a first image series at a first position on a display device of the computing device; displaying a medical image of a second image series at a second position on the display device, wherein the first image series and the second image series were obtained at different times; in response to receiving a first command from a user of the computing device via an input device: replacing the medical image of the first image series with a comparison medical image of a third image series; and replacing the medical image of the second image series with a comparison medical image of a fourth image series; and in response to receiving a second command from the user via the input device: replacing the comparison medical image of the third image series with the medical image of the first image series; and replacing the comparison medical image of the fourth image series with the medical image of the second image series, wherein the first command is triggered by the user moving a scroll wheel of the input device in a first direction and the second command triggered by the user moving the scroll wheel in a second direction that is opposite the first direction.

According to an aspect, the software code is further configured for execution in order to cause the computing system to perform operations including: selecting the first and third image series for comparison based on one or more similarities in DICOM information of files associated with the first and third image series.

According to another aspect, the first medical image and the second medical image are each of a same modality such that differences between the first medical image and the second medical image are detectable by the user viewing the replacement of the first medical image by the second medical image.

According to yet another aspect, the first image series is acquired at a first time associated with a first exam of a patient and the second image series is acquired at a later time associated with a second exam of the patient.

According to another aspect, the one or more computing devices are further configured to execute the software instructions in order to: automatically adjust one or more characteristics of the first medical image and/or the second medical image such that common anatomical features shown in each of the first and second medical images are aligned.

According to yet another aspect, the first medical image of the first image series is not an initial image of the first image series and/or the second medical image of the second image series is not an initial image of the second image series.

According to another aspect, the method further comprises: automatically adjusting, by the computing device, a value associated with a particular characteristic of each of the first medical image and the second medical image such that the values are equivalent.

In another embodiment, a computing system comprises: a display device configured to render images for viewing by one or more users; an input device configured to receive input from a user of the computing system; one or more hardware processors configured to execute software code in order to direct display of images on the display device; and a module comprising software code stored on one or more non-transitory computer readable mediums, the software code configured for execution by the one or more processors in order to: determine an image of a first image series and a comparison image of a second image series that depict a same anatomical position; cause the display device to display the image of the first image series at a first position; and in response to detecting a predetermined input from the user of the computing device via the input device, cause the display device to replace the image of the first image series with the comparison image of the second image series, wherein images of the first image series and images of the second image series were generated by imaging equipment at different times, on different dates, and/or during different time periods.

In yet another embodiment, a non-transitory computer readable medium storing software code configured for execution by a computing system in order to cause the computing system to perform operations is disclosed, the software code comprising: a first module configured to receive input from a user of the computing system via one or more input devices and to detect a predetermined input from the user; a second module configured to: determine an image of a first image series and a comparison image of a second image series that depict a same anatomical position; cause a display device of the computing system to display the image of the first image series at a first position on the display device; and in response to the first module detecting the predetermined input, cause the display device of the computing system to replace the image of the first image series with the comparison image of the second image series, wherein the first image series and the second image series were originally generated at different times, on different dates, and/or during different time periods.

In another embodiment, a method comprises: receiving, at a computing system, at least a first plurality of images comprising a first image series and a second plurality of images comprising a second image series, wherein the first plurality of images and the second plurality of images together comprise a set of images; determining, by the computing system, at least a first characteristic associated with each of the images of the set of images; determining, by the computing system, at least a second characteristic associated with each of the images of the set of images; determining, by the computing system, an ordering of the images of the set of images based on: first: values of the first characteristic associated with respective images, and second: values of the second characteristic associated with respective images; displaying at a location of a display a first image of the set of images that is first in the determined ordering of the images; and in response to input from a user of the computing system indicating a direction of movement within the set of images, replacing the first image or other image displayed at the same location of the display with another image that is adjacent to the first image or other image displayed at the same location of the display based on the determined ordering of the images.

According to an aspect, the first characteristic comprises a DICOM header information item.

According to another aspect, the first characteristic comprises at least one of a type of image, an area imaged, a clinical indication, a source of image, a display device, or a user.

According to yet another aspect, the first characteristic comprises at least one of brightness, contrast, size, opacity map, rotation, location, zoom level, cropping, morphing, or color.

According to another aspect, the first characteristic comprises an anatomical position depicted by the image.

According to yet another aspect, the second characteristic comprises a time at which the image was obtained.

According to another aspect, the first characteristic comprises at least one of a modality or an application of contrast agent.

According to yet another aspect, the second characteristic comprises a time at which the image was obtained.

According to another aspect, the method further comprises: automatically adjusting, by the computing system, at least one characteristic associated with the first image of the set of images such that the first image is better aligned with the second image of the set of images.

According to yet another aspect, the first and second images are adjacent to one another in the ordering of the images.

According to another aspect, an image characteristic of the second image is adjusted such that the information displayed in the first image and the second image more closely matches, and differences between the first image and the second medical image are more easily detectable by the user.

According to yet another aspect, the image characteristic comprises at least one of brightness, contrast, size, opacity map, rotation, location, zoom level, cropping, morphing, or color.

According to another aspect, the computing system is configured to provide the input in response to the user moving a scroll wheel of a mouse or other input device in a first direction.

According to yet another aspect, the method further comprises: in response to a second input from the user of the computing system indicating an opposite direction of movement within the set of images, replacing the second image displayed at the same location of the display with the first image or other image that is adjacent to the second image at the same location of the display based on the determined ordering of the images.

According to another aspect, the computing system is configured to provide the input in response to the user moving a scroll wheel of a mouse or other input device in a first direction.

According to yet another aspect, the computing system is configured to provide the second input in response to the user moving a scroll wheel of a mouse or other input device in a second direction.

According to another aspect, the method further comprises: determining, by the computing system, a first characteristic associated with the first image series; identifying, by the computing system, the second image series for comparison with the first image series, wherein the second image series is identified based on the second image series being associated with a second characteristic have a same value as the first characteristic of the first image series.

According to yet another aspect, the first and second characteristics comprise at least one of DICOM header information items, filenames, or modalities.

In yet another embodiment, a computing system comprises: an electronic display; an input device; a non-transitory computer-readable storage medium configured to store software instructions; and one or more computer processors in communication with the electronic display, the input device, and the non-transitory computer-readable medium, the one or more computer processors configured to execute the software instructions in order to cause the computing system to: receive at least a first plurality of images comprising a first image series and a second plurality of images comprising a second image series, wherein the first plurality of images and the second plurality of images together comprise a set of images; determine at least a first characteristic associated with each of the images of the set of images; determine at least a second characteristic associated with each of the images of the set of images; determine an ordering of the images of the set of images based on: first: values of the first characteristic associated with respective images, and second: values of the second characteristic associated with respective images; display at a location of a display a first image of the set of images that is first in the determined ordering of the images; and in response to input from a user of the computing system indicating a direction of movement within the set of images, replace the first image or other image displayed at the same location of the display with another image that is adjacent to the first image or other image displayed at the same location of the display based on the determined ordering of the images.

Another embodiment comprises a method of displaying medical data. The method comprises receiving a plurality of medical images of a first medical examination and receiving at least one user-defined matching rules, at least one of user-defined matching rules identifying selection criteria for the medical images. The method also comprises selecting medical images that satisfy the selection criteria of the user-defined rules, thereby matching medical images according to user-specific rules and receiving at least one user-defined display rule, at least one of user-defined display rules identifying a display preference with respect to selected medical images. The method also comprises displaying the selected medical images according to the identified display preferences, thereby allowing matched medical images to be visually compared and displayed in a manner that is suitable to the user's preferences.

Yet another embodiment comprises a method displaying medical data. The method comprises receiving a plurality of medical images of a first medical examination and receiving a plurality of medical images of a second medical examination. The method also comprises receiving at least one user-defined matching rule, at least one of user-defined matching rules identifying selection criteria for matching the medical images of the first and second medical examinations. The method also comprises selecting medical images that satisfy the selection criteria of the user-defined rules, thereby matching medical images of the first medical examination with medical images of the second examination according to user-specific rules. The method also comprises receiving a plurality of user-defined display rules, at least one of user-defined display rules identifying a display preference with respect to selected medical images. The method also comprises displaying the selected medical images according to the identified display preferences, thereby allowing matched medical images to be visually compared and displayed in a manner that is suitable to the user's preferences.

Another embodiment comprises a system for displaying medical data. The system comprises an electronic device being configured to receive a plurality of medical images of a first medical examination. The electronic device is configured to receive a plurality of user-defined matching rules. At least one of user-defined matching rules identify selection criteria for the medical images. The electronic device is further configured to select medical images that satisfy the selection criteria of the user-defined rules, thereby matching medical images according to user-specific rules. The electronic device is further configured to receive at least one user-defined display rules. At least one of user-defined display rules identify a display preference with respect to selected medical images. The electronic device is further being configured to display the selected medical images according to the identified display preferences, thereby allowing matched medical images to be visually compared and displayed in a manner that is suitable to the user's preferences.

In yet another embodiment, a method of displaying medical data comprises: receiving a plurality of medical images of a first medical examination; receiving a plurality of medical images of a second medical examination; receiving at least one user-defined matching rule, at least one of the user-defined matching rules identifying selection criteria for matching the medical images of the first and second medical examinations; selecting medical images that satisfy the selection criteria of the user-defined rules, thereby matching medical images of the first medical examination with medical images of the second medical examination according to the user-defined matching rules; receiving a plurality of user-defined display rules, at least one of user-defined display rules identifying one or more display preference with respect to selected medical images; and displaying the selected medical images according to the one or more identified display preference, thereby allowing matched medical images to be visually displayed in a manner that is suitable to the user's preferences, wherein at least some of the method is performed by a computing system comprising one or more computing device.

According to an aspect, the medical images of the first medical examination and of the second medical examination are each grouped in one or more image series.

According to another aspect, the method additionally comprises naming the matched medical images according to at least one user-defined naming rule.

According to yet another aspect, the method additionally comprises naming the medical images according to at least one user-defined naming rule prior to the selecting action.

In another embodiment, a system comprises: an electronic device configured to receive a plurality of medical images of a first medical examination, the electronic device being further configured to receive a plurality of medical images of a second medical examination, the electronic device being further configured to receive a plurality of user-defined matching rules, at least one of user-defined matching rules identifying selection criteria for matching the medical images of the first and second medical examinations, the electronic device being further configured to select medical images that satisfy the selection criteria of the user-defined rules, thereby matching medical images of the first medical examination with medical images of the second medical examination according to the user-defined matching rules, the electronic device being further configured to receive a plurality of user-defined display rules, at least one of the user-defined display rules identifying a display preference with respect to selected medical images, and the electronic device being further configured to display the selected medical images according to the identified display preference, thereby allowing matched medical images to be visually displayed in a manner that is suitable to the user's preferences.

According to an aspect, the medical images of the first medical examination and of the second medical examination are each grouped in one or more image series.

In yet another embodiment, a method of displaying medical data comprises: receiving a plurality of medical images of a first medical examination; receiving at least one user-defined matching rule including at least one user-defined matching rule identifying selection criteria for selecting medical images; selecting medical images that satisfy the selection criteria of the user-defined matching rules, thereby matching medical images according to user-specific rules; receiving at least one user-defined display rule including at least one user-defined display rule identifying a display preference with respect to the selected medical images; and displaying the selected medical images according to the identified display preference, thereby allowing the matched medical images to be visually compared and displayed in a manner that is suitable to user preferences, wherein at least some of the actions are performed by a computer system having one or more processors.

According to an aspect, the method additionally comprises naming the matched medical images according to at least one user-defined naming rule.

According to another aspect, the method additionally comprises naming the medical images according to at least one user-defined naming rule prior to said selecting.

According to yet another aspect, the medical images are grouped in one or more image series.

According to another aspect, the method additionally comprises: receiving a second plurality of medical images of a second medical examination; and selecting medical images of the first medical examination and the second medical examination that satisfy the selection criteria of the user-defined rules, thereby allowing a user to match medical images of the first medical examination with medical images of the second medical examination according to user-specific rules.

According to yet another aspect, the method additionally comprises: receiving at least one second user-defined display rule, the second user-defined display rule identifying a display preference with respect to matched medical images of the first and second examinations; and displaying the matched medical images in accordance with the second user-defined display rules.

According to another aspect, the method additionally comprises displaying the matched medical images in accordance with the user-defined display rules.

According to yet another aspect, the method additionally comprises: receiving a plurality of second user-defined matching rules, at least one of the user-defined matching rules identifying second selection criteria for matching the selected medical images of the first examination with medical images of a second medical examination; and selecting medical images of the first medical examination and the second medical examination that satisfy the second selection criteria of the user-defined rules, thereby allowing a user to match medical images of the first medical examination with medical images of the second medical examination according to user-specific rules.

According to another aspect, the method additionally comprises: receiving a plurality of second user-defined display rules, at least one of the second user-defined display rules identifying a display preference with respect to matched medical images of the first and second examinations; and displaying the matched medical images in accordance with the second user-defined display rules.

According to yet another aspect, the method additionally comprises displaying the matched medical images in accordance with the user-defined display rules.

In yet another embodiment, a system for displaying medical data comprises: an electronic device configured to receive a plurality of medical images of a first medical examination, the electronic device being further configured to receive a plurality of user-defined matching rules, at least one of the user-defined matching rules identifying selection criteria, the electronic device being further configured to select medical images that satisfy the selection criteria of the user-defined matching rules, thereby matching medical images according to user-specific rules, the electronic device being further configured to receive a plurality of user-defined display rules, at least one of the user-defined display rules identifying a display preference with respect to selected medical images; and the electronic device being further configured to display the selected medical images according to the identified display preferences, thereby allowing matched medical images to be visually compared and displayed in a manner that is suitable to user preferences.

According to an aspect, the medical images are grouped in one or more image series.

According to another aspect, the electronic device is configured to receive a second plurality of medical images of a second medical examination and select medical images of the first medical examination and the second medical examination that satisfy the selection criteria of the user-defined rules, thereby allowing a user to match medical images of the first medical examination with medical images of the second medical examination according to user-specific rules.

According to yet another aspect, the electronic device is further configured to receive a plurality of second user-defined display rules, at least one of the second user-defined display rules identifying a display preference with respect to matched medical images of the first and second examinations; and wherein the electronic device is further configured to display the matched medical images in accordance with the second user-defined display rules.

According to another aspect, the electronic device is further configured to display the matched medical images in accordance with the user-defined display rules.

According to yet another aspect, the electronic device is configured to receive a plurality of second user-defined matching rules, at least one of the user-defined matching rules identifying second selection criteria for matching the selected medical images of the first examination with medical images of a second medical examination; and wherein the electronic device is configured to select medical images of the first medical examination and of second medical examination that satisfy the second selection criteria of the user-defined rules, thereby allowing a user to match medical images of the first medical examination with medical images of the second medical examination according to user-specific rules.

According to another aspect, the electronic device is configured to receive a plurality of second user-defined display rules, at least one of the second user-defined display rules identifying a display preference with respect to matched medical images of the first and second examinations, and wherein the electronic device is configured to display matched medical records in accordance with the second user-defined display rules.

According to yet another aspect, the electronic device is configured to display matched medical records in accordance with the user-defined display rules.

In another embodiment, a computing system comprises: one or more hardware computer processors; and one or more software modules configured for execution by the one or more computer processors to cause the computing system to: in response to user input, automatically: select a first image series and a second image series each associated with a particular patient and including images of a particular modality; determine an order for display of images of the first image series and the second image series, wherein the order is based on anatomical positions of the patient depicted in respective images; and display images of the first image series and the second image series, one at a time in a single image pane, in the determined order.

According to an aspect, the order is further based on one or more of date or time of acquisition of respective displayed images, laterality of images, or view of images.

According to another aspect, the user input is received from an input device in communication with the computing system.

According to yet another aspect, the one or more software modules are further configured to cause the computing system to: select images of the first image series and the second image series each associated with a different particular modality; determine a second order for display of the selected images of the first image series and the second image series, wherein the second order is based on anatomical positions of the patient depicted in respective selected images; and display the selected images of the first image series and the second image series, one at a time in a single second image pane, in the determined second order.

According to another aspect, the computing system further comprises: registering, by the computing system, images of different image series that are displayed in the single image pane.

According to yet another aspect, said registering is based on one or more of aligning centers of images in the different image series or linking scrolling between images displayed in different image panes.

In yet another embodiment, a computing system comprises: one or more hardware computer processors; and one or more software modules configured for execution by the one or more computer processors to cause the computing system to: in response to user input, automatically: select a first image series and a second image series each associated with a particular patient and including images of a particular modality, wherein the first image series and the second image series together comprise a matched set; determine an order for display of images of the matched set, wherein the images of the first image series and a second image series are ordered for progressive display of the matched set; and display images of the matched set, one at a time in a single image pane, in the determined order.

According to an aspect, the order is based on one or more of date or time of acquisition of respective displayed images, laterality of images, or view of images.

According to another aspect, the user input is received from an input device in communication with the computing system.

According to yet another aspect, the one or more software modules are further configured to cause the computing system to: select images of the first image series and the second image series each associated with a different particular modality, wherein the selected images of the first image series and the second image series together comprise a second matched set; determine a second order for display of the selected images of the second matched set, wherein the selected images of the first image series and the second image series are ordered for progressive display of the second matched set; and display the selected images of the second matched set, one at a time in a single second image pane, in the determined second order.

In another embodiment, a computing system comprises: one or more hardware computer processors; and one or more software modules including computer executable instructions and configured for execution by the one or more computer processors to cause the computing system to: access images of one or more image series; identify images of the one or more image series that are similar based on similarities in one or more of name, modality, plane, contrast, and/or width of respective images; determine a display order of a first set of images that are determined to be similar, wherein the display order is determined based on a first DICOM attribute of respective images of the first set of images; and generate a user interface for display of the first set of images in the determined display order.

According to an aspect, the first DICOM attribute includes at least one of orientation, contrast use, thickness of slices, field of view, or MRI tissue contrast weighting.

According to another aspect, the first DICOM attribute of respective images is contained in a header file of the respective images.

According to yet another aspect, the first set of images includes only images from a first image series.

According to another aspect, the first set of images includes images from at least two image series.

According to yet another aspect, the first set of images is displayed in the determined display order in a single image pane.

According to another aspect, the first set of images are displayed sequentially in the determined display order in response to a user input.

In yet another embodiment, a method comprises: accessing, by a computing system having one or more hardware processors executing computer executable instructions, images of one or more image series; identifying, by the computing system, images of the one or more image series that are similar based on similarities in one or more of name, modality, plane, contrast, and/or width of respective images; determining, by the computing system, a display order of a first set of images that are determined to be similar, wherein the display order is determined based on a first DICOM attribute of respective images of the first set of images; and generating, by the computing system, one or more user interfaces to display the first set of images in the determined display order.

According to an aspect, the method further comprises: determining, by the computing system, a second display order of the first set of images, wherein the second display order is determined based on a second DICOM attribute of respective images of the first set of images; and displaying, on an electronic display of the computing system or another computing device, the first set of images in the determined second display order.

According to another aspect, the method further comprises: identifying, by the computing system, a second set of images of the one or more image series that are similar based on second similarities in one or more of name, modality, plane, contrast, and/or width of respective images; determining, by the computing system, a second display order of the second set of images, wherein the second display order is determined based on a second DICOM attribute of respective images of the second set of images; and updating, by the computing system, the one or more user interfaces to display the second set of images in the determined second display order.

According to yet another aspect, the first set of images includes only images from a first image series.

According to another aspect, the first set of images includes images from at least two image series.

According to yet another aspect, the first set of images is displayed in the determined display order in a single image pane.

In another embodiment, a non-transitory computer-readable storage medium storing software code is disclosed that, when executed by a computer system, configures the computer system to perform operations comprising: accessing images of one or more image series; identifying images of the one or more image series that are similar based on similarities in one or more of name, modality, plane, contrast, and/or width of respective images; determining a display order of a first set of images that are determined to be similar, wherein the display order is determined based on a first DICOM attribute of respective images of the first set of images; and providing the first set of images for display in the determined display order.

According to an aspect, the first set of images includes only images from a first image series.

According to another aspect, the first set of images includes images from at least two image series.

According to yet another aspect, the first set of images is displayed in the determined display order in a single image pane.

According to another aspect, the first set of images are displayed sequentially in the determined display order in response to a user input.

According to another embodiment, a database computing system for processing digital images comprises: an electronic display; an input device; and one or more computer processors in communication with the electronic display, the input device, and a non-transitory computer-readable medium storing software modules including software instructions that are executable by the one or more computer processors, the software modules including at least: a user input module configured to: receive an indication of a selection of a first image series of a first medical exam associated with a patient, wherein the first image series includes a first plurality of medical images; and a rules engine module configured to access one or more matching rules and a first one or more sorting rules, the first one or more sorting rules indicating a first attribute and a second attribute, the rules engine module further configured to: determine, based on the one or more matching rules, a second image series of a second medical exam for comparison with the first image series, wherein the second image series includes a second plurality of medical images, and wherein the second medical exam is also associated with the patient and was acquired at a time different from a time that the first medical exam was acquired; sort a set of images including the images of both the first image series and the second image series to determine a sorted set of images by at least: sorting the set of images based on the first attribute; and for each sorted group of images having a common first attribute, further sorting the group of images based on the second attribute such that the sorted set of images are sorted based on both the first and second attributes; wherein the user input module is further configured to: receive a first user input; wherein the rules engine module is further configured to: in response to the first user input, access a second one or more sorting rules indicating a third attribute and a fourth attribute; and re-sort the set of images to determine a re-sorted set of images by at least: sorting the set of images based on the third attribute; and for each sorted group of images having a common third attribute, further sorting the group of images based on the fourth attribute such that the re-sorted set of images are sorted based on both the third and fourth attributes.

According to an aspect, the first and fourth attributes are the same, and the second and third attributes are the same.

According to another aspect, the software modules further include at least: a user interface module configured to: generate user interface data useable for displaying a user interface on the electronic display, the user interface including a first image of the sorted set of images in a first location; and in response to a second user input indicating a direction of movement within the sorted set of images, update the user interface data such that, in the user interface, the first image is replaced with a second image of the sorted set of images that is adjacent to the first image in the sorted set of images, wherein the second image is included in the first location.

According to yet another aspect, the set of images is re-sorted in response to the first user input.

According to another aspect, the user interface module is further configured to: further in response to the first user input, update the user interface data such that the user interface includes a third image of the re-sorted set of images in the first location; and in response to a third user input indicating a direction of movement within the re-sorted set of images, update the user interface data such that, in the user interface, the third image is replaced with a fourth image of the re-sorted set of images that is adjacent to the third image in the re-sorted set of images, wherein the fourth image is included in the first location.

According to yet another aspect, the rules engine module is further configured to: adjust one or more image characteristics of images of the sorted set of images to reduce artifactual differences between images for comparison.

According to another aspect, the rules engine module is further configured to: adjust the one or more image characteristics of images of the sorted set of images based on a landmark identified in at least two of the images of the sorted set of images.

According to yet another aspect, the rules engine module is further configured to: adjust one or more image characteristics of images of the re-sorted set of images to reduce artifactual differences between images for comparison According to yet another embodiment, a database computing system for processing digital images comprises: an electronic display; an input device; a non-transitory computer-readable storage medium configured to store software instructions; and one or more computer processors in communication with the electronic display, the input device, and the non-transitory computer-readable medium, the one or more computer processors configured to execute the software instructions in order to cause the computing system to: receive an indication of a selection of a first image series of a first medical exam associated with a patient, wherein the first image series includes a first plurality of medical images; select from a plurality of decision support image series, based on one or more rules and at least one characteristic of the patient, a clinical decision support image series including a second plurality of medical images; access a first one or more sorting rules indicating a first attribute and a second attribute; and determine a set of images to be sorted, the set of imagines including the first plurality of images of the first image series and the second plurality of images of the clinical decision support image series; sorting the set of images based on the first attribute; and further sorting the set of images based on the second attribute such that the sorted set of images are sorted based on both the first and second attributes.

According to an aspect, the clinical decision support image series includes at least one of: reference medical images, or medical images of another patient that has at least one characteristic matching the at least one characteristic of the patient.

According to another aspect, the one or more computer processors are configured to execute the software instructions in order to further cause the computing system to: in response to a first user input, access a second one or more sorting rules indicating a third attribute and a fourth attribute; and re-sort the set of images to determine a re-sorted set of images by at least: sorting the set of images based on the third attribute; and further sorting the set of images based on the fourth attribute such that the sorted set of images are sorted based on both the third and fourth attributes.

According to yet another aspect, the one or more computer processors are configured to execute the software instructions in order to further cause the computing system to: in response to receiving the indication of the selection, automatically analyze data of the first medical exam; determine the first medical exam is a candidate for clinical decision support; and prompt a user to select to compare at least the first image series with clinical decision support data, wherein the clinical decision support image series is determined in response to a second input from the user selecting to compare at least the first image series with clinical decision support data.

According to another embodiment, a database computing system for processing digital images comprises: an electronic display; an input device; a non-transitory computer-readable storage medium configured to store software instructions; and one or more computer processors in communication with the electronic display, the input device, and the non-transitory computer-readable medium, the one or more computer processors configured to execute the software instructions in order to cause the computing system to: access a first dual-image radiography medical exam of a patient obtained at a first time, wherein the first dual-image radiography medical exam includes a first plurality of image series of a chest of the patient; receive an indication of a selection of a first image series of the first plurality of image series of the first dual-image radiography medical exam; in response to receiving the indication of the selection, determine, based on one or more matching rules, a second image series of a second plurality of image series of a second dual-image radiography medical exam, wherein the second dual-image radiography medical exam is also of the patient and was obtained at a second time different than the first time; access a first one or more sorting rules indicating a first attribute and a second attribute, wherein one of the first attribute and the second attribute is a view type and another of the first attribute and the second attribute is a time of acquisition; and sort a set of images including the images of both the first and second image series to determine a sorted set of images by at least: sorting the set of images based on the first attribute; and further sorting the set of images based on the second attribute such that the sorted set of images are sorted based on both the first and second attributes.

According to an aspect, each of the first plurality of image series and the second plurality of image series include at least one image series of at least one of: a traditional view type, or a bones out view type.

According to another aspect, the one or more computer processors are configured to execute the software instructions in order to further cause the computing system to: in response to a first user input, re-sort the set of images to determine a re-sorted set of images by at least: sorting the set of images based on the second attribute; and further sorting the set of images based on the first attribute such that the sorted set of images are sorted based on both the second and first attributes.

According to yet another embodiment, a database computing system for processing digital images comprises: an electronic display; an input device; a non-transitory computer-readable storage medium configured to store software instructions; and one or more computer processors in communication with the electronic display, the input device, and the non-transitory computer-readable medium, the one or more computer processors configured to execute the software instructions in order to cause the computing system to: receive an indication of a selection of a first medical image of a first image series of a first medical exam associated with a patient, wherein the first image series includes a first plurality of medical images; determine, based on one or more matching rules, a comparison image series of a comparison medical exam for comparison with the first image series, wherein the comparison image series includes a second plurality of comparison images, and wherein the comparison medical exam is also associated with the patient and was acquired at a time different than the first medical exam; identify, based on one or more attributes of the first medical image, a first comparison image of the comparison image series for comparison with the first medical image; generate user interface data useable for displaying a user interface on the electronic display, the user interface including at least: the first medical image of the first image series displayed in a first image pane in a first location; and the first comparison image of the second image series displayed in a second image pane in a second location; in response to a first user input indicating a direction of movement within the first image series: update the user interface data such that, in the user interface, the first medical image is replaced with a second medical image of the first image series that is adjacent to the first medical image in the first image series, wherein the second medical image replaces the first medical image in the first image pane; identify, based on one or more attributes of the second medical image, a second comparison image of the comparison image series for comparison with the second medical image; and further update the user interface data such that, in the user interface, the first comparison image is replaced with the second comparison image, wherein the second comparison image replaces the first comparison image in the second image pane; and in response to a second user input indicating selection of a second image series of the first medical exam: determine, based on one or more attributes of the second medical image, a first medical image of the second image series for display; update the user interface data such that, in the user interface, the second medical image is replaced with the first medical image of the second image series, wherein the first medical image of the second image series replaces the second medical image of the first image series in the first image pane; identify, based on one or more attributes of the second image series, a second comparison image series of the comparison medical exam for comparison with the second image series; identify, based on one or more attributes of the first medical image of the second image series, a first comparison image of the second comparison image series for comparison with the first medical image of the second image series; and further update the user interface data such that, in the user interface, the second comparison image of the comparison image series is replaced with the first comparison image of the second comparison image series, wherein the first comparison image of the second comparison image series replaces the second comparison image of the comparison image series in the second image pane.

According to an aspect, the first comparison image of the comparison image series is further identified based on one or more matching rules.

According to another aspect, the second comparison image of the comparison image series is further identified based on one or more matching rules.

According to yet another aspect, the first comparison image of the second comparison image series is further identified based on one or more matching rules.

According to another aspect, the first location of the first image pane and the second location of the second image pane are adjacent to one another.

According to another embodiment, a database computing system for processing digital images comprises: an electronic display; an input device; a non-transitory computer-readable storage medium configured to store software instructions; and one or more computer processors in communication with the electronic display, the input device, and the non-transitory computer-readable medium, the one or more computer processors configured to execute the software instructions in order to cause the computing system to: display, on the electronic display, a first medical image of a first image series of a first medical exam in a first image pane, wherein the first medical exam is associated with a patient; display, on the electronic display, a first medical image of a comparison image series of a second medical exam in a second image pane, wherein the comparison medical exam is also associated with the patient, wherein the second medical exam was acquired at a time different from the first medical exam, and wherein the first medical image of the comparison image series matches the first medical image of the first image series in at least one attribute such that the first medical image of the first image series and first medical image of the comparison image series may be usefully compared for diagnosis; in response to a first user input indicating a change from the first medical image of the first image series to another medical image of the first image series: replace, in the first image pane, the first medical image of the first image series with the another medical image of the first image series; and replace, in the second image pane, the first medical image of the comparison image series with another medical image of the comparison image series, wherein the another medical image of the comparison image series matches the another medical image of the first image series in at least one attribute such that the another medical image of the first image series and the another medical image of the comparison image series may be usefully compared for diagnosis; and in response to a second user input indicating a change from the first image series of the first medical exam to another image series of the first medical exam: replace, in the first image pane, the first medical image of the first image series with the another medical image of the another image series of the first medical exam; and replace, in the second image pane, the first medical image of the comparison image series with another medical image of another image series of the second medical exam, wherein the another medical image of the another image series of the second medical exam matches the another medical image of the another image series of the first medical exam in at least one attribute such that the another medical image of the another image series of the first medical exam and the another medical image of the another image series of the second medical exam may be usefully compared for diagnosis.

According to an aspect, the one or more computer processors are configured to execute the software instructions in order to further cause the computing system to: in response to a third user input, freeze at least the second image pane such that a medical image displayed in the second image pane is not replaced in response to the first and/or second user inputs.

According to another aspect, the first and second image panes are adjacent to one another.

According to yet another aspect, the second medical exam was acquired before the first medical exam.

According to yet another embodiment, a method comprises: by one or more computer processors configured to execute software instructions: displaying, on an electronic display, a first medical image of a first image series of a first medical exam in a first image pane, wherein the first medical exam is associated with a patient; displaying, on the electronic display, a first medical image of a comparison image series of a second medical exam in a second image pane, wherein the comparison medical exam is also associated with the patient, wherein the second medical exam was acquired at a time different from the first medical exam, and wherein the first medical image of the comparison image series matches the first medical image of the first image series in at least one attribute such that the first medical image of the first image series and first medical image of the comparison image series may be usefully compared for diagnosis; in response to a first user input indicating a change from the first medical image of the first image series to another medical image of the first image series: replacing, in the first image pane, the first medical image of the first image series with the another medical image of the first image series; and replacing, in the second image pane, the first medical image of the comparison image series with another medical image of the comparison image series, wherein the another medical image of the comparison image series matches the another medical image of the first image series in at least one attribute such that the another medical image of the first image series and the another medical image of the comparison image series may be usefully compared for diagnosis; and in response to a second user input indicating a change from the first image series of the first medical exam to another image series of the first medical exam: replacing, in the first image pane, the first medical image of the first image series with the another medical image of the another image series of the first medical exam; and replacing, in the second image pane, the first medical image of the comparison image series with another medical image of another image series of the second medical exam, wherein the another medical image of the another image series of the second medical exam matches the another medical image of the another image series of the first medical exam in at least one attribute such that the another medical image of the another image series of the first medical exam and the another medical image of the another image series of the second medical exam may be usefully compared for diagnosis.

According to an aspect, the method further comprises: by the one or more computer processors configured to execute software instructions: in response to a third user input, freezing at least the second image pane such that a medical image displayed in the second image pane is not replaced in response to the first and/or second user inputs.

According to another aspect, the first and second image panes are adjacent to one another.

According to yet another aspect, the second medical exam was acquired before the first medical exam.

According to another embodiment, a database computing system for processing digital images comprises: an electronic display; an input device; a non-transitory computer-readable storage medium configured to store software instructions; and one or more computer processors in communication with the electronic display, the input device, and the non-transitory computer-readable medium, the one or more computer processors configured to execute the software instructions in order to cause the computing system to: access a plurality of medical images associated with a plurality of medical exams of a patient; analyze the plurality of medical images to determine, for each medical image, respective attributes of the medical images; sort the plurality of medical images into a plurality of image series based on the attributes of the medical images, wherein the plurality of image series includes at least a first image series and a second image series; analyzing the first and second image series to determine pairs of medical images of the respective image series that are related to one another; generate user interface data useable for displaying a user interface on the electronic display, the user interface including at least: a first medical image of the first image series displayed in a first image pane in a first location; and a first medical image of the second image series displayed in a second image pane in a second location; and in response to a first user input indicating a direction of movement within the first image series: update the user interface data such that, in the user interface, the first medical image of the first image series is replaced with a second medical image of the first image series that is adjacent to the first medical image of the first image series in the first image series, wherein the second medical image of the first image series replaces the first medical image in the first image pane; identify, based on one or more attributes of the second medical image of the first image series, a second medical image of the second image series for comparison with the second medical image of the first image series; and further update the user interface data such that, in the user interface, the first medical image of the second image series is replaced with the second medical image of the second image series, wherein the second medical image of the second image series replaces the first medical image of the second image series in the second image pane.

According to an aspect, the one or more computer processors are further configured to execute the software instructions in order to cause the computing system to: in response to a second user input indicating a direction of movement within the first image series: update the user interface data such that, in the user interface, the first medical image of the first image series is replaced with a second medical image of the first image series that is adjacent to the first medical image of the first image series in the first image series, wherein the second medical image of the first image series replaces the first medical image in the first image pane; determine, based on one or more attributes of the second medical image of the first image series, that no medical image of the second image series corresponding to the second medical image of the first image series exists; and further update the user interface data such that, in the user interface, the first medical image of the second image series is replaced with a placeholder in the second image pane.

According to an aspect, the placeholder comprises at least one of a blank image or an absence of an image.

According to an aspect, analyzing the plurality of medical images to determine, for each medical image, respective attributes of the medical images comprises: analyzing the plurality of medical images to determine, for each medical image, respective view types of the medical images; The computing system of claim 14, wherein each image series of the plurality of image series comprises a series of medical images having a common view type According to an aspect, the plurality of medical images comprise chest radiograph images.

According to an aspect, the analyzing the first and second image series to determine pairs of medical images of the respective image series that are related to one another comprises: analyzing the first and second image series to determine pairs of medical images of the respective image series that are from a same exam and/or acquired at a similar time.

According to an aspect, the one or more computer processors are further configured to execute the software instructions in order to cause the computing system to: determine the first and second locations of the respective first and second image panes based on one or more user preferences.

According to an aspect, the one or more computer processors are further configured to execute the software instructions in order to cause the computing system to: determine an association between the first image pane and the first image series based on one or more user preferences.

According to an aspect, the one or more computer processors are further configured to execute the software instructions in order to cause the computing system to: registering the medical images of the first image series so as to enable efficient comparison of the medical images of the first image series.

According to another embodiment, a database computing system for processing digital images comprises: an electronic display; an input device; a non-transitory computer-readable storage medium configured to store software instructions; and one or more computer processors in communication with the electronic display, the input device, and the non-transitory computer-readable medium, the one or more computer processors configured to execute the software instructions in order to cause the computing system to: generate user interface data useable for displaying a user interface on the electronic display, the user interface including at least a plurality of selectable image thumbnails; and in response to a user input indicating selection of a first image thumbnail of the plurality of selectable image thumbnails: determine a first medical image of a first image series of a first medical exam associated with the first image thumbnail, wherein the first image series includes a first plurality of medical images, and wherein the first medical exam is associated with a patient; determine, based on one or more matching rules, a comparison series of a comparison exam for comparison with the first image series, wherein the comparison series includes a second plurality of medical images, and wherein the comparison medical exam is also associated with the patient and was acquired at a time different than the first medical exam; identify, based on one or more attributes of the first medical image, a comparison medical image of the comparison image series for comparison with the first medical image; and update the user interface data such that the user interface includes at least: the first medical image of the first image series displayed in a first image pane in a first location; and the comparison medical image of the comparison image series displayed in a second image pane in a second location.

According to an aspect, the user input indicating selection of the first image thumbnail of the plurality of selectable image thumbnails comprises a dragging of the first image thumbnail from a first portion of the user interface to a second portion of the user interface.

According to another aspect, the one or more computer processors are configured to execute the software instructions in order to further cause the computing system to: in response to a second user input indicating a request to sort medical images: access a first one or more sorting rules indicating a first attribute and a second attribute; sort a set of images including the first and second plurality of medical images to determine a sorted set of images by at least: sorting the set of images based on the first attribute; and further sorting the set of images based on the second attribute such that the sorted set of images are sorted based on both the first and second attributes; and update the user interface data such that the user interface includes at least: a third image pane overlaying the first and second image panes, wherein a first image of the sorted set of images is displayed in the third image pane.

According to yet another aspect, the one or more computer processors are configured to execute the software instructions in order to further cause the computing system to: in response to a third user input indicating a direction of movement within the sorted set of images, update the user interface data such that, in the user interface, the first image is replaced with a second image of the sorted set of images that is adjacent to the first image in the sorted set of images, wherein the second image is displayed in the third image pane.

According to another aspect, the first and second locations are adjacent to one another.

According to yet another embodiment, a method comprises: by one or more computer processors configured to execute software instructions: generating user interface data useable for displaying a user interface on an electronic display, the user interface including at least a plurality of selectable image thumbnails; and in response to a user input indicating selection of a first image thumbnail of the plurality of selectable image thumbnails: determining a first medical image of a first image series of a first medical exam associated with the first image thumbnail, wherein the first image series includes a first plurality of medical images, and wherein the first medical exam is associated with a patient; determining, based on one or more matching rules, a comparison series of a comparison exam for comparison with the first image series, wherein the comparison series includes a second plurality of medical images, and wherein the comparison medical exam is also associated with the patient and was acquired at a time different than the first medical exam; identifying, based on one or more attributes of the first medical image, a comparison medical image of the comparison image series for comparison with the first medical image; and updating the user interface data such that the user interface includes at least: the first medical image of the first image series displayed in a first image pane in a first location; and the comparison medical image of the comparison image series displayed in a second image pane in a second location.

According to an aspect, the user input indicating selection of the first image thumbnail of the plurality of selectable image thumbnails comprises a dragging of the first image thumbnail from a first portion of the user interface to a second portion of the user interface.

According to another aspect, the method further comprises: by the one or more computer processors configured to execute software instructions: in response to a second user input indicating a request to sort medical images: accessing a first one or more sorting rules indicating a first attribute and a second attribute; sorting a set of images including the first and second plurality of medical images to determine a sorted set of images by at least: sorting the set of images based on the first attribute; and further sorting the set of images based on the second attribute such that the sorted set of images are sorted based on both the first and second attributes; and updating the user interface data such that the user interface includes at least: a third image pane overlaying the first and second image panes, wherein a first image of the sorted set of images is displayed in the third image pane.

According to yet another aspect, the method further comprises: by the one or more computer processors configured to execute software instructions: in response to a third user input indicating a direction of movement within the sorted set of images, updating the user interface data such that, in the user interface, the first image is replaced with a second image of the sorted set of images that is adjacent to the first image in the sorted set of images, wherein the second image is displayed in the third image pane.

According to another aspect, the first and second locations are adjacent to one another.

According to another embodiment, a computer program product comprises a computer readable storage medium having program instructions embodied therewith, the program instructions executable by a computer processor to cause the computer processor to: generate user interface data useable for displaying a user interface on an electronic display, the user interface including at least a plurality of selectable image thumbnails; and in response to a user input indicating selection of a first image thumbnail of the plurality of selectable image thumbnails: determine a first medical image of a first image series of a first medical exam associated with the first image thumbnail, wherein the first image series includes a first plurality of medical images, and wherein the first medical exam is associated with a patient; determine, based on one or more matching rules, a comparison series of a comparison exam for comparison with the first image series, wherein the comparison series includes a second plurality of medical images, and wherein the comparison medical exam is also associated with the patient and was acquired at a time different than the first medical exam; identify, based on one or more attributes of the first medical image, a comparison medical image of the comparison image series for comparison with the first medical image; and update the user interface data such that the user interface includes at least: the first medical image of the first image series displayed in a first image pane in a first location; and the comparison medical image of the comparison image series displayed in a second image pane in a second location.

According to an aspect, the user input indicating selection of the first image thumbnail of the plurality of selectable image thumbnails comprises a dragging of the first image thumbnail from a first portion of the user interface to a second portion of the user interface.

According to another aspect, the program instructions are executable by a computer processor to further cause the computer processor to: in response to a second user input indicating a request to sort medical images: access a first one or more sorting rules indicating a first attribute and a second attribute; sort a set of images including the first and second plurality of medical images to determine a sorted set of images by at least: sorting the set of images based on the first attribute; and further sorting the set of images based on the second attribute such that the sorted set of images are sorted based on both the first and second attributes; and update the user interface data such that the user interface includes at least: a third image pane overlaying the first and second image panes, wherein a first image of the sorted set of images is displayed in the third image pane.

According to yet another aspect, the program instructions are executable by a computer processor to further cause the computer processor to: in response to a third user input indicating a direction of movement within the sorted set of images, update the user interface data such that, in the user interface, the first image is replaced with a second image of the sorted set of images that is adjacent to the first image in the sorted set of images, wherein the second image is displayed in the third image pane.

According to another aspect, the first and second locations are adjacent to one another.

According to yet another embodiment, a database computing system for processing digital images comprises: an electronic display; an input device; and one or more computer processors in communication with the electronic display, the input device, and a non-transitory computer-readable medium storing software modules including software instructions that are executable by the one or more computer processors in order to cause the one or more computer processors to: access an image series comprising a plurality of images, wherein at least some of the plurality of images comprise multi-frame images; display a first image of the plurality of images at a location on the electronic display; in response to a first input, received via the input device, display a frame of a second image of the plurality of images at the location on the electronic display, wherein the frame of the second image replaces the first image on the electronic display, wherein the second image comprises a multi-frame image; in response to a second input, received via the input device: create a copy of the frame of the second image; and add the copy of the frame of the second image to the image series as a new image; and sort the image series such that the new image is located adjacent to the second image in the image series.

According to an aspect, the one or more computer processors are configured to execute the software instructions in order to further cause the computing system to: further in response to the second input, add the copy of the frame of the second image to a montage; and add the montage to the image series.

According to another aspect, the one or more computer processors are configured to execute the software instructions in order to further cause the computing system to: further in response to the second input, generate data necessary to create a montage including the frame of the second image and any changes to the frame of the second image indicated by the second input; and add an indication of the montage to the image series.

According to yet another aspect, the second input indicates adding an annotation to the frame of the second image.

According to another aspect, the second input indicates the frame of the second image is a key image.

According to yet another aspect, the second input indicates a change of an image characteristic of the frame of the second image.

According to another embodiment, a database computing system for processing digital images comprises: an electronic display; an input device; and one or more computer processors in communication with the electronic display, the input device, and a non-transitory computer-readable medium storing software modules including software instructions that are executable by the one or more computer processors in order to cause the one or more computer processors to: access an image series comprising a plurality of images, wherein at least some of the plurality of images comprise multi-frame images; display a first image of the plurality of images at a location on the electronic display; in response to a first input, received via the input device, display a frame of a second image of the plurality of images at the location on the electronic display, wherein the frame of the second image replaces the first image on the electronic display, wherein the second image comprises a multi-frame image; in response to a second input, received via the input device: create data including an indication of the frame of the second image and information associated with the second input; and add the data to the image series as an indication of an additional image; and sort the image series such that the additional image is located adjacent to the second image in the image series.

According to an aspect, the information associated with the second input includes at least one of: an indication that the frame of the second image is a key image, an addition of an annotation to the frame of the second image, or an adjustment to an image characteristic of the frame of the second image.

According to another aspect, the one or more computer processors are configured to execute the software instructions in order to further cause the computing system to: in response to a third input, received via the input device, indicating that the additional image is to be displayed: generate the additional image based on the data including the indication of the frame of the second image and the information associated with the second input; and display the additional image in the location on the electronic display.

According to yet another aspect, the one or more computer processors are configured to execute the software instructions in order to further cause the computing system to: further in response to the second input, add a copy of the frame of the second image to a montage; and add the montage to the image series.

According to another aspect, the one or more computer processors are configured to execute the software instructions in order to further cause the computing system to: further in response to the second input, generate data necessary to create a montage including the frame of the second image and any changes to the frame of the second image indicated by the second input; and add an indication of the montage to the image series.

According to yet another embodiment, a database computing system for processing digital images comprises: an electronic display; an input device; and one or more computer processors in communication with the electronic display, the input device, and a non-transitory computer-readable medium storing software modules including software instructions that are executable by the one or more computer processors in order to cause the one or more computer processors to: access an image series comprising a plurality of images, wherein at least some of the plurality of images comprise multi-frame images; display a first image of the plurality of images at a location on the electronic display; in response to a first input, received via the input device: create a copy of the first image; and add the copy of the first image to the image series as a new image; and sort the image series, including the new image, based one or more user preferences or sorting rules.

According to an aspect, sorting the image series comprises: accessing a first one or more sorting rules indicating a first attribute and a second attribute; and sorting the image series by at least: sorting images of the image series based on the first attribute; and further images of the image series based on the second attribute such that the images of the image series are sorted based on both the first and second attributes.

According to another aspect, the one or more computer processors are configured to execute the software instructions in order to further cause the computing system to: further in response to the second input, add the copy of the first image to a montage; and add the montage to the image series.

According to yet another aspect, the one or more computer processors are configured to execute the software instructions in order to further cause the computing system to: further in response to the second input, generate data necessary to create a montage including the first image and any changes to the first image indicated by the second input; and add an indication of the montage to the image series.

According to another aspect, the second input indicates adding an annotation to the first image.

According to yet another aspect, the second input indicates the first image is a key image.

According to another aspect, the second input indicates a change of an image characteristic of the first image.

Additional embodiments of the disclosure are described below in reference to the appended claims, which may serve as an additional summary of the disclosure.

In various embodiments, computer systems are disclosed that comprise one or more hardware computer processors in communication with one or more non-transitory computer readable storage devices, wherein the one or more hardware computer processors are configured to execute the plurality of computer executable instructions in order to cause the computer system to operations comprising one or more aspects of the above-described embodiments (including one or more aspects of the appended claims).

In various embodiments, computer-implemented methods are disclosed in which, under control of one or more hardware computing devices configured with specific computer executable instructions, one or more aspects of the above-described embodiments (including one or more aspects of the appended claims) are implemented and/or performed.

In various embodiments, computer readable storage mediums storing software instructions are disclosed, wherein, in response to execution by a computing system having one or more hardware processors, the software instructions configure the computing system to perform operations comprising one or more aspects of the above-described embodiments (including one or more aspects of the appended claims).

BRIEF DESCRIPTION OF THE DRAWINGS

The following drawings and the associated descriptions are provided to illustrate embodiments of the present disclosure and do not limit the scope of the claims. Aspects and many of the attendant advantages of this disclosure will become more readily appreciated as the same become better understood by reference to the following detailed description, when taken in conjunction with the accompanying drawings, wherein:

FIG. 6 is a flowchart illustrating an example method of viewing images from multiple image series, according to an embodiment of the present disclosure.

FIGS. 7A and 7B are example images of a first image series.

FIG. 15B is an illustration of four example image series to be sorted, and attributes associated with each.

FIGS. 15D and 15E are examples of sorting of the images of the four example image series of FIG. 15B.

DETAILED DESCRIPTION

Figure 1:
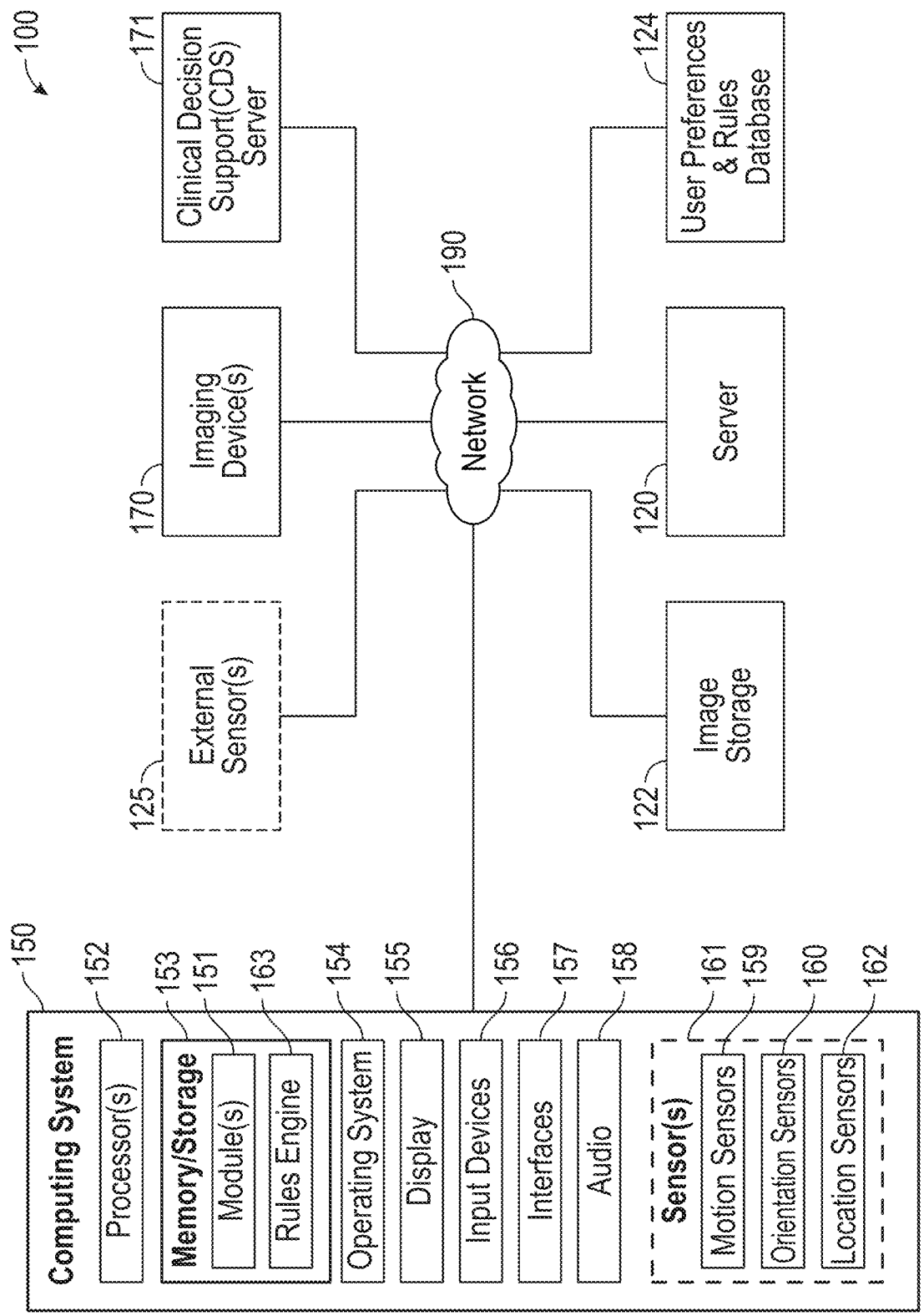
FIG. 1 is a block diagram showing various aspects of a computing system and network environment in which the computing system may be implemented, according to various embodiments of the present disclosure.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

I. Overview

As mentioned above, according to various embodiments systems are disclosed that enable a user to more quickly, thoroughly, and efficiently, as compared to previous systems, interact with image data, including medical images, to determine differences between related medical images and evaluate medical images.

As also mentioned above, according to various embodiments a data navigation system is disclosed in which a user may interact with medical images (including two-dimensional images and images rendered from three-dimensional image data) to enable detection of differences between related medical images and evaluation of medical images. In various embodiments described herein, images from one or more series and/or exams are automatically analyzed and sorted. In an embodiment, reference image data is alternatively, or also, sorted with images. The system enables fast and efficient evaluation and comparison of related images as a result of the sorting. For example, sorted images may be rapidly paged through to enable detailed comparison of images and detection of changes (including, e.g., changes in a medical condition of a patient). User interfaces of the system are thus dynamically updated to provide rapid comparison of images. Further, images from multiple series and/or exams, and/or images from other sources, may be automatically sorted by the system according to attributes associated with the images and rules and/or preferences of the user.

In an embodiment, the user may select an image from a series of a first exam, and the system automatically determines and displays one or more comparison images from other image series and/or exams. Images selected for comparison, and/or images that are sorted, may additionally be automatically registered and/or matched to enable more efficient comparison and evaluation by the user. Accordingly, a user may use the systems described herein to more quickly, thoroughly, and efficiently interact with medical images, as compared to previous systems.

In various embodiments, systems and methods are disclosed for matching related medical images and/or medical image series from multiple exams, automatically displaying medical images in particular arrangements, and automatically sorting medical images from related exams. In one example, a user selects a medical image, and the system automatically identifies related images and/or medical image exams from 2, 3, or 4 (or more) other exams and displays the images next to one another in a grid arrangement, and/or sorts the images and displays them sequentially in an image pane.

In an embodiment, a user interface of the system includes one or more image panes in which medical images may be displayed. As described in further detail below, such a user interface may provide one or more comparison panes on a display device in which images from multiple image series are sequentially displayed.

In various embodiments, medical images may be reconstructed and/or rendered from 3D or volumetric image data using methods including multiplanar reformation/reconstruction (MPR), maximum intensity projection (MIP), and/or the like. Such rendered images may be rendered to match comparison images from other image series and/or exams so as to enable more efficient comparison and evaluation by the user.

Rendering and/or reconstruction of images from 3D or volumetric image data can be a computationally intensive task that requires significant processing power. Three-dimensional medical image data sets can be on the order of multiple gigabytes in size, therefore requiring efficient computer algorithms to generate human-useable images and other information. Typically, such 3D data sets are acquired by CT, MRI, and/or other similar modality. Volume rendering (e.g., rendering 2D projections of 3D data sets) may be accomplished by, e.g., direct volume rendering, maximum intensity projection, and/or the like, and may require one or more computational optimization techniques to be fast enough to be useful. Other reconstruction processes (e.g., rendering 2D slices of 3D data sets) include, e.g., multiplanar reconstruction. These processes also require processing of large 3D data sets via optimized rendering and/or reconstruction algorithms on computer processors.

While the use of medical imaging data (e.g., medical images) is described in the example embodiments herein, in various embodiments the systems and methods described may be used for display of, and interaction with, non-medical information, for example, seismic information, weather data, and/or financial data, among others.

Additionally, while the examples herein describe the use of information acquired from a physical object such as a patient, the systems and methods described may be used to display information obtained or generated in other ways, for example, information calculated in a simulation (for example, a financial simulation, and/or a physics simulation, among others). The systems and methods described herein may be used for display of any type of information that can be represented on a digital display.

As described above, various embodiments of the present disclosure provide improvements to various technologies and technological fields, including medical image interaction technology (e.g., Picture Archiving and Communication Systems, Electronic Medical Record systems, and/or the like). Additionally, various embodiments of the present disclosure are inextricably tied to computer technology. In particular, various embodiments rely on detection of user inputs via graphical user interfaces, calculation of updates to displayed electronic data based on those user inputs, automatic processing of related electronic medical images, and/or presentation of the updates to displayed medical images via interactive graphical user interfaces. Such features and others (e.g., generation of 2D medical images from a 3D imaging volume and/or other 2D images, such as at automatically selected or user-selected planes) are intimately tied to, and enabled by, computer technology, and would not exist except for computer technology. For example, the interactions with displayed data described below in reference to various embodiments cannot reasonably be performed by humans alone, without the computer technology upon which they are implemented. Further, the implementation of the various embodiments of the present disclosure via computer technology enables many of the advantages described herein, including more efficient interaction with, and presentation of, various types of electronic image data.

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

II. Definitions

In order to facilitate an understanding of the systems and methods discussed herein, a number of terms are defined below. The terms defined below, as well as other terms used herein, should be construed broadly to include the provided definitions, the ordinary and customary meaning of the terms, and/or any other implied meaning for the respective terms. Thus, the definitions below do not limit the meaning of these terms, but only provide exemplary definitions.

User: Also referred to herein as "reviewer" and/or "viewer." An individual (or group of individuals) that interfaces with a computing device to, for example, view medical images. Users may include, for example, physicians (including, for example, doctors, radiologists, etc.) hospital staff, and/or any other individuals (including persons not medically trained) involved in analysis, annotation, comparison, acquisition, storage, management, or other tasks related to medical images (or any other types of images) as described herein. Any discussion herein of user preferences and/or rules associated with users should be construed to also, or alternatively, include user group preferences (or rules associated with groups of users), site preferences/rules, system preference/rules, and/or default software preferences/rules.

Figure 13:
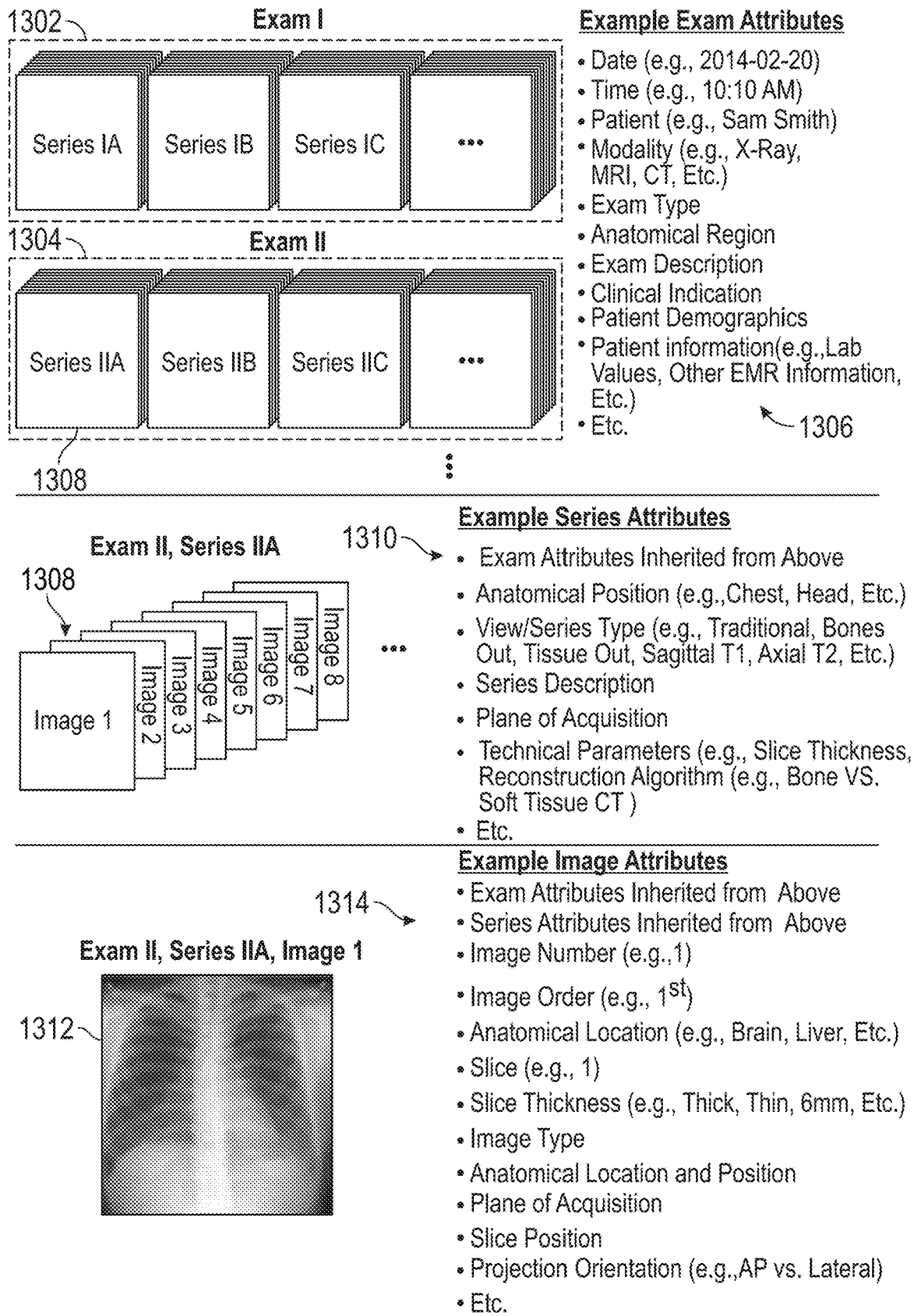
FIG. 13 illustrates various example attributes that may be associated with exams, image series, and images, according to embodiments of the present disclosure.

Medical Image (also referred to herein as an "Image"): Any type of image of an organism (e.g., a human patient). It may include but is not limited to a radiograph (e.g., an x-ray image), computed tomography (CT), magnetic resonance imaging (MRI), Ultrasound (US), mammogram, positron emission tomography scan (PET), nuclear scan (NM), pathology, endoscopy, ophthalmology, or many other types of medical images. As mentioned above, medical images may be reconstructed and/or rendered from 3D or volumetric image data using methods including multiplanar reformation/reconstruction (MPR), maximum intensity projection (MIP), and/or the like (including, e.g., any Computerized Advanced Processing (CAP), as described below). Images of the present disclosure also include "multi-frame" images, which are images comprising multiple frames (also referred to herein as sub-images). For example, a multi-frame image may be played as a movie (e.g., showing a beating heart, where each frame shows the beating heart at a different point in time). FIG. 13 illustrates an example of a medical image 1312 and possible attributes that may be associated with a medical image. While this description is directed to viewing and tracking of medical images, the methods and systems described herein may also be used in conjunction with non-medical images, such as, images of circuit boards, airplane wings, and satellite images, for example.

Modality: A medical imaging method (e.g., a patient who undergoes an MRI is said to have been scanned with the MRI modality).

Image Series (also referred to herein as a "Series"): Any two or more images that are related. Images in a series typically share one or more common attributes, for example, a type of anatomic plane and/or an image orientation. For example, an image series may comprise two or more images of a particular patient that are acquired on a particular date, e.g., different x-ray projections of the chest. A series of contiguous 3 mm axial CT scans of the chest is another example of an image series. A brain MRI scan might include the following series: sagittal T1 weighted images, axial T1 weighted images, axial FLAIR images, axial T2 weighted images, as well as post contrast axial, sagittal and coronal T1 weighted series. An image series of an exam may be identified by its "type" (also referred to herein as a "series type" and/or a "view type"). For example, series may be acquired using different pulse sequences, acquired in different anatomic planes (also referred to herein as "imaging planes"), and/or acquired before or after administration of intravenous contrast material. An image series may be limited to images of a certain modality or may comprise images of multiple modalities. FIG. 13 illustrates an example of an image series 1308, as well as example attributes that may be associated with an image series. As shown, the image series 1308 includes multiple medical images, such as medical image 1312.

Montage: An arrangement of images. In some implementations, a montage may itself be an image which comprises two or more images stitched together into a single image in a particular arrangement. In some implementations, a montage may be a file comprising sufficient information regarding each image of the montage so that the entire montage can be recreated upon display of the montage. A montage may include images from one or more series, exams, and/or the like. Examples of montages are described in more detail below in reference to FIG. 20.

Patient: An individual who undergoes a medical imaging examination.

Medical Imaging Exam (also referred to herein as a "Medical Exam" and/or an "Exam"): A collection of data related to an examination of a patient. May be specific to a particular time or time period. Generally includes one or more medical images and/or image series, montages, reports, notes, graphs, measurements, annotations, videos, sounds or voice data, diagnoses, and/or other related information. May include multiple image series of multiple modalities, volumetric imaging data, reconstructed images and/or rendered images. For example, an exam of a patient may be the brain MRI scan mentioned above, and may include each of the image series obtained on a particular date including: sagittal T1 weighted images, axial T1 weighted images, axial FLAIR images, axial T2 weighted images, as well as post contrast axial, sagittal and coronal T1 weighted series. Another example of an exam may be a dual-energy radiography exam, which may include image data including traditional x-ray image images, bone subtracted (or "bone out") x-ray images, and/or tissue subtracted (or "tissue out") x-ray images. FIG. 13 illustrates two example medical exams 1302 and 1304. As shown, each medical exam 1302 and 1304 includes multiple image series, such as image series 1308 which is a part of medical exam 1304.

Image Characteristic: Any characteristic related to display of an image. Includes without limitation, image angle (e.g., an angle of an image with reference to a standard one or more planes of human anatomy; also referred to herein as "scan plane"), anatomical position (and/or location) (e.g., a location, with reference to a standard one or more planes of human anatomy, of the patient represented in a particular image), image orientation (e.g., an orientation of the image with reference to a standard one or more planes of human anatomy), image rotation (e.g., a rotation of the image with reference to a standard one or more planes of human anatomy), image field of view, slice thickness, image window and/or level (e.g., a contrast of the image, a brightness of the image, and/or the like), image color map (e.g., that includes information for rendering different pixel intensities as different colors), other color characteristics, image opacity (and/or opacity map), image zoom level, image cropping information, and/or the like. In some instances, one or more image characteristics may be user defined and/or based on user preferences. The term "image characteristics" is used herein in reference to 2D medical images to refer to the various characteristics of the images with reference to the physical anatomy of a patient from which they were obtained. Such 2D medical images may be obtained to show a particular slice of a patient at a particular location such that a diagnosis of the patient may be made. As described below, later obtained 2D medical images of a same location may vary with respect to one or more image characteristics such that a valid comparison between the later obtained 2D image and the earlier 2D image is difficult. Such difficulty may arise due to variance in any image characteristics of the images, including those mentioned above. Image characteristics are also referred to herein as image "attributes." Further examples of attributes are described below.

Artifactual Difference: A difference between two images that is not due to changes in patient structure, physiology, anatomy, pathology, and/or the like, but rather is a result of different image characteristics between the two images. Thus, artifactual differences do not indicate changes in physical or bodily structure of a patient (such as position, size, density, etc., of particular organs, tendons, muscles, bones, tumors, or other anatomical features). For example, scan planes of two images may differ, causing features of the two images to appear different from one of the other, even when there may be no actual differences in patient physiology. Such scan plane differences may be a result of, e.g., differences in patient position within the imaging scanner, differences in imaging scanner used and/or settings of the imaging scanner, and/or differences in how the 2D images are generated (e.g., how the plane of reconstruction and/or rendering of 2D images from a 3D volume is selected). Artifactual differences contrast with "physical," or "actual," differences which are a result of changes in patient physiology, anatomy, pathology, and/or the like. Accordingly, artifactual differences between medical images can be a source of faulty image interpretation, diagnosis, and even patient treatment. In various embodiments, the systems and methods described herein efficiently and automatically eliminate, or substantially eliminate, artifactual differences (due to, e.g., differing image characteristics) in images for comparison such that actual differences (e.g., changes in a physical characteristic of a patient) may be more accurately, efficiently, and easily discerned by a user.

Attribute: Any characteristic associated with a data item (e.g., a data item such as a medical exam, an image series, a medical image, and/or the like). Attributes may be inherited in a hierarchical manner. For example, a medical image may inherit attributes of an image series of which it is a part, and an image series may inherit attributes of a medical exam of which it is a part. Attributes may be stored as part of an associated data item (e.g., as metadata, DICOM header data, etc.) and/or separately from an associated data item. FIG. 13 illustrates various example attributes that may be associated with exams (e.g., example attributes 1306), image series (e.g., example attributes 1310), and images (e.g., example attributes 1314).

Sorting: A process of arranging images from multiple image series (and/or medical exams and/or other sources (e.g., Clinical Decision Support ("CDS") data, as described below)). In some embodiments, the process of sorting images from multiple image series may include generating a resultant "sorted" image series. While in some embodiments a sorted image series (including images from multiple image series) is generated, generation of a sorted image series is not necessary. Rather, in various embodiments, the process of sorting images may include determining an order of the images, which order may then be referenced when, for example, the images are displayed and/or viewed. For example, the system may simply reference pointers to images from multiple image series; the system may generate a "sorting metadata" file associated with the sorted series that indicates how images from multiple image series are sorted; and/or pointers to images from multiple image series may be determined in real-time as images are viewed in a sorted order. "Interleaving" is an example of a type of sorting of images in which images of multiple images series are regularly alternated. For example, in some embodiments, an interleaved image series comprises images from multiple image series ordered so that the interleaved image series alternates between the images of the original series. For example, when image series A comprising images A1, A2, ..., An, image series B comprising images B1, B2, ..., Bn, and image series C comprising images C1, C2, ..., Cn are interleaved, the resultant interleaved image series may be ordered: A1, B1, C1, A2, B2, C2, ..., An, Bn, Cn. Some embodiments and examples described below refer to "interleaving" of images, however other types of sorting may be used in those embodiments and examples. Images from multiple image series may be sorted in various patterns and multiple sortings may be determined from two or more image series. Images may be sorted based on one or more attributes associated with images, series, and/or exams. When images are sorted based on multiple attributes, a sorting of the images may be performed based on the attributes based on a priority of the attributes (as described below). Examples of sorting based on multiple attributes are described below in reference to, e.g., FIGS. 14-14B, 15A-15E.

Image Pane: Also referred to herein as "image frame," "viewing pane," "viewing frame," "comparison pane," "comparison frame," and/or simply "pane." A region of a computer display that may display an image.

Annotation: Any notes, measurements, links, assessments, graphics, and/or the like, associated with a data item, either automatically (e.g., by one or more CAP, described below) or manually (e.g., by a user). For example, when used in reference to a medical image, annotations include, without limitation, any added information that may be associated with the image, whether incorporated into an image file directly, comprising metadata associated with the image file, and/or stored in a separate location but linked to the image file in some way. Examples of annotations include measurements by using linear dimensions, area, density in Hounsfield units, optical density, standard uptake value (e.g., for positron emission tomography), volume, curved lines (such as the length of a curved vessel), stenosis (e.g., percent narrowing of a vessel at a certain location relative to a reference location), or other parameters. Additional examples of annotations include arrows to indicate specific locations or anatomy, circles, polygons, irregularly shaped areas, notes, and/or the like. Additional examples of annotations include arrows to indicate specific locations or anatomy, circles, polygons, irregularly shaped areas, notes, and/or the like. Further examples of annotations include graphics that, for example, outline lesions, lumbar discs, and/or other anatomical features.

Computerized Advanced Processing (CAP): Any computerized image analysis, image analysis technique, and/or image processing technique discussed herein, and/or any similar computerized processing technique that is currently or later available. CAP is described herein with regard to radiology images, but CAP and the systems and methods described herein may be applied in other areas including, but not limited to, other types of medical images (for example, cardiology, dermatology, pathology and/or endoscopy, among others), computer generated images (for example, 3D images from virtual colonoscopy, 3D images of vessels from CTA, and the like), images from other fields (for example, surveillance imaging, satellite imaging, and the like), as well as non-imaging data including audio, text, and numeric data. In some embodiments, CAP may include, but is not limited to, volume rendering (including, for example, multiplanar reformation/reconstruction (MPR), maximum intensity projection (MIP), 3D volume rendering, and/or 3D surface rendering), graphical processing/reporting (e.g., automated identification and outlining of lesions, lumbar discs etc.), automated measurement of lesions or other anatomical features, other image processing techniques, and/or the like.

User Input (also referred to herein as "Input"): As used herein in reference to user interactions with data displayed by a computing system, "user input" is a broad term that refers to any type of input provided by a user that is intended to be received and/or stored by the system, to cause an update to data that is displayed by the system, and/or to cause an update to the way that data is displayed by the system. Non-limiting examples of such user input include keyboard inputs, mouse inputs, digital pen inputs, voice inputs, finger touch inputs (e.g., via touch sensitive display), gesture inputs (e.g., hand movements, finger movements, arm movements, movements of any other appendage, and/or body movements), and/or the like. Additionally, user inputs to the system may include inputs via tools and/or other objects manipulated by the user. For example, the user may move an object, such as a surgical instrument, tool, stylus, or wand, to provide inputs. Further, user inputs may include motion, position, rotation, angle, alignment, orientation, configuration (e.g., fist, hand flat, one finger extended, etc.), and/or the like. For example, user inputs may comprise a position, orientation, and/or motion of a hand and/or a 3D mouse.

Data Store: Any computer readable storage medium and/or device (or collection of data storage mediums and/or devices). Examples of data stores include, but are not limited to, optical disks (e.g., CD-ROM, DVD-ROM, etc.), magnetic disks (e.g., hard disks, floppy disks, etc.), memory circuits (e.g., solid state drives, random-access memory (RAM), etc.), and/or the like. Another example of a data store is a hosted storage environment that includes a collection of physical data storage devices that may be remotely accessible and may be rapidly provisioned as needed (commonly referred to as "cloud" storage).

Database: Any data structure (and/or combinations of multiple data structures) for storing and/or organizing data, including, but not limited to, relational databases (e.g., Oracle databases, mySQL databases, etc.), non-relational databases (e.g., NoSQL databases, etc.), in-memory databases, spreadsheets, as comma separated values (CSV) files, eXtendible markup language (XML) files, TeXT (TXT) files, flat files, spreadsheet files, and/or any other widely used or proprietary format for data storage. Databases are typically stored in one or more data stores. Accordingly, each database referred to herein (e.g., in the description herein and/or the figures of the present application) is to be understood as being stored in one or more data stores.

III. Example Computing Devices and Systems

FIG. 1 is a block diagram showing various aspects of a computing system 150 and network environment 100 in which the computing system 150 may be implemented, according to various embodiments of the present disclosure. The computing system 150 may be referred to herein as the "data navigation system," the "medical image computing system," simply the "system," and/or the like.

As shown, the network environment 100 may include the computing system 150, a computer network 190, an image store 122, a server 120, a user preferences and rules database 124, one or more optional external sensors 125, one or more imaging devices 170, and/or a clinical decision support (CDS) server 171. As described below, in various embodiments the computing system 150, the image storage 122, the server 120, the user preferences and rules database 124, the external sensor(s) 125, the imaging devices 170, and/or the CDS server 171 may be in communication with one another via the network 190. In some embodiments, various of the image storage 122, the server 120, the user preferences and rules database 124, the external sensor(s) 125, the imaging devices 170, and/or the CDS server 171 may or may not be considered a part of the computing system 150. For example, in some embodiments one or more of these components may be implemented as part of the computing system 150, may be in direct communication with the computing system 150, and/or may be in indirect communication (e.g., over network 190) with the computing system 150.

The computing system 150 may include various components as shown and described in detail below. As described below, the computing system 150 may display images (including, e.g., medical images) and/or other data to a user via a display 155. The computing system 150 may include one or more sensors 161 (and/or one or more external sensors 125) that detect input from a user (e.g., gesture inputs via hand motion). Inputs may also be received via the input devices 156 described below. Sensors 161 may take various forms and may utilize, for example, cameras that utilize visible light, cameras that utilize infrared light, ultrasonic sensors, etc. Sensors 161 may be placed in a variety of positions that allow visualization of a body part to be monitored. As described below, in response to user input received by the computing system 150 (including, e.g., detected motion of a user's hand and/or other body part and/or inputs via the input devices 156), information displayed (e.g., medical images) may be updated.

Additional components of the computing system 150 may include, for example, one or more processors 152 and memory and/or data storage 153 (including one or more software modules 151 and/or a rules engine 163 (which may itself comprise a software module)). In particular, as described below, the rules engine 163 may execute various rules (for example, one or more rules stored in the user preferences and rules database 124) that may be used to translate various user inputs into corresponding changes of displayed images and/or other data. In another example, various rules of the user preferences and rules database 124 may indicate user preferences for sorting of images having certain attributes, automatic selection of images for comparison with a user selected image, preferences for registration of sorted and/or comparison images, selection of CDS data, and/or the like.

"Sorting rules" are referred to in reference to FIG. 14A below (and other figures herein). Such sorting rules may include any rules of the user preferences and rules database 124 that may be executed by the rules engine 163 to determine sorting of images. As described herein, sorting rules may include reference to one or more attributes of data (e.g., images, images series, exams, etc.) that are used to sort the data, such as to arrange a group of medical images in a particular sorting order. Sorting rules may define multiple levels of sorting based on respective attributes and/or combinations of attributes.

"Matching rules" are referred to in reference to FIG. 16 below (and other figures herein). Matching rules may include any rules of the user preferences and rules database 124 that may be executed by the rules engine 163 to determine sets of data (e.g., images, image series, exams, etc.) for comparison. For example, matching rules may be executed by the system so as to analyze imaging data (e.g., images, image series, exams, etc.) and determine data to compare, such as two or more exams, two or more image series, two or more images, etc. Examples of determining data for comparison are described in U.S. patent application Ser. No. 14/818,167, filed Aug. 4, 2015, and titled "SYSTEMS AND USER INTERFACES FOR AUTOMATED GENERATION OF MATCHING 2D SERIES OF MEDICAL IMAGES AND EFFICIENT ANNOTATION OF MATCHING 2D MEDICAL IMAGES," (the "'167 application"), the disclosure of which is hereby incorporated by reference in its entirety and for all purposes, as if set forth fully herein. Additionally, examples of determining data for comparison are described herein in reference to, for example, FIGS. 6, 14A, and 16.

Further, matching rules may also be used by the system to accomplish registration and/or matching of data (e.g., images, image series, exams, etc.) by adjustment of one or more image characteristics so as to remove artifactual differences, as described herein. For example, in some embodiments the system may include a registration and matching processor (and/or may include the described functionality within the computing system 150) that may automatically register and/or match images for more efficient comparison. Example systems and methods for registration and matching of images are described in the '167 application.

In various embodiments, any of the rules of the user preferences and rules database 124 (including, e.g., sorting rules and/or matching rules) may be selected based on, for example, one or more attributes of data displayed and/or an identifier or characteristic associated with a user. In various embodiments, any rules and/or particular sets of rules of the user preferences and rules database 124 may be associated with specific users, groups of users (e.g., a type of doctor, etc.), sites (e.g., a hospital, etc.), other characteristics of users, computing devices used the users, and/or the like. Thus, rules may be automatically selected by the system based on one or more characteristics associated with a user. In some embodiments, a default set of rules may apply to all user interactions, and/or when there are no rules specifically associated with the user. The various rules may be provided by the users themselves, by a system administrator, and/or they may be preprogrammed in to the system.

Additional components of the computing system 150 may include sensors 161, which may include, for example, motion sensors 159, orientation sensors 160, and/or location sensors 162. The various sensors 161 may include, for example, a camera (for example, video cameras, infrared cameras, and/or the like) or array of cameras capable of detecting (and/or providing data necessary for detecting) a position (including a location and/or orientation) and/or motion of the user's hand (or other gesture from the user). For example, sensors 161 may comprise a commercially available position sensor such as Microsoft's Kinect or Leap Motion's Leap Motion Controller. In various embodiments, one or more, or in some cases all, of the sensors 161 may be located as external sensors 125. In some embodiments, combinations of external sensors 125 and sensors 161 of the computing system 150 may be used for detecting user inputs.

In some embodiments, one or more sensors (for example, external sensors 125) may be attached and/or removably attached to the user, and/or may be located in tools or other objects operated by the user (e.g., a surgical instrument, tool, stylus, or wand, as described above) and such sensors may transmit information to the computing system 150 (through either a wired or wireless connection) such that the inputs of the user may be determined. For example, such sensors on the user may include gyroscopes (that may be used, for example, to detect and measure rotational motion), accelerometers (that may be used, for example, to detect and measure linear motion), compasses, Global Positioning System (GPS) transceivers and devices, near field communication (NFC) technology devices, Radio Frequency Identification (RFID) devices, systems and devices utilizing WiFi, systems and devices utilizing Bluetooth such as iBeacons, and/or the like. In another example, a position transmitter may be used to track the location, position, movement, and/or orientation of the user and/or the user's body parts (e.g., the user's hand). Such a position transmitter may transmit a position and/or motion of, e.g., the user's hand and/or an input device, to one of the external sensors 125. In some embodiments position information from the external sensors 125 may supplement position information from the sensors 161. In other embodiments, a user inputs may be determined based on only information from sensors 161 or based on only information from external sensors 125.

The various sensors and transmitters (e.g., any combination of the sensors described above) may provide input data to the computing system 150 such that inputs from the user may be detected and/or determined. Such input data may be processed by, for example, one or more software modules 151 of the computing system 150 and/or other components of the system, as described below, such that displayed image data and/or other displayed information may be updated.

As further described below, network environment 100 may include a server 120 that provides information that is displayed by computing system 150. Network environment 100 may include image storage 122 (for example, a data store, database, and/or storage system) that may be configured to store image information, such as image data (also referred to herein as image and/or imaging information) (for example, images (e.g., two-dimensional (2D) images), image series, three-dimensional (3D) imaging data, medical imaging exams, and/or the like), that is processed by server 120 and/or computing system 150. In various embodiments, image data is stored in Digital Imaging and Communications in Medicine ("DICOM") format and/or any other appropriate format. Network environment 100 may also include user preferences and rules database 124 which may store user, group, or site preferences and rules that determine the operation of various embodiments as described herein. Additionally, user preferences and rules database 124 may include various rules that are used by the system to translate user inputs into corresponding movement of displayed images and/or other data, as described below.

In some embodiments, user preferences and rules database 124 may be used to store particular rules and preferences to apply to medical imaging data (or other data types in other embodiments) for particular users. For example, certain rules may be preferred by certain users and/or groups of users. Accordingly, preferences associated with those certain users and/or groups of users may indicate that the certain rules are to be applied such that, for example, certain types of images are to be sorted (and/or selected for comparison) based on certain attributes of those images. As discussed in further detail below, the rules and preferences of the user preferences and rules database 124 may vary depending of the type of image, area imaged, clinical indication, source of image, display device, user, or other factors. Accordingly, any type of user preferences and/or rules are expressly contemplated for use in conjunction with the systems and methods described herein.

In various embodiments, the functionality provided by image storage 122, server 120, CDS server 171, and/or user preferences and rules database 124 may reside within computing system 150.

The imaging devices 170 may include any devices capable of obtaining images for use by the system. For example, imaging devices 170 may include one or more medical scanners, such as X-Ray scanners, MRI scanners and/or CT scanners (as further described below).

The clinical decision support (CDS) server 171 may provide any type of imaging and/or other data (referred to herein a clinical decision support (CDS) data) to the computing system 150 that may be useful for analysis and evaluation of images by a user (e.g., for more efficient diagnosis of medical conditions). Determination of CDS data may be by execution of one or more rules of the user preferences and rules database 124. For example, the CDS server may, in response to a request by a user for CDS data in relation to a series of medical images, analyze one or more characteristics associated with a patient from which the series was obtained. The CDS server 171 may then determine, based on the analysis, a comparison series of images comprising images of a "normal" patient having similar characteristics. The determined comparison series may then be provided and sorted with (or, alternatively, displayed alongside) the series of medical images. Accordingly, the comparison series and the series of medical images may be compared and evaluated. As described above, certain rules may be executed based on a user, group, site, and/or the like. Thus, a doctor with a particular specialty may receive different CDS data from the CDS server 171 than a doctor with a different specialty. Accordingly, the CDS server 171 may enable more efficient diagnosis of patients. As mentioned, the CDS server 171, and/or the functionality of the CDS server 171, may, in some embodiments, be included in the computing system 150.

IV. Example User Interfaces for Comparison of Images

Figure 2:
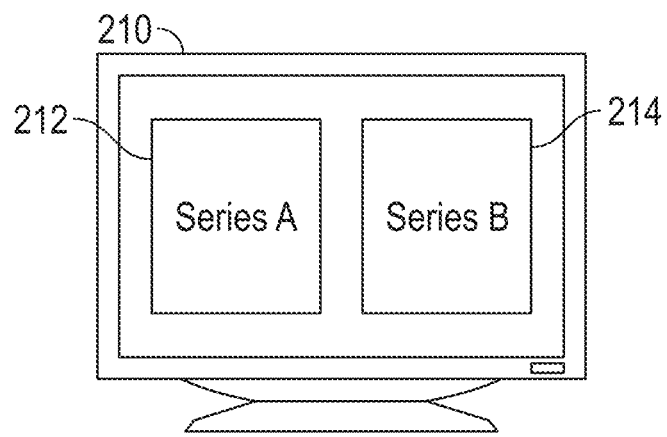
FIG. 2 is a diagram illustrating a display device of the system having images from two image series concurrently displayed in image panes displayed on the display device, according to an embodiment of the present disclosure.

FIG. 2 is a diagram illustrating a display device of the system having images from two image series concurrently displayed in image panes 212 and 214 displayed on the display device 210, according to an embodiment of the present disclosure. In the discussion that follows, the display device 210 is coupled to a computing device, such as computing system 150, and receives display information from the computing system 150. While the systems and methods described below for sorting (including, e.g., interleaving) and viewing images of multiple image series may be controlled by any suitable computing device, for ease of explanation herein, reference will be made to a display device coupled to computing system 150.

In the embodiment of FIG. 2, an image of a series A image series is displayed in the image pane 212, while an image of the series B image series is displayed in the image pane 214. As noted above, each image series comprises a group of images that are related in some way, such as having been acquired from a patient on a particular day. Although only a single image of each of the image series is simultaneously displayed on the display device 210, the series A and series B image series each comprise multiple images.

In some embodiments, such as where the series A and B images are related, e.g., series A comprises mammogram images of a patient taken on a first date and series B comprises the mammogram images of the same patient taking on a later date, it may be advantageous to identify differences between the images of series A and series B. For example, if a lung radiograph from two months previous, and a current lung radiograph are to be compared in order to determine if any changes have occurred in the lungs over the previous two months, the viewer or reader may view the two x-rays side by side, such as in image panes 212 and 214 as illustrated in FIG. 2. Accordingly, in some embodiments described herein, are example systems and methods for comparison of images of multiple image series so that differences between the images may be determined. In certain embodiments, related images are displayed side-by-side in multiple viewing panes and/or sequentially in a single viewing pane (and/or sequentially in multiple viewing panes) on a display device so that difference between the images may be detected by a user. The systems and methods described herein are applicable to any two or more images, including multiple images of multiple image series, for example.

Figure 3:
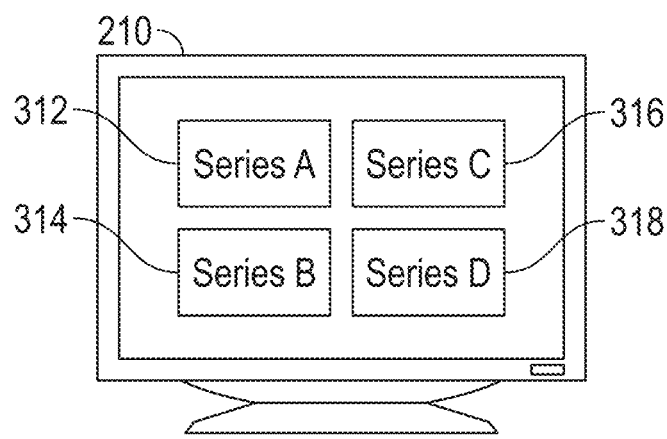
FIG. 3 is a diagram illustrating a display device of the system having images from four image series concurrently displayed in image panes displayed on the display device, according to an embodiment of the present disclosure.

FIG. 3 is a diagram illustrating a display device of the system having images from four image series concurrently displayed in image panes 312, 314, 316, and 318 displayed on display device 210, according to an embodiment of the present disclosure. In the embodiment of FIG. 3, the image pane 312 displays images from series A, the image pane 314 displays images from series B, the image pane 316 displays images from series C, and the image pane 318 displays images from series D. Thus, a single image from each of the four image series A-D is concurrently displayed on the display device 210. Accordingly, comparison of images of multiple series may be performed using a graphical user interface such as displayed in FIG. 3, wherein the user distinguishes differences between images that are displayed side-by-side on a display device.

V. Example User Interfaces and Interactions for Comparison of Sorted Images

Figure 4:
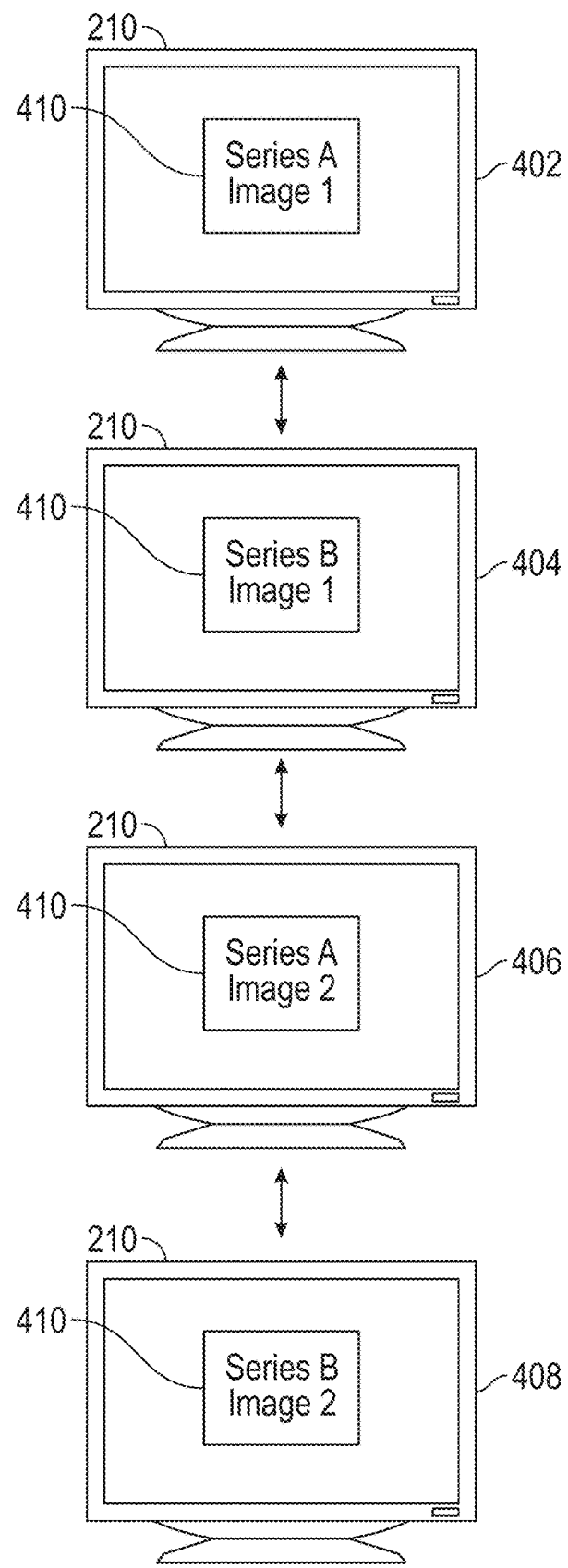
FIG. 4 is a diagram illustrating sequential changes to a comparison image pane displayed on the display device of the system as images from two image series are compared, according to an embodiment of the present disclosure.

FIG. 4 is a diagram illustrating sequential changes to a comparison image pane 410 displayed on the display device

210 of the system as images from two image series are compared, according to an embodiment of the present disclosure. The comparison pane 410 is configured to display a single image. In an embodiment, a display pane of the system, e.g. display pane 312 on display device 210, serves as the comparison pane 410. In the embodiment of FIG. 4, images from two image series, images series A and B, have been selected for comparison. After being selected for comparison using any suitable selection method, images from series A and B are interleaved so that they are alternatively displayed in the comparison pane 410.

In embodiments with more than two series, the interleaved images may be ordered according to various schemes and based on various attributes, as described below. For example, images from four image series may be ordered as follows: first image of first image series, first image of second image series, first image of third image series, first image of fourth image series, second image of first image series, and so forth. In other embodiments, however, the interleaved images may be ordered differently. For example, images from four image series may also be ordered as follows: first image of first image series; first image of second image series; first image of first image series; first image of third image series; first image of first image series; and first image of fourth image series. While some of the description above and below refers to "interleaving," any other sorting of images from multiple image series falls within the scope of the present disclosure. For example, images may be sorted based on attributes other than image number, and may further be sorted based on multiple attributes, as described below in reference to FIGS. 14-14B, 15A-15E.

FIG. 4 shows the display device 210 at four states 402, 404, 406, and 408 of the comparison process, where the comparison process describes the process of displaying images in an interleaved image series. More particularly, at state 402, a first image of image series A is displayed in the comparison pane 410. Moving to state 404, the first image of image series A is replaced by a first image of image series B in the comparison pane 410. Assuming the images of series A and B are of the same subject, the image displayed in blocks 402 and 404 may be very similar. Accordingly, if differences exist in the first images of series A and B, these differences may be more easily detectable as the display device cycles between the two images. Comparison of images in an interleaved image series may be more advantageous if the images of each selected image series are of a common anatomical area, common image size, common image orientation, and the images are in the same order. Accordingly, in an embodiment images of the interleaved image series may be registered and/or matched such that the interleaved images match in regards to one or more image characteristics to reduce and/or eliminate artifactual differences.

In one embodiment, the computing system 150 that is coupled to the display 210 may store settings for displaying images of particular image series, such as, for example, time for displaying each image, resolution of each image, cropping to be applied to each image, and any other setting that maybe appropriate. In one embodiment, the time for displaying an image may be determined real time by the user. For example, the user may press a designated key on a keyboard or mouse, and/or provide other user input (as described above) in order to indicate that the current image should be replaced with an adjacent image in the interleaved image series. In another embodiment, the user selects settings for display of the images. For example, the user may select an appropriate zoom level of an image series that should be applied to each image in the image series.

Thus, the images of series A may be magnified more or less than the images of series B. In addition, the user may adjust any other visualization settings for individual images, an entire image series, or two or more image series. In an embodiment, as described above and below, the system may automatically register and/or match images for more efficient comparison.

With the first image of series B displayed in the comparison pane 410 (state 404), the user may initiate viewing of an adjacent image in the interleaved image series by pressing a certain key on a keyboard or mouse, or by other user input, for example. In an embodiment, a first input from a mouse indicates that a next image, e.g. image 2 of series A (state 406), should be displayed in the comparison pane 410, and a second input from the mouse indicates that a previous image, e.g. image 1 of series A (state 402), should again be displayed in the comparison pane 410. In one embodiment, the first input is entered by the user moving a scroll button on the mouse in a first direction and the second input is entered by the user moving the scroll button on the mouse in an opposite direction. In another example, the first and second user inputs may be provided by gestures (e.g., the user moved their hand right or left in front of the display 210). Thus, the user may change the content of the comparison pane 410 to either a next or a previous image in the interleaved image series. For example, at state 404, if the user wishes to again view the first image of series A, e.g., in order to locate difference in the first images of series A and B, the user may provide an input to the computing system 150 indicating movement to a previous image. Alternatively, at state 404, if the user wishes to view a next image in the interleaved image series, the user may provide an input to the computing system 150 indicating movement to a next image.

At state 406, the second image of series A is displayed in the comparison pane 410, replacing the first image of series B (state 404). At state 406, the user may provide inputs to the computing system 150 indicating that the comparison pane 410 should be updated with a previous image, e.g. state 404, or a subsequent image, e.g., state 408.

At state 408, the second image of series B is displayed in the comparison pane 410, replacing the second image of series B (state 406). At state 406, the user may provide inputs to the computing system 150 indicating that the comparison pane 410 should be updated with a previous image, e.g. state 404, or a subsequent image. In one embodiment, each of the image series A and B include more than two images, such as 3 or more images, and the images of series A and B are displayed in the manner described above with respect to FIG. 4. In one embodiment, more than two images series may be interleaved for display in the comparison pane. For example, if three images series, e.g., series A, B, and C, are selected for comparison, a first image of each of the series may be sequentially displayed in the comparison pane, followed by a second image of each of the series, and so on. As noted above, the user may control the timing of transition between display of images in the interleaved image series and may even control the direction of movement in the interleaved series. Additionally, the user may control alignment and/or positioning of the images of each images series in order to precisely align interleaved images from multiple series.

Accordingly, in some embodiments, the images of each of the image series are automatically modified (e.g., registered and/or matched) so that image characteristics of the images are similar. For example, images may be adjusted by changing their size, rotation, and location. If the images are of substantially the same anatomical structure, when the images of the interleaved image series are displayed in the comparison pane, differences between adjacent images may be more easily detected. In one embodiment, selected images are morphed in order to achieve a common size of the anatomical structure of interest in each of the images. In one embodiment, photographic filters may be applied to all images of one or more image series, or to selected images of one or more image series, to further enhance the viewer's ability to distinguish differences in the images.

In one embodiment, information regarding the image currently displayed in the comparison pane 410 is displayed on the display device 210 and updated as the images in the comparison pane 410 are changed. For example, information regarding the images series and image number within the series may be displayed for each image. In addition, the exam date and time may also be displayed and updated as the images of the interleaved image series are displayed in the comparison pane 410. In one embodiment, an indicator of whether the current display is of an interleaved image series or a single image series is displayed on the display device. For example, "interleaved" or "sorted" may be displayed at the top of the display device when an interleaved image series is displayed in a comparison pane. In some embodiments, the user may choose what information related to the images of the interleaved image series should be displayed. The user may also be provided the ability to turn the display of information on and off, such as by pressing a particular key or key combination on the keyboard.

Figure 5:
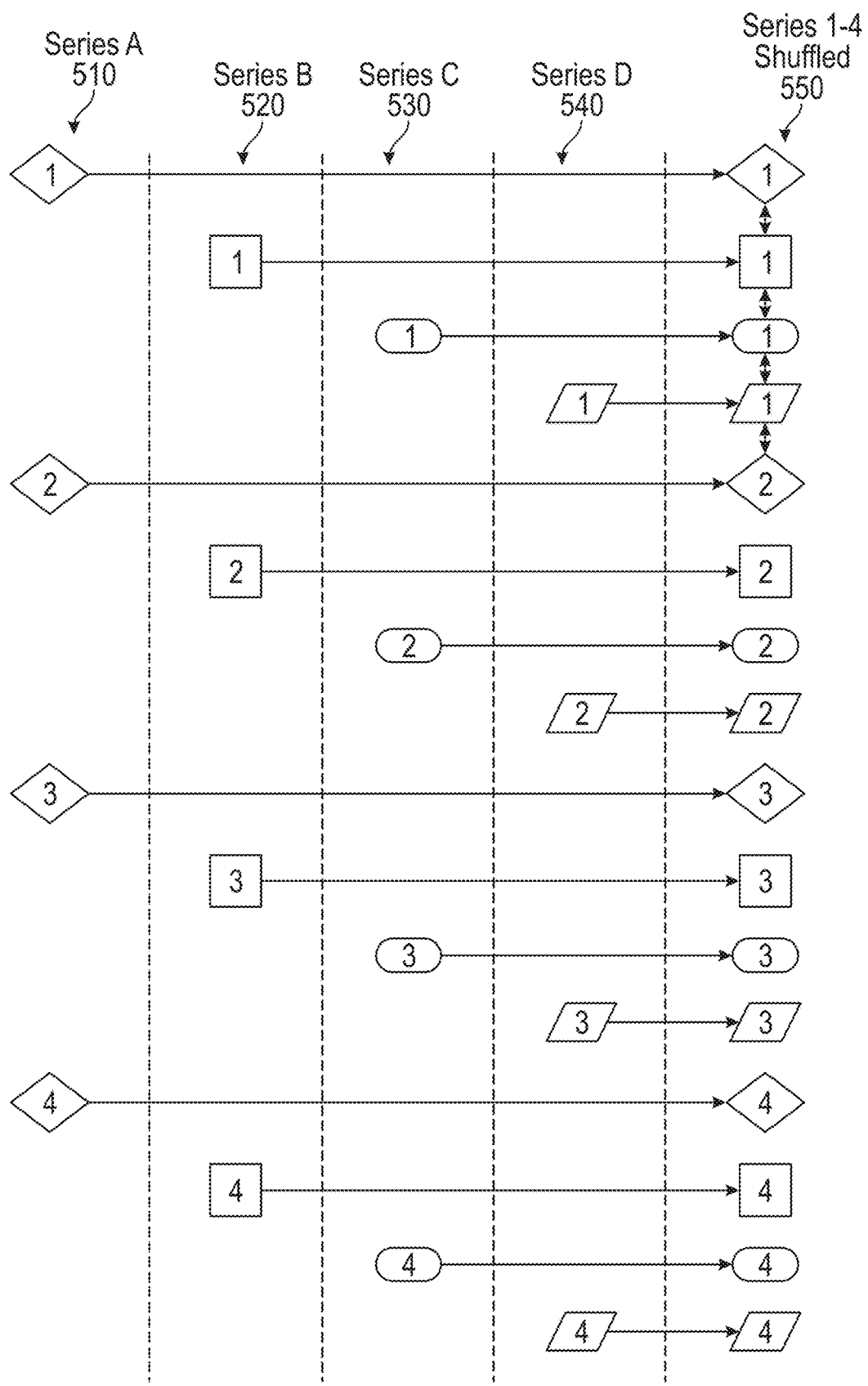
FIG. 5 is a diagram illustrating an example interleaving of four image series, according to an embodiment of the present disclosure.

FIG. 5 is a diagram illustrating an example interleaving of four image series in creating an interleaved image series, according to an embodiment of the present disclosure. As noted above, the image series that are selected for comparison, and thus, are selected for interleaving, may be selected by a user in one of several manners or may be automatically selected by the system based on properties of the image series. In one embodiment, the multiple image series are interleaved. For example, a first image of each series may be displayed in the comparison pane prior to display of a second image of any of the other selected image series. In other examples, the multiple image series may be interleaved based on one or more attributes, as described below in reference to FIGS. 14-14B, 15A-15E. FIG. 5 illustrates an exemplary interleaving of four image series, series A, B, C, and D, each comprising four images. As those of skill in the art will recognize, more or fewer image series, each comprising more or fewer images, may be interleaved in a manner similar to that illustrated in FIG. 5.

In FIG. 5, the images of series A are represented by diamonds in a column 510, where a number in each of the diamonds represents a specific image within image series A. Similarly, images of series B are represented by squares in column 520, series C are represented by ovals in a column 530, and series D are represented by parallelograms in a column 540. Each of the images in images series B, C, and D are likewise numbered 1-4, indicating a particular image in each image series. As noted above, the first image selected for comparison in a particular image series may not be the first image in the image series, e.g., the first image of an exam. Thus, although each image series A-D begins with a first image labeled image "1", this first image may not be the first image in the image series, but may be a user selected, or automatically selected, start image. In addition, each of the images may have user-defined image characteristics that are different than other images of the same series and/or other image series. In some embodiments, image characteristics, such as zoom level, cropping, and color characteristics (among others, as described above), may be simultaneously changed for each image in an image series, such as series A, B, C, D, or an interleaved image series, such as interleaved image series 540. In some embodiments, images of the interleaved image series may be automatically registered and/or matched to remove artifactual differences between comparison images.

As illustrated in FIG. 5, an interleaved image series 550 includes each of the images 1-4 in each of the image series A-D. More particularly, the interleaved image series 550 comprises a first image from each of series A-D, followed by a second image from each of the series A-D, followed by a third image from each of the series A-D, followed by a fourth image from each of the series A-D. Thus, when the interleaved image series 550 is displayed in the comparison pane, a first image of the image series A is displayed, followed by a first image of image series B, a first image of image series C, and a first image of image series D. While the order of the interleaved image series 550 is maintained during viewing of the interleaved images, the direction of movement between adjacent images may be selected by the user or automatically by the computing system 150.

In an embodiment, the interleaving described above in reference to FIG. 5 may understood as interleaving based on two attributes, in order of priority: 1. Image number, and 2. time of acquisition. For example, image series A may have been acquired first, image series B may have been acquired second, image series C may have been acquired third, and image series D may have been acquired last. Thus, interleaving the four images series may be accomplished by, first, grouping the images by image number (e.g., all image 1's go together, all image 2's go together, etc.), and then ordering the grouped images by time of acquisition such that the earliest acquired is first (resulting in a sorting order: series A image 1, series B image 1, series C image 1, series D image 1, series A image 2, etc.)

FIG. 6 is a flowchart illustrating an example method of viewing images from multiple image series, according to an embodiment of the present disclosure. Using the method of FIG. 6, multiple image series may be easily compared and differences between images of the multiple image series may be distinguished. Depending on the implementation, the system may perform methods having more and/or fewer blocks than are shown, and/or the blocks may occur in a different order and/or in parallel in order to accomplish certain methods and/or processes of the system. In an embodiment, one or more blocks in the flowchart may be performed by, or implemented in, one or more computer modules and/or processors, as is described above and below with reference to FIG. 1.

In block 610, a first image series is selected. As noted above, an image series is a group of two or more images that are in some way related. For example, a first image series may comprise multiple chest x-rays of a patient that are taken on a given date.

In block 620, one or more comparison image series are selected. These image series also each comprise two or more images that are in some way related, such as having been taken at a common exam. The comparison image series may be related to the first image series so that when the first image series and the comparison image series are compared, meaningful distinctions between the image series may be detected. As described below in reference to FIG. 14A, in some embodiments image series and/or medical exams for comparison may be automatically selected by the system based on one or more matching rules.

In one embodiment, the first image series and the comparison image series are selected by the user clicking on a button indicating that image sorting is desired. In one embodiment, a user right-clicks with a mouse on an image of a first image series in order to initiate display of an "interleave menu" or "sort menu" listing options for selecting image series for sorting and viewing the sorted image series. In one embodiment, the interleave menu includes an option, such as "interleave adjacent," indicating that the user may select one of the other image series displayed on the display for interleaving. In certain embodiments, any number of image panes may be simultaneously displayed on the display device 210. For example, in FIG. 2, two image panes 212 and 214 are displayed and in FIG. 3, four image panes 312, 314, 316, and 318 are displayed. In other embodiments, six, eight, ten, twelve, or more image panes may be concurrently displayed on the display device.

When the "interleave adjacent" option is selected, the user may select one or more comparison series by moving the pointer to a border between the adjacent series and clicking the mouse button. In one embodiment, the cursor icon changes when it is positioned in a border indicating that the adjacent image series may be selected for comparison by clicking the mouse button. With reference to FIG. 3, for example, the user may right click on the image pane 314 in order to select series B as the first image series and to initiate display of the interleave menu. From the interleave menu, if the user selects interleave adjacent, the user may then move the pointer to the border between the image panes 312 and 314 and click the mouse button in order to select series A as a comparison image series. In one embodiment, selecting a comparison image series initiates creation of an interleaved image series and displays the first image of the interleaved image series in the comparison pane. In an embodiment when only two image series are represented on the display device, such as FIG. 2, selection of interleave adjacent from the interleave menu may automatically select the two displayed image series for interleaving and initiate creation and viewing of a interleaved image series.

In one embodiment, the interleave menu also includes an option that allows the user to select an adjacent image series for interleaving and, after selection of the first and comparison image series, displays images of the interleaved images series in a comparison pane that covers the entire display area, or substantially all of the display area, of the display device. In this way, the images of the selected image series may be viewed at a higher magnification level and, accordingly, differences in the images may be more easily detectable. Thus, in an embodiment that displays four image panes on the display device (e.g., FIG. 3), after selection of this option from the interleave menu, a single click on a comparison image series may cause the computing device to generate an interleaved image series and display a first image of the interleaved image series in a comparison pane that covers substantially all of the display area of the display device, e.g., the area previously covered by the four image panes 312, 314, 316, and 318 of FIG. 3. Advantageously, this "interleave and jump to full screen display" option on the interleave menu provides an efficient transition from display of many image series to the display of a single interleaved series in a comparison pane that covers all, or substantially all, of the display area of a display device.

In one embodiment, the interleave menu includes an option that initiates automatic selection of one or more comparison image series based upon attributes of the selected first image series. For example, image series with the same or similar names may be selected as comparison image series. In addition, image series may be selected automatically based upon any other criteria, such as one or more information items contained in the DICOM headers of images. In one embodiment, when this option is chosen from the interleave menu, a list of image series that have the same series name, or other criteria that may be user defined, may be displayed. The user may then select one or more of the displayed series as comparison image series.

The interleave menu advantageously allows the user to select image series for interleaving and automatically display the generated interleaved image series with minimal input from the user. For example, after selecting "interleave adjacent" on the interleave menu, a single click of a mouse, for example, on a border between the images to be interleaved causes the computing system 150 to generate an interleaved image series and display a first image of the interleaved image series in a comparison pane on the display device.

In an embodiment, the user may initiate sorting of image series by selection of a button as described below in reference to the user interface of FIG. 18C. In the embodiment of FIG. 18C, functionality similar to that described above applied. For example, images of series for comparison may be automatically sorted, registered and/or matched, and displayed in an enlarged window of the display.

Returning to the diagram of FIG. 6, in a block 630, a starting image of each of the image series is selected. In one embodiment, a first image of the first image series and each of the comparison image series are displayed on a display device. A user, providing a user input via using an input device, such as a mouse or keyboard, and/or another input method, may cycle through the images in each of the image series in order to determine a first image for comparison. For example, images of certain modalities, such as CT and MRI images, may not have starting images that are each taken at similar physical locations within the patient. Thus, in these embodiments the user may select a different starting image in each of the image series so that adjacent images in the interleaved image series are more closely related. For example, if the images series to be interleaved are series A comprising images A1, A2, . . . , An, series B comprising images B1, B2, . . . , Bn, and series C comprising images C1, C2, . . . , Cn, the user may select images A1, B3, and C5 as the starting images of the respective image series so that the resultant interleaved image series is ordered A1, B3, C5, A2, B4, C6, A3, B5, C7, . . . Ax, Bx+2, Cx+4.

In an advantageous embodiment, the starting image in each of the series should be related so that meaningful differences between the images of the image series are detectable. In one embodiment, the user may adjust image characteristics of each image in an image series by adjusting the image characteristics of the image currently displayed from the desired image series. For example, if the first image series is at a higher zoom level than the comparison image series, the zoom level of each image in the first image series may be adjusted by adjusting the zoom level of the currently displayed image of the first image series.

After selecting the first image series and the comparison image series, and selecting the image characteristics of one or more of the images which are then applied to the other images in the series to which it belongs, the image series are interleaved so that an interleaved image series is created, as illustrated in FIG. 5, for example.

In a block 640, images from the interleaved image series are displayed in a comparison pane displayed on the display device. In one embodiment, the comparison pane fills substantially the entire display area of a display device. In another embodiment, the comparison pane is smaller than a total display area of the display device. In one embodiment, a user input determines when a current image displayed in the comparison pane is updated with an adjacent image, by moving a scroll wheel on a mouse while pressing a mouse button, for example. In one embodiment, when the user has completed viewing the interleaved image series, the previous layout on the display device may be restored by the user performing a specific action, such as releasing the mouse button that is depressed while viewing interleaved images.

In various embodiments, as mentioned above, images to be interleaved may be reconstructed and/or rendered from volumetric imaging data via one or more of the CAP method described above. In some instances, two exams comprising volumetric image data may be selected for comparison, and matching images may then be reconstructed and/or rendered for interleaving. In other instances, a set of volumetric imaging data may be selected for comparison with an existing image series, and a comparison image series may then be reconstructed/rendered and matched from the set of volumetric imaging data.

Figure 8A:
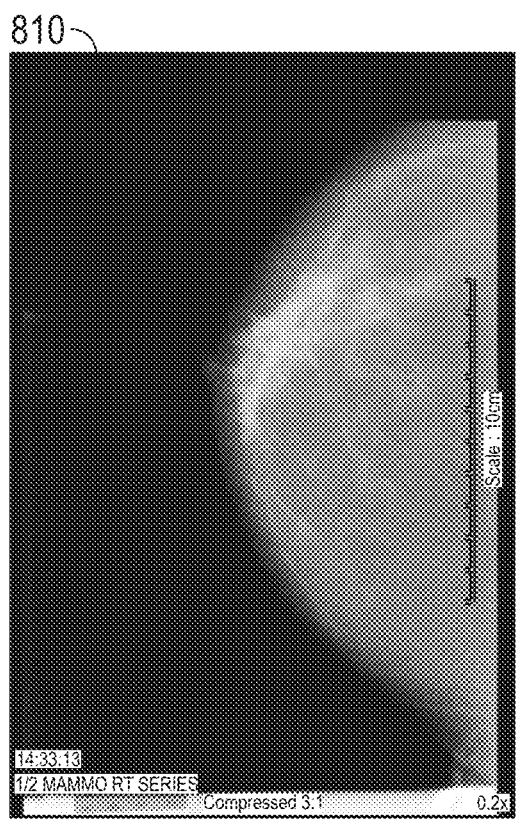
FIGS. 8A and 8B are example images of a second image series.
Figure 8B:
Figure 9:
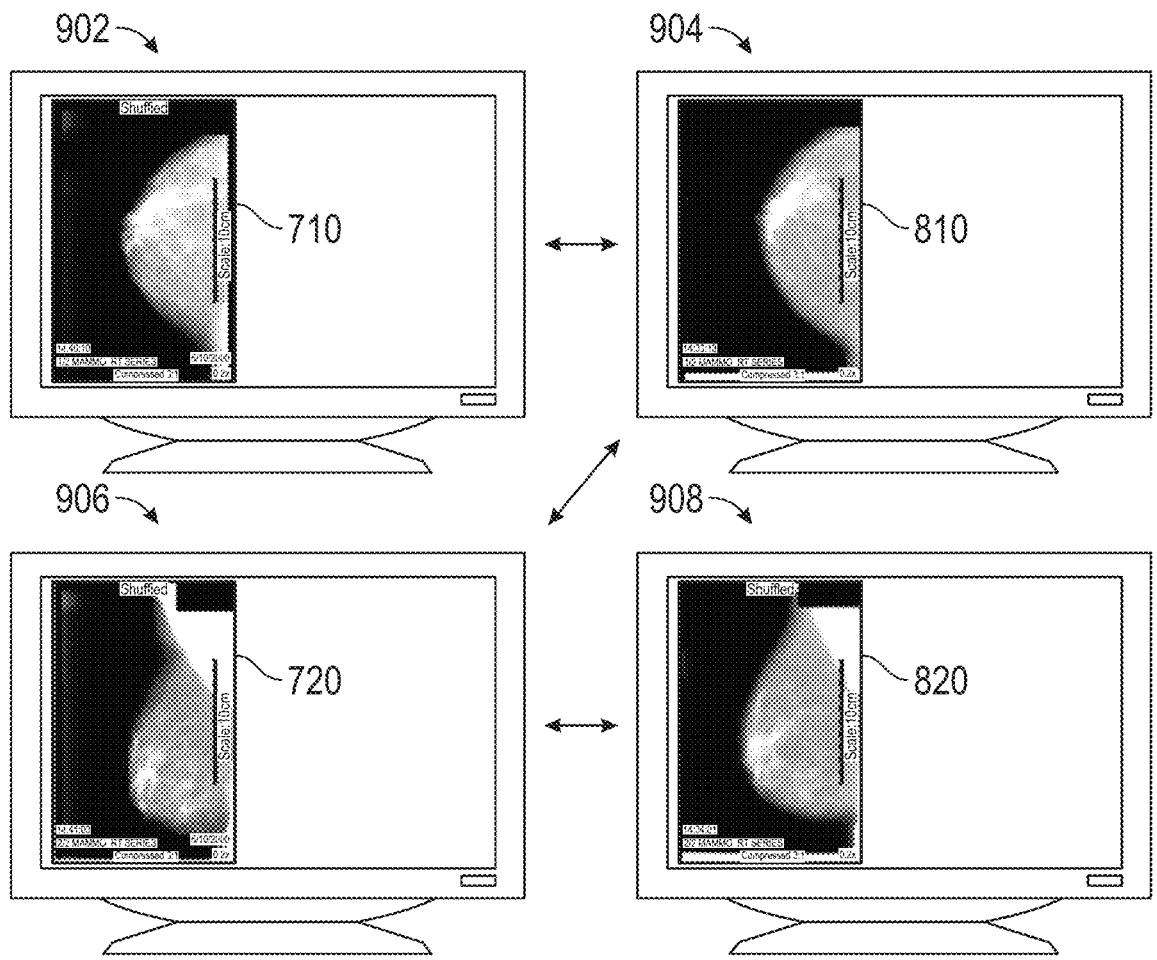
FIG. 9 illustrate an example of the images of the first and second image series being interleaved for sequential viewing in a predetermined portion of a display, according to an embodiment of the present disclosure.

FIGS. 7A and 7B are example images of a first image series, FIGS. 8A and 8B are example images of a second image series, and FIG. 9 is a diagram illustrating an example of the images of the first and second image series being interleaved for sequential viewing in a predetermined portion of a display, according to an embodiment of the present disclosure. More particularly, FIGS. 7A and 7B are two mammographic images 710 and 720 in a first image series. In one embodiment, the images 710 and 720 are obtained by imaging of a patient on a first date. FIGS. 8A and 8B are two mammographic images 810 and 820 in a second image series. In one embodiment, the images 710, 720, 810, and 820 are of the same patient, but the images 810 and 820 were obtained at a later date than the images 710 and 720. Thus, differences between the earlier mammographic images 710 and 720, and the later mammographic images 810 and 820 may be useful in detection and diagnosis of the patient. Accordingly, comparison of the images of the images series illustrated in FIGS. 7A-7B and 8A-8B may allow detection of differences between the earlier and later images.

FIG. 9 shows the images of FIGS. 7A-7B and 8A-8B combined in an interleaved image series for viewing in a comparison pane. For example, in state 902, image 710 may first be displayed in a comparison pane. When the user indicates that a next image should be displayed, in state 904, image 810 replaces image 710 in the comparison pane. With image 810 displayed in the comparison pane, when the user indicates that a next image should be displayed, in state 906, image 720 replaces image 810 in the comparison pane. With image 720 displayed in the comparison pane, when the user indicates that a next image should be displayed, in state 908, image 720 is replaced with image 820 in the comparison pane. As noted above, however, movement between images in an interleaved image series, such as that of FIG. 9, may be bidirectional so that the user may move back and forth between images as desired.

In another embodiment, interleaving of image series produces two or more interleaved image series. In one embodiment, images of a first interleaved image series may be alternatively displayed in a first comparison pane of the display device, while images of a second interleaved image series may be alternatively displayed in a second comparison pane of the display device, and so on. For example, if the image series to be interleaved are series A comprising images A1, A2, and series B comprising images B1, B2, the system may generate a first interleaved series ordered A1, B1, and a second interleaved image series ordered A2, B2. In one embodiment, images from each from each of the first and second interleaved image series are concurrently displayed on a display device in separate comparison panes. In one embodiment, an option on the interleave menu, discussed above, may be selected in order to initiate generation of multiple interleaved image series and concurrent display of multiple comparison panes on the display device. In one embodiment, more than two images of image series may be interleaved in the above-described manner and more than two comparison panes may be displayed concurrently on a display device for viewing the generated interleaved image series.

Figure 10:
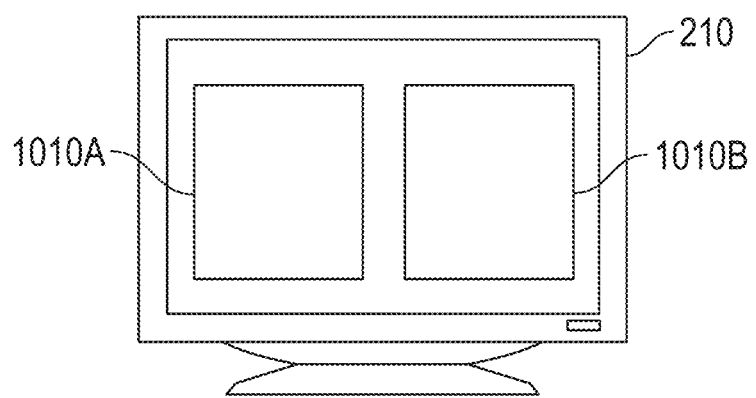
FIG. 10 is a diagram illustrating a display device displaying two comparison panes, according to an embodiment of the present disclosure.

FIG. 10 is a diagram illustrating a display device displaying two comparison panes 1010A and 1010B, according to an embodiment of the present disclosure. As noted above, multiple interleaved or otherwise sorted image series may be concurrently displayed on the display device 210 in separate comparison panes. In another embodiment, the display device 210 displays three or more comparison panes for concurrently displaying three or more sorted image series.

Figure 11:
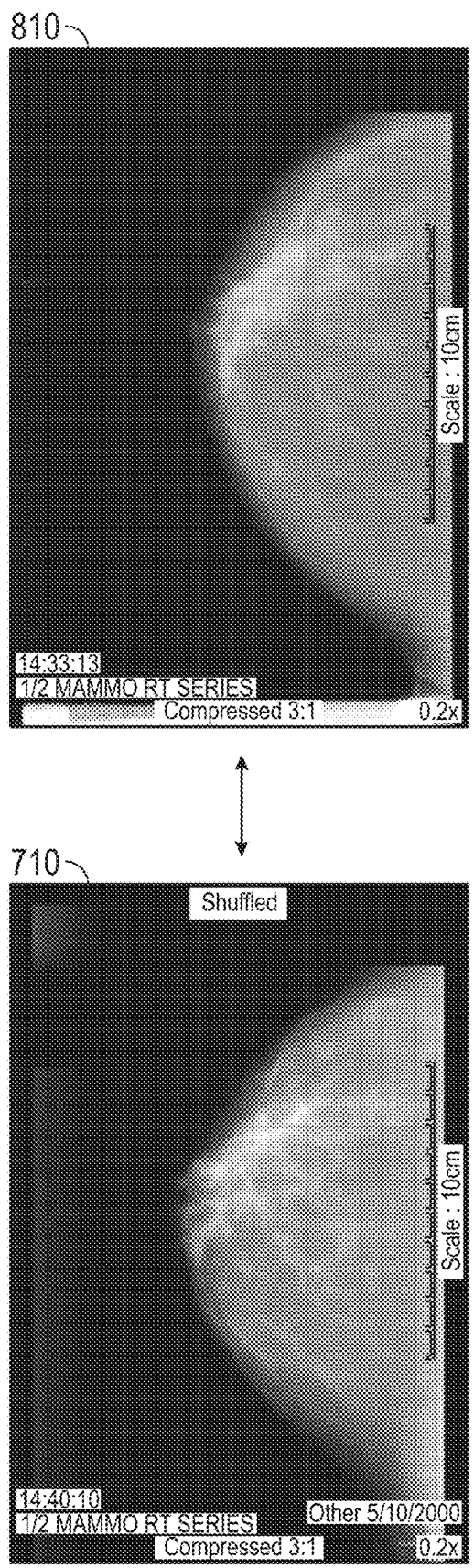
FIG. 11 illustrates the first images of the first and second image series illustrated in FIGS. 7A and 8A interleaved for alternative viewing in a comparison pane, according to an embodiment of the present disclosure.
Figure 12:
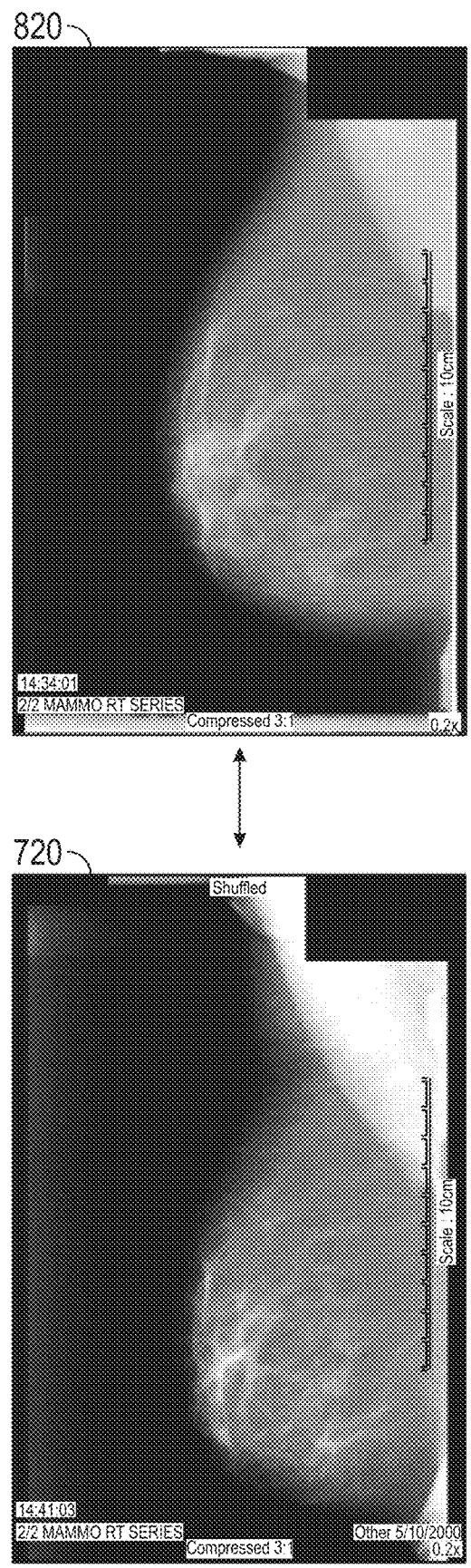
FIG. 12 illustrates the second images of the first and second image series illustrated in FIGS. 7B and 8B interleaved for alternative viewing in a comparison pane, according to an embodiment of the present disclosure.

FIG. 11 illustrates the first images 710 and 810 of each of the first and second image series illustrated in FIGS. 7A and 8A, and FIG. 12 illustrates the second images 720 and 820 of each of the first and second image series illustrated in FIGS. 7B and 8B. The images 710 and 810 (FIG. 11) comprise a first interleaved image series, while the images 720 and 820 (FIG. 12) comprise a second interleaved image series. In the embodiment illustrated in FIGS. 11 and 12, the images 710 and, 720 are from a first exam and the images 810 and 820 are from a second exam. However, the first selected images from each exam, e.g., images 710 and, 810, are of a first projection, while the second selected images from each exam, e.g., 720 and 820, are of a second projection (and/or they match with regards to another attribute). Thus, it may be advantageous for an interpreter of the images to view the images of the same projection, from different exams, in separate interleaved image series. Accordingly, in the embodiment of FIGS. 10, 11, and 12, a first interleaved image series comprising images 710 and 810 are viewed in a first comparison pane 1010A while a second interleaved image series comprising images 720 and 820 are viewed in a second comparison pane 1010B. In this embodiment, the viewer may advantageously move between images of the same projection in a comparison pane in order to identify differences in the images, while also viewing images of one or more additional projections in additional comparison panes. In one embodiment, any number of images may be included in each of the interleaved images series displayed in comparison panes 101A and 1010B, and additional comparison panes may be concurrently displayed on the display device 210.

As mentioned above, the inventors have found that users using the system to flip through medical images (e.g., to analyze the images and perform diagnoses based on the images) are faster (e.g., 15% faster or more) and more accurate than users using traditional methods of comparing images.

Figure 14A:
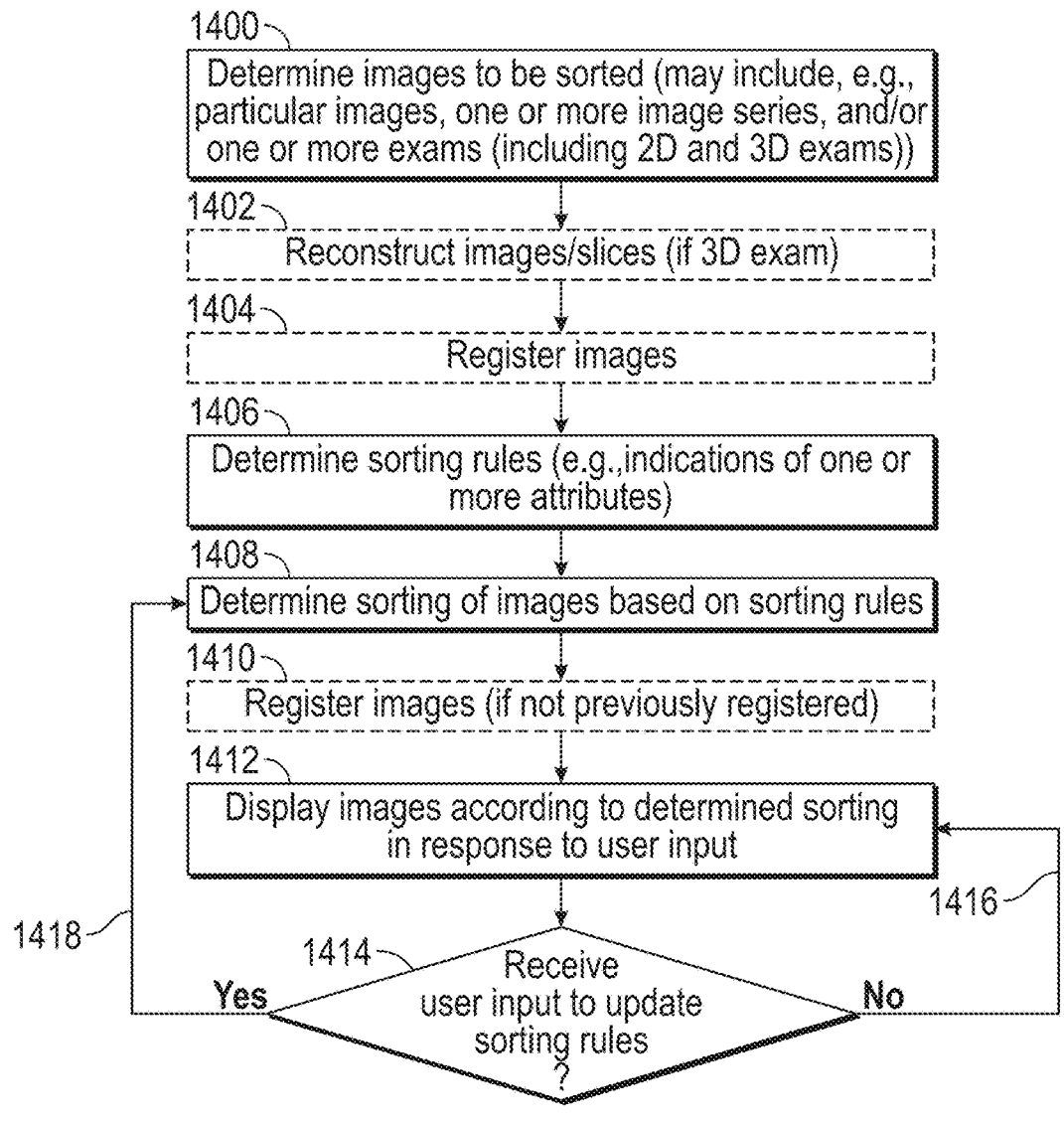
FIGS. 14A and 14B are flowcharts illustrating example operations of the system, according to embodiments of the present disclosure.
Figure 14B:
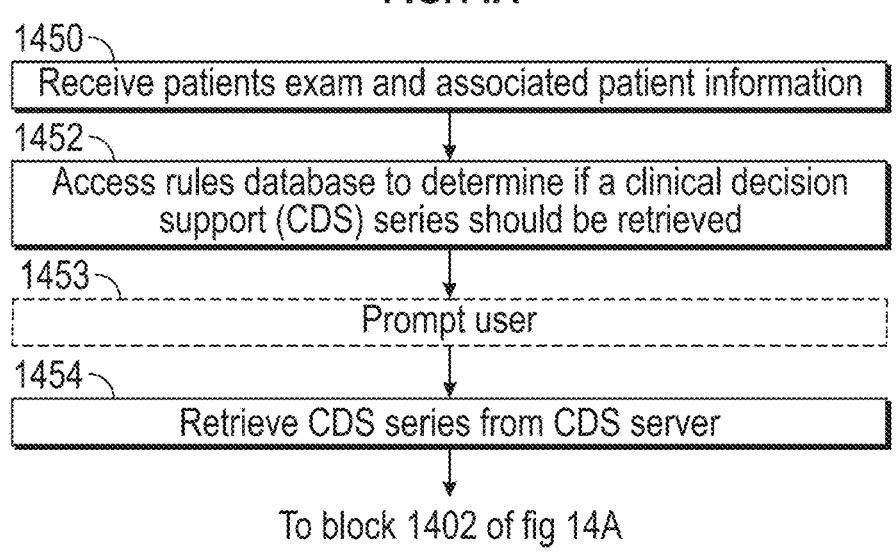
Figure 15A:
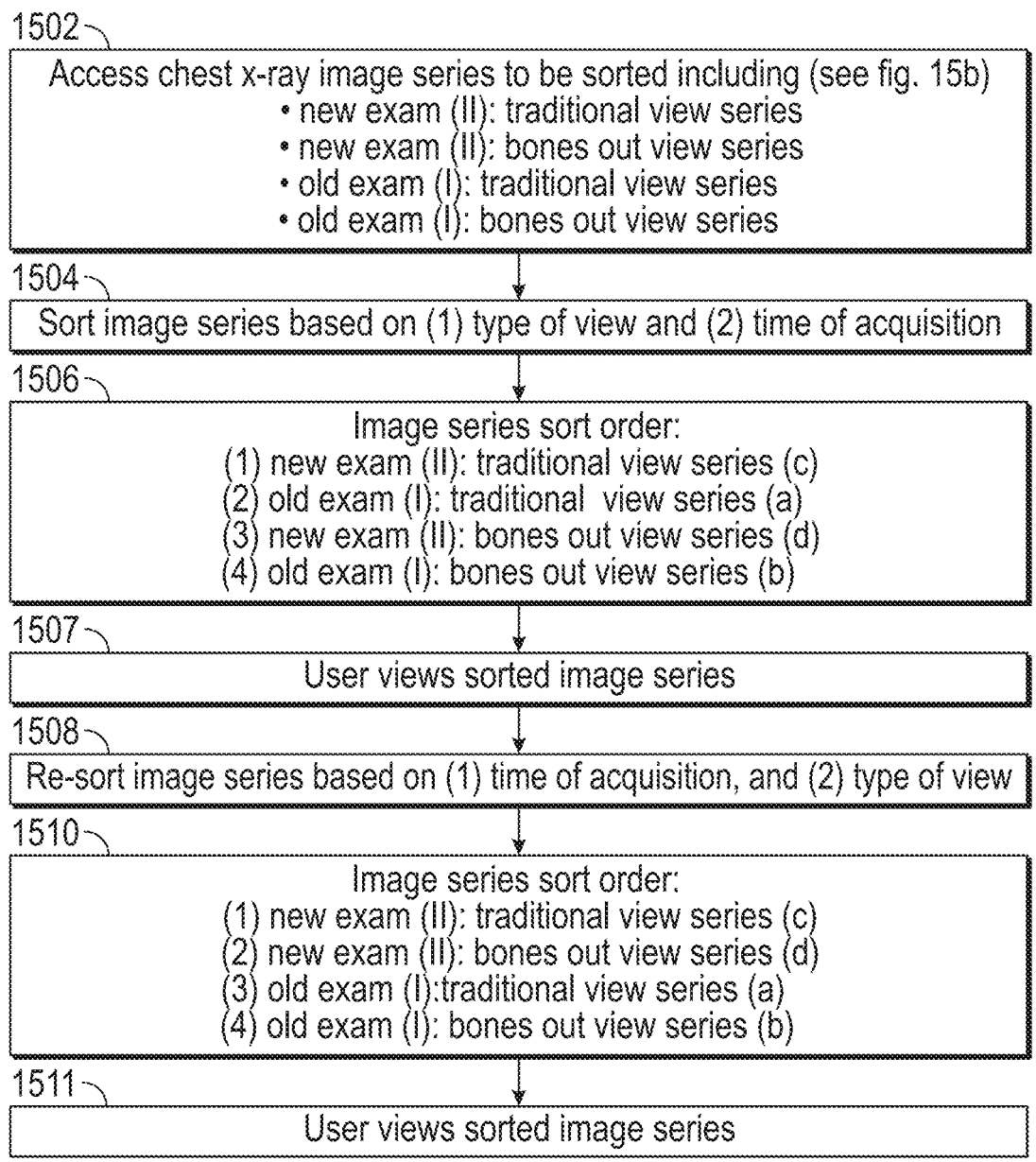
FIG. 15A is a flowchart illustrating another example operation of the system, according to an embodiment of the present disclosure.

FIGS. 14A, 14B, and 15A are flowcharts illustrating example operations of the system, according to embodiments of the present disclosure. Depending on the implementation, the system may perform methods having more and/or fewer blocks than are shown, and/or the blocks may occur in a different order and/or in parallel in order to accomplish certain methods and/or processes of the system.

In an embodiment, one or more blocks in the flowchart may be performed by, or implemented in, one or more computer modules and/or processors, as is described above and below with reference to FIG. 1.

Referring to FIG. 14A, a method of sorting and displaying images is illustrated, according to an embodiment of the disclosure. At block 1400, the system determines images to be sorted. For example, the system may determine individual images to be sorted, may determine one or more image series from which images are to be sorted, may determine one or more exams from which images are to be sorted, may determine one or more volumetric data sets from which images are to be reconstructed and/or rendered and sorted, and/or any combination of the above. Selection of images to be sorted may be provided by a user (e.g., a user manually selects two image series to be sorted), may be based on user preferences/rules that are automatically applied by the system (e.g., matching rules, as described above), and/or may be automatically selected based on system preferences. For example, the user may select a first image and/or image series to review, and the system may automatically determine a second image and/or image series to compare to the first image and/or image series. The system may then automatically sort the images of the first and second images/image series. Determination of images/image series/exams for comparison, as described elsewhere herein, may be based on rules (e.g., matching rules) selected based on an identity of, and/or characteristics associated with, the user. For example, the user may prefer to compare a particular type of image series with another particular type of image series. Such preference may vary based on a diagnosis of a patient and/or a reason for a medical exam from which the series are obtained. Additional examples of selection of images for comparison/sorting are described above in reference to FIG. 6 and below in reference to FIG. 16. Further examples of selection of images for comparison and to be sorted are described in the '167 application.

At block 1402, if images to be sorted are from a 3D exam (e.g., volumetric image data) then, if not already reconstructed and/or rendered, or if reconstruction and/or rendering is otherwise needed, the system may optionally automatically reconstruct and/or render the images. Reconstruction and/or rendering of images may be based on registration and/or matching techniques as described herein. For example, particular slices and slice thicknesses of the volumetric image data may be selected to match other images for comparison.

At block 1404, images to be sorted may optionally be registered/matched so as to reduce artifactual differences, as described herein. Such registration/matching may be based on one or more matching rules, as described above. Additional examples of registration and/or matching of images are described in the '167 application.

At block 1406, sorting rules for sorting of the images to be sorted are identified by the system. As described above, sorting rules may be selected based on an identity of, and/or characteristics associated with, the user. Alternatively, the user may select particular sorting rules. For example, in an embodiment the system may present one or more attributes to the user that may be used as a basis for sorting images (as described below). The user may then select one or more of the attributes, and a prioritization of the one or more attributes, such that the system may then apply sorting rules based on the selected one or more attributes. In some embodiments, sorting rules (e.g., attributes for sorting images) may be automatically selected based on a type of exam and/or series, and/or based on another characteristic of the exam and/or series. Examples of sorting rules are further described below.

At block 1408, the system determines a sorting of the images based on the determined sorting rules. For example, the system may process the images to be sorted, analyze attributes associated with the images, and, based on the attributes identified by the sorting rules, automatically sort the images. Examples of sorting of images are further described below.

At block 1410, the sorted images may optionally be registered/matched so as to reduce artifactual differences, such as by using one or more processes described herein. In some embodiments, registration/matching after sorting may be more effective than registration/matching before sorting (e.g., in optional block 1404) in that adjacent images may be better matched to each other. Such registration/matching after sorting may be performed in addition to registration/matching before sorting, or in place of the registration/matching before sorting. Such registration/matching may be based on one or more matching rules, as described above. Further, as mentioned above, in some embodiments, reconstructions and/or renderings of images from volumetric medical data may be performed based on, or simultaneously with, registration/matching and/or sorting. Additional examples of registration and/or matching of images are described in the '167 application.

At block 1412, images may be displayed by the system in the sorted order in response to user inputs, as described above. For example, the images may be displayed sequentially, in the sorted order, in a single image pane such that the user may quickly and efficiently determine differences between adjacent images.

At block 1414, the system may receive a user input to change the sorting rules. For example, the user may decide that a different sorting of the images may be more advantageous for identifying differences between two exams/series. Accordingly, the user may, on-the-fly, update the sorting rules. In response, the system automatically, as indicated by arrow 1418, determines a new sorting of the images based on the updated sorting rules, optionally registers/matches the sorted images (e.g., in the updated sorting order so adjacent images are registered with one another), and displays the images in the updated sorted order. In an embodiment, the sorting of the images may be updated in real-time or substantially real-time such that that user's review of the images is not interrupted. In an embodiment, an image displayed to the user prior to updating the sorting rules remains a same image displayed to the user after the images are re-sorted. Accordingly, the user may continue their review from the same image, but upon switching to adjacent images the images will be shown in the re-sorted order.

If no updates to the sorting order are received by the system, then the method continues with block 1412 wherein the sorted image series can be navigated by the user, as indicated by arrow 1416.

Figure 15C:
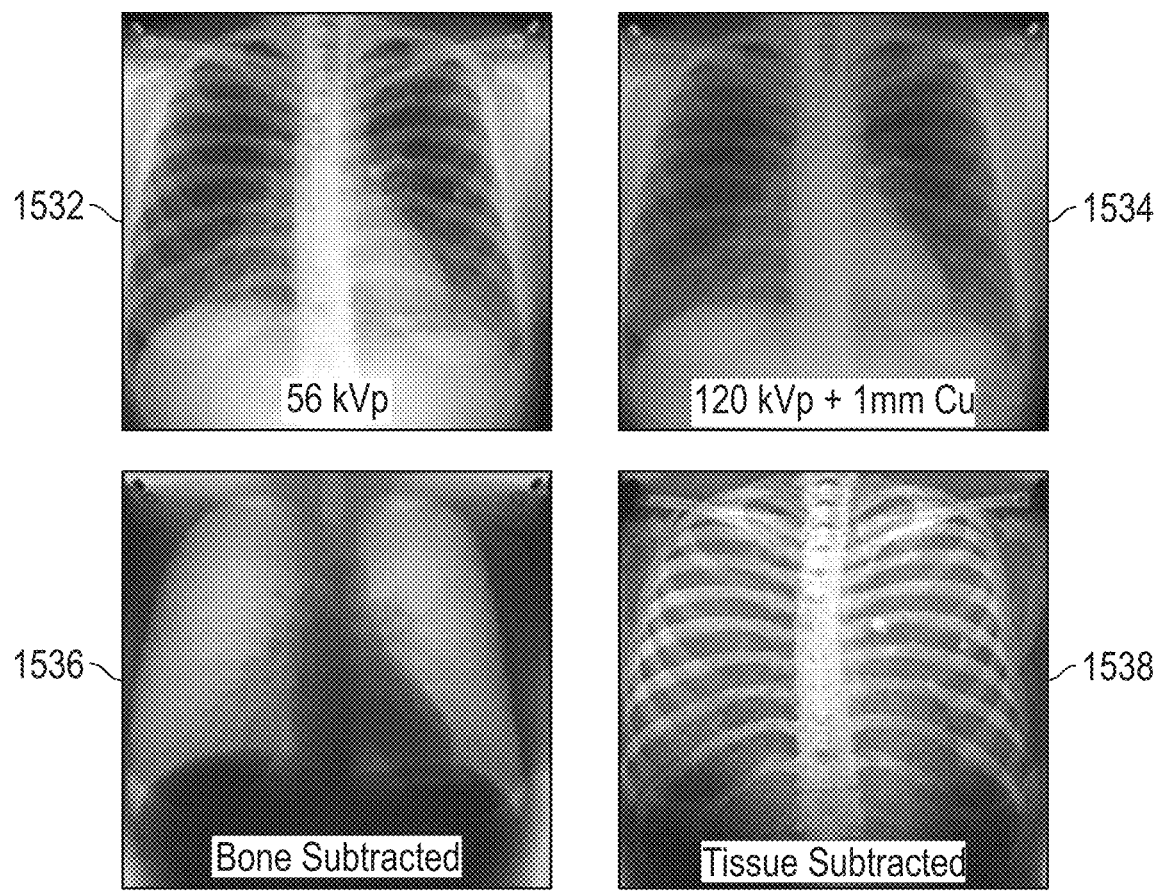
FIG. 15C is an illustration of four example images generated from dual-image radiography.

Referring to FIG. 15A, a flowchart illustrating a specific example of sorting images according to the methods described above is provided. In the example of FIG. 15A, a user is sorting and viewing images and image series produced via dual-image radiography. FIG. 15C is an illustration of four example x-ray images, 1532, 1534, 1536, and 1538, generated from dual-image radiography. Each of the four images may be part of a series of images of the types described below. In this particular example, image 1532 is a low energy x-ray image (low energy radiograph) of a chest of a patient, image 1534 is a high energy x-ray image (high energy radiograph) of the chest of the patient, image 1536 is a bones out view image (generated via processing of dual-energy radiography image data, also referred to as bone subtracted view) of the chest of the patient, and image 1538 is a tissue out view image (generated via processing of dual-energy radiography image data, also referred to as tissue subtracted view) of the chest of the patient. Such x-ray images may each be part of respective series of images of the same type as the respective types of the x-ray images, and each series may be part of a "dual-energy radiography" exam of the patient.

In order to evaluate the dual-energy radiography exam, and thereby determine a health and a diagnosis of the patient, the user may desire to compare images of the various types, and obtained at various times, to determine differences among the images. Accordingly, the images of one or more exams may be sorted and displayed by the system, based on various rules (including, sorting rules).

An example of such a sorting of two dual-energy radiography exams is now described. FIG. 15B is an illustration of example image series of two such dual-energy radiography exams, Exam I and Exam II. In the example of FIG. 15B, Exam I was obtained on 2012 Oct. 1, while Exam II was obtained on 2013 Jan. 20. Each exam includes two example image series. Exam 1 includes Series A, including images of a traditional view (e.g., low energy x-ray images), and Series B, including images of a bones out view. Exam 2 includes Series C, including images of a traditional view (e.g., low energy x-ray images), and Series D, including images of a bones out view. Each image series includes three images, consecutively numbered and associated with their respective image series, as indicated in FIG. 15B. In other examples one or more (or all) of the image series may include more images, fewer images, or a single image.

Referring now to FIG. 15A, the user may have recently received Exam II, and may have indicated to the system that the user would like to now evaluate the exam (or the system automatically initiates the method of FIG. 15A in response to a user rule indicating that the sorting process should be implement in response to receiving Exam II). Accordingly, at block 1502 (and as described above in reference to block 1400 of FIG. 14A), the system may determine, as described above, and based on one or more rules associated with the user, that images of Exam II should be compared to images of the previous Exam I, as the previous Exam I is of the same patient and for a same clinical indication. Further, the system may determine that certain image series of Exam I and Exam II correspond to traditional and bones out views and are to be compared. Alternatively, the user may specify particular exam/series types for comparison. The series to be compared are then accessed by the system.

In the example of FIG. 15A described below, series of images are sorted according to sorting rules. Such an example may be particularly useful when each series includes a single image. An example of sorting of individual images of the series (e.g., when each series includes more than one image) is described in references to FIGS. 5D and 5E below.

At block 1504 (and as described above in reference to blocks 1406 and 1408 of FIG. 14A), the series to be sorted are sorted according to some sorting rules. As described above, the sorting rules may be provided by the user, and/or may be determined based on an association with the user. The sorting rules indicate attributes of series based upon which series are to be sorted. In the example of FIG. 15A, the sorting rules indicate that the series are to be sorted based on two attributes: (1) a type of view of the series, and (2) a time of acquisition of the series. In the example, the attributes are prioritized such that the series are to be sorted, first, based on the type of view, and second, based on the time of acquisition.

At block 1506, the image series as sorted, based on the rules, are shown such that the traditional view series C and A are ordered before the bones out view series D and B. Further, the series are secondly sorted based on time of acquisition such that the most recent series are sorted first, resulting in a final sorting order of Series C, A, D, B. The series may then be displayed to the user in response to user inputs, as described above. Further, as described above, the series may optionally be registered and/or matched by the system. As also described above, in the example in which each series includes a single image, the user may then quickly flip through the images of the various types in the sorted order to quickly and efficiently identify differences among the different types of images, and the images obtained at different times.

Although not provided herein for ease of illustration, the sorting rules may further include an indication of sorting order associated with each attribute. Thus, for example, the sorting rules may indicate sorting based on time of acquisition, with the most recent appearing first (or, alternatively, the oldest appearing first). In another example, the sorting rules may indicate sorting based on a type of view, with the view ordered alphabetically and/or based on a particular order (e.g., traditional first, then bones out, then tissue out, etc.).

At block 1507, the user can navigate through the sorted image series, such as to view a single image of the sorted image series in a particular image pane on a display and update the single image displayed in that image pane to an adjacent image in the sorted image series based on commands from a user input device.

In some implementations, the user may want the images sorted based on different sorting rules (e.g., a different hierarchy of attributes). If such an alternative sorting order is indicated (e.g., by the user as images sorted based on first sorting rules are being view or based on user rules before viewing of the first sorted image series begins), at block 1508 (and as described above in reference to block 1414 of FIG. 14A), the series are re-sorted according to some updated sorting rules. As described above, the updated sorting rules may be provided by the user, and/or may be determined based on an input by the user. In the example of FIG. 15A, the re-sorting rules indicate that the series are to be sorted based on two attributes: (1) a time of acquisition of the series, and (2) a type of view of the series, in this priority.

Accordingly, at block 1510, the image series as re-sorted, based on the updated rules, are shown such that the series from most recent exam, series C and D are ordered before the series from the older exam, series A and B. Further, the series are secondarily sorted based on a type of view such that the traditional view appears before the bones out view, resulting in a final sorting order of Series C, D, A, B. The series may then be displayed to the user in response to user inputs, as described above. Further, as described above, the series may optionally be registered and/or matched by the system after the resorting.

At block 1511, the user can navigate through the re-sorted image series. As noted above, in some embodiments the user can switch between multiple sorting orders of images series via a particular input command.

FIGS. 15D and 15E illustrate two more examples of sorting of the images of the four example image series of FIG. 15B.

As shown, in FIG. 15D, the sorting rules 1552 indicate that the images are to be sorted based on three attributes: (1) an image number, (2) a type of view of the image, and (3) a time of acquisition of the image. In the example, the attributes are prioritized such that the images are to be sorted, first, based on the image number, second, based on the type of view, and third, based on the time of acquisition. Application of these sorting rules to the series of FIG. 5B results in the images being sorted as shown by the sorting results 1554.

As shown, in FIG. 15E, the sorting rules 1562 indicate that the images are to be sorted based on three attributes: (1) an image number, (2) a time of acquisition of the image, and (3) a type of view of the image. In the example, the attributes are prioritized such that the images are to be sorted, first, based on the image number, second, based on the time of acquisition, and third, based on the type of view. Application of these sorting rules to the series of FIG. 5B results in the images being sorted as shown by the sorting results 1564.

In the present examples the images are sorted based on an image number for illustrative and convenience purposes. However, rather than image number, more commonly images may be sorted based on an anatomical location or position, such that adjacent images in the sorting order show a same anatomical location or position. For convenience, image number is used in the present examples.

Referring now to FIG. 14B, a flowchart illustrating selection of clinical decision support (CDS) data for comparison is provided. As described above, selection of CDS data may be implemented in the CDS server 171. The blocks of FIG. 14B may, in some embodiments, replace block 1401 of FIG. 14A. For example, in some embodiments, rather than comparing and sorting two series of images or two exams, the system may determine a CDS series or CDS exam to compare to, and sort with, a patient exam. In other embodiments, the blocks of FIG. 14B may be in addition to block 1401 of FIG. 14A. For example, in some embodiments, CDS data may be sorted along with multiple sets of other patient data (e.g., series and/or exams).

As described above, sorting of images, and display of the sorted images, allows a user to more accurately and efficiently detect differences between images. In many of the examples described above, the user uses the system to compare images from the same patient to efficiently identify differences. For example, the system may be used to compare a series from one exam of the patient to another series from a second exam on the patient, which could be the same or a different modality, e.g., compare an MRI to an older MRI, compare an MRI to a PET obtained at substantially the same time, or compare a mammotomography series to a breast MRI series. In addition, a series from an exam might be compared to another series in the same exam, e.g., post-contrast images vs pre-contrast images. These examples may be considered a form of perceptual enhancement.

Using CDS data as described below, in some embodiments the user is able to view (e.g., as part of a sorted image series) images from the patient with images from another person, such as an age-matched normal, to determine if the patient's images are abnormal. These examples may be considered a form of clinical decision support, including a form of cognitive enhancement.

Further, using CDS data as described below, in some embodiments the user is able to view (e.g., as part of a sorted image series) images from the patient and reference images, such as an anatomical drawings, to aid him in determining features of an abnormality, such as anatomical location. These examples may be considered another form of clinical decision support.

As described below, CDS data may include any data that may be sorted with patient data to enable one or more of the advantages described above. For example, CDS data may include data from other patients (e.g., patients considered "normal"), wherein patients may be filtered to include only those other patients having characteristics similar to those of the patient; reference data (e.g., references images); and/or the like. For simplicity, the description below refers to a CDS series (e.g., a series of references image, or a series of images from another patient), however other types of CDS data may be utilized by the system in similar ways.

In an embodiment, using CDS data, a patient's images may be compared to another person's images (or a composite normal exam) for the purpose of determining if the patient's images are normal or abnormal. For example, a patient might undergo a PET scan of the brain in a work-up of dementia. The user's job may be to determine if the distribution of activity in the patient's brain is normal or abnormal. So, an axial PET series from the patient's brain PET exam might be compared (via sorting as described herein) with an axial series from a normal aged-matched control to allow the user to more easily and accurately detect regions of abnormal activity, where abnormal activity might be indicated by lower (or higher) standard uptake values (SUVs) at particular anatomical areas represented in the scan from the normal aged-matched control.

In another example, a brain MRI in, e.g., a 7 month old child, might be compared to a normal aged-matched control to allow the user to more easily detect abnormalities in brain maturation, such as evolving MRI signal intensity changes related to myelination.

Such CDS data (e.g., normal aged-matched control studies) may be stored in the CDS server 171. One or more rules of the user preferences and rules database 124 may automatically determine CDS series for sorting and display based on, for example, user preferences, exam type, and/or other clinical information associated with the exam. For example, when a PET scan is performed for the work-up of dementia, a relevant normal scan may be automatically retrieved and sorted.

In an embodiment, retrieval and sorting of comparison scans may be performed manually, on-demand (e.g., in response to a user input).

In another embodiment, a CDS series may include, for example, anatomical drawings labeling the anatomy and anatomically matching the patient's series. For example, when reading a CT of the liver or MRI of the brain, cross sectional images containing anatomical drawings may be automatically chosen and sorted to allow the user to more easily and accurately determine the anatomical locations of lesions in the patient's series, for example, the genu of the corpus callosum in the case of a brain MRI.

In one embodiment, a CDS series may be registered and/or matched, as described above. Thus, a CDS series may be selected to match an orientation of the patient's series and/or the CDS series may be reformatted, registered, and/or morphed to match the location and geometry of images in the patient's exam.

At block 1450, a patient exam and/or a series associated with a patient may be received. For example, the patient exam may be select by a user for review. Patient information may be received and/or accessed by the system such that one or more characteristics associated with the patient may be determined.

In an embodiment, patient information may be retrieved from data stored in, and/or attributes of, an exam, series, and/or image (as described above). In some embodiments, patient information may be obtained from other sources.

For example, in some embodiments the system may include a software module/process (e.g., a webservice) that is connected to an exam reading system of a user and that passively gathers information regarding exams, reports, images, etc., read by the user. For example, when a radiologist reads an exam, the exam may include structured data, or structured data may be derived from the report using natural language processing. Similarly, images of an exam may be processed using machine learning, and may read annotations on the images. In some instances, image annotations may adhere to a standard such as the automated image mark-up (AIM) standard via which information may be gathered. Such gathered information may comprise patient information useable by the system, such as to determine a more relevant CDS series (or series) for comparison with the patient exam.

At block 1452, one or more rules are accessed to determine, e.g., whether a CDS series is to be compared, and/or what type of CDS series is to be compared (as described above in reference to the various examples).

In an embodiment, as a user reads an exam, the user receives, from the system (at block 1453), a prompt to view CDS data related to the exam. For example, the prompt may say, "would you like to compare to the closest age and gender matched patient with the same imaging findings (or normal findings) for this type of exam?" Accordingly, the user may indicate that CDS data is to be obtained and compared to an exam. Thus, a sorted image series may include multiple image series of patient images (such as two image series of a same modality taken some time, e.g., weeks or months, apart in order to determine differences), as well as one or more CDS image series. Thus, in various embodiments (whether or not including CDS data)_more than two series/exams may be selected for comparison and sorted. For example, 3, 4, 5, or more, series/exams may be selected. As described above, in various embodiments, the multiple sorted series of images may be displayed in one or more image panes of the user interface.

In some embodiments, a ratio of images included in a sorted image series from the various image series and/or CDS series sorted varies. For example, in a sorted image series including two image series of a patient (e.g., two MRI series separated by two months) and one CDS series of a baseline MRI from a patient having certain characteristics similar to the patient (e.g., gender, age, etc.), the user may not want or need images from the CDS image series interleaved between each set of matched images in the two MRI image series. Thus, the CDS image series may be interspersed into the sorted series at a different ratio, perhaps including an image from the CDS image series in only every second, third, fourth, etc., set of matched images from the other image series. In another embodiment, the CDS image series may be included in the sorted image series, but only displayed in response to a predefined input from the user. For example, as the user scrolls through a sorted image series of the two patient MRI series noted above, the user could provide a particular input (e.g., pressing Control) while scrolling to indicate that a CDS image should be shown as the next image in the image series (e.g., so that unless the particular input is pressed by the user, the CDS images may not be displayed in the comparison pane). In other embodiments, CDS images may be interleaved and/or accessed with reference to images of the patient under review in various other matters.

At block 1454, the determined CDS series is retrieved from the CDS server 171. The method then proceeds with block 1402 of FIG. 14B, as described above.

Using the computing system 150, in an embodiment a user may manually sort matched medical images, e.g., order the selected/comparison medical images for progressive display. The system may also provide an interface to re-order images or image series, and may further enable reorienting images (flip, rotate) and/or changing other image characteristics in order to best match the display. In various embodiments, more than two series/exams may be selected for comparison and sorted. For example, 3, 4, 5, or more, series/exams may be selected. Further, multiple sorted series of images may be displayed in one or more image panes of the user interface.

VI. Example User Interfaces and Interactions for Automatic Selection and Display of Comparison Images FIG. 16 is a flowchart illustrating another example operation of the system, according to an embodiment of the present disclosure. Depending on the implementation, the system may perform methods having more and/or fewer blocks than are shown, and/or the blocks may occur in a different order and/or in parallel in order to accomplish certain methods and/or processes of the system. In an embodiment, one or more blocks in the flowchart may be performed by, or implemented in, one or more computer modules and/or processors, as is described above and below with reference to FIG. 1.

Figure 16:
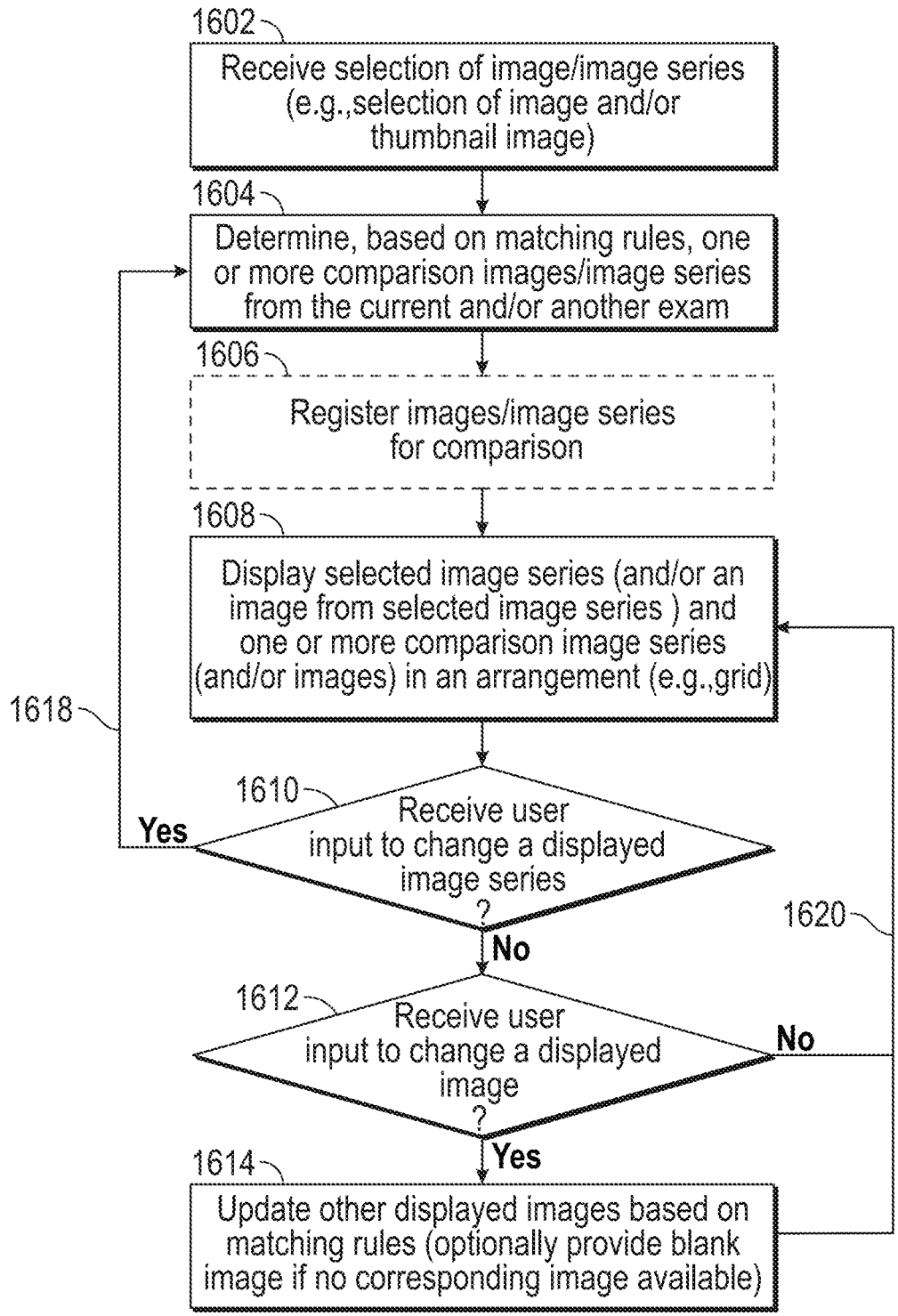
FIG. 16 is a flowchart illustrating another example operation of the system, according to an embodiment of the present disclosure.

FIG. 16 illustrates a method of selecting and displaying comparison images, series, and/or exams. Determination of images/image series/exams for comparison, as described elsewhere herein, may be based on rules (e.g., matching rules) selected based on an identity of, and/or characteristics associated with, the user. As mentioned above in reference to FIGS. 6 and 14A, examples of registration and/or matching of images in addition to those provided here (in reference to FIG. 16) are described in the '167 application. Additionally, any of the examples described here in reference to FIG. 16 may also be applied to the embodiments described in reference to FIGS. 6 and 14A above.

At block 1602, an image and/or series (and/or exam, in some embodiments) is selected by the user for viewing. Example user interfaces for such selection are described below in reference to FIGS. 17 and 18A-18C. Alternatively, the system may determine images for comparison (e.g., in comparison panes) based on one or more user preferences as described below in reference to FIG. 19E.

At block 1604, the system may, as mentioned above, automatically determine, based on one or more matching rules, one or more comparison images and/or image series (and/or exams). Such comparison images/series may be selected from a same exam as the selected image/series and/or another exam. For example, as described above, corresponding series from a previously obtained exam of the patient may be selected for comparison to a current series.

The matching rules may establish criteria for matching related images and/or image series. For example, matching rules may be established to select medical data based upon any of the following non-limiting criteria: modality (e.g., MRI, CT, X-ray, etc.); exam type (e.g., left knee X-ray, CT Chest, MRI Brain, etc.); archive status (e.g., has the exam been archived, archived and restored, not yet archived); assigned physician (e.g., has the exam been assigned to a particular physician for interpretation); exam age (e.g., how long ago was the exam done); patient age; any item in a DICOM header file (e.g., such as orientation, contrast use, thickness of slices, field of view, MRI tissue contrast weighting); time/day of acquisition; and/or any other attribute and/or image characteristic. In further examples, criteria may include information extracted through analysis of images (e.g., via one or more CAP), such as a view type of an image determined through automatic analysis of the image. With regard to some criteria, such as MRI tissue contrast weighting, the rules may analyze the MRI pulse sequence and the imaging parameters in order to determine the tissue contrast weighting and subcategorize images into weighting categories or weighting names.

The matching rules can be used to match medical images in the same and/or different medical series. For example, assume the medical images relate to three series each having 6 x-rays. The matching rules can be established such that like views among each of the different series are grouped together for subsequent viewing. The matching rules can be defined using simple or complex search expressions such as "AND" or "OR."

In another example, the matching rules may establish criteria for matching related images based on time and/or user preferences. Thus, as described below in reference to FIG. 19E, images of different types obtained at a same time may be selected for comparison (e.g., a Lateral chest view and a PA chest view).

At block 1606, the system may optionally register and/or match the selected images/series and/or the comparison images/series, as described above in reference to block 1404 and/or 1408 of FIG. 14A. While not shown in FIG. 16, in some embodiments the images/series may be registered and/or matched after block 1608 (wherein particular images are selected for display) such that adjacent images in the sorted image series match each other.

Figure 17:
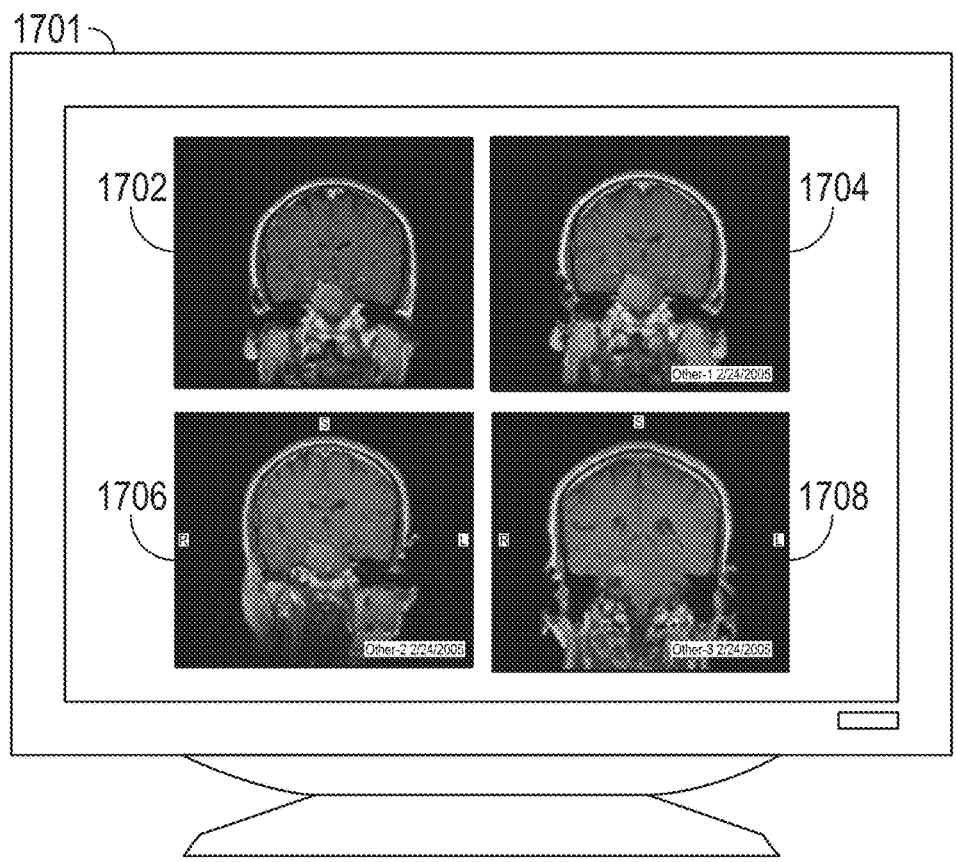
FIG. 17 illustrates an example user interface of the system, according to an embodiment of the present disclosure.

At block 1608, user selected and comparison images are displayed to the user simultaneously in multiple image panes of a user interface. FIG. 17 illustrates an example of such a user interface of the system, displayed on an electronic display 1701, according to an embodiment of the present disclosure. FIG. 17 includes many aspects similar to the user interface of FIG. 3 described above. The user interface of FIG. 17 includes four image panes: 1702, 1704, 1706, and 1708. In an example, the user may have selected the image shown in pane 1702, or alternatively a series from which the image shown in pane 1702 is obtained. In response, the system may have automatically determined, based on one or more matching rules, one or more other image series and/or images for comparison to the selected image/image series. The determined comparison images (and/or images from the determined comparison image series) may then be simultaneously displayed in the other panes 1704, 1706, and/or 1708. In the example of FIG. 17, the user is viewing four series, each of a same view type, each for a Brain MRI Exam of a patient obtained at different times. Thus, the user may compare corresponding images for the patient's brain from a current exam, from an exam obtained on Oct. 13, 2005 (pane 1704), from an exam obtained on Feb. 24, 2005 (pane 1706), and from an exam obtained on Oct. 8, 2003 (pane 1708).

In an embodiment, the user may select an image series and/or an image of the image series to view. In response the system may determine one or more comparison series. The one or more comparison series may be selected from a same or different exam of the selected image series. Further, when the user views an image from the selected series, the system may automatically determine matching images from the one or more comparison image series. For example, the system may determine images that match in regards to an anatomical area displayed. Thus, the user may be able to easily compare the displayed images. Further, as mentioned above, the images may be registered and/or matched with regards to one or more image characteristics.

In an embodiment, more or fewer image panes than are shown in FIG. 17 may be included in the user interface, and/or the image panes may be arranged differently. For example, the user interface may include 3, 5, 6, 7, 8 or more image panes. In an embodiment, the number of image panes in the user interface is based on a number of comparison image series determined by the system based on one or more matching rules.

In various embodiments, the user preferences and rules database 124 may include "display rules" that may indicate ways images and/or image series are to be displayed in user interfaces of the system. For example, an image or exam matching particular criteria in the display rules may be displayed with a certain pixel window level or width (similar to brightness and contrast), in color, based on a certain color map, opacity map, or other image characteristics. Display rules may be user-defined allowing the user to determine the timing, positioning, and size of displayed selected/comparison images. For example, a user can define that selected/comparison medical images are all displayed concurrently on a display. Also, for example, a user can define that the most recent of the selected/comparison medical images are displayed on the left hand portion of the display and the other selected/comparison medical images are displayed in sequence on the right hand side of the display, the sequence advancing in response to user prompting. In one embodiment, the display rules include directives (e.g., timing, positioning, and size). As an example, directives can include the following for identifying location information: TOP_DISPLAY, BOTTOM_DISPLAY, RIGHT_DISPLAY, LEFT_DISPLAY, CENTER_DISPLAY. Furthermore, if the number of comparison medical images is variable, the display rules can include instructions for identifying selected medical images based upon further rules, such as using the matching rules listed above. In addition, the display rules may or may not define how many images or image series are displayed per monitor, a display grid (e.g., 2×3, 5×4, etc.), or whether like images are displayed neighboring each other side by side horizontally or vertically. Furthermore, the display rules may also specify how different selected/comparison medical images from different series may be sorted together for successive display. Using the display rules, the user can provide display rules such that related medical images are readily comparable.

In an embodiment, display rules may be set to display pre- and post-contrast axial T1 weighted images from a brain MRI from the same exam in adjacent panes on a monitor. Display rules may also be set to display axial T2 weighted MRI images from a prior spine MRI adjacent to axial T2 weighted images from the current exam. Display rules may also be set to display a PA projection from a chest radiograph from a prior exam adjacent to the same projection from the current exam. As described below in reference to FIG. 19E, display rules may be set to display images of particular types in particular image panes (e.g., a PA chest view in one image pane and a Lateral chest view in another image pane) such that, for example, the user may view a particular preferred arrangement of images as images are flipped through in the user interface.

It is noted that the display rules may define user display preferences that are specific for particular types of medical images, e.g., the imaging modality, the body part, whether there is one exam, two, or more medical images being displayed. In one embodiment, one set of display rules can apply to one modality and another set of display rules can apply to another modality. In addition, the display rules may include specific triggers or warnings that occur if the user-defined display rules are not satisfied.

In various embodiments, display rules may be based on any image characteristic, as described above. Further, in some embodiments, display rules may be stored as image characteristics.

At block 1610, the system determines whether or not the user has provided a user input to change a displayed image series. For example, in reference to FIG. 17, the user may provide an input, such as a keyboard press and/or a gesture input, to change the image series displayed in pane 1702 to another image series. For example, the user may want to view a different image series of the exam of the patient, e.g., another view of the brain MRI exam. In response, as indicated by arrow 1618, the system may again, at block 1604, determine one or more comparison series. In some instances, newly determined comparison series may be selected from some exams as those of the previous comparison series, providing continuity for the user during review. In an embodiment, the user may change the image series of any of the displayed panes (e.g., including the comparison image series), and the image series of the other panes are automatically updated by the system.

At block 1612, the system determines whether or not the user has provided a user input to change a displayed image to another displayed image of a displayed image series. For example, in reference to FIG. 17, the user may provide an input, such as a keyboard press and/or a gesture input, to change the image displayed in pane 1702 to another image of the series. For example, the user may want to view a different slice of the particular brain MRI image series. In response, at block 1614, the system may automatically update the images displayed in the other panes to display different images, from each of the respective image series, that correspond to the image selected by the user. For example, the other images may be updated to display images of their respective image series corresponding to a same anatomical position as the selected image. In another example, each image series may comprise images of a same type but taken at different times (e.g., one series may include multiple PA chest views from multiple exams of a patient, while another series may include multiple Lateral chest view from multiple exams of a patient). In this example, the other image may be updated to display an image of its image series corresponding to a same exam/time of acquisition as the selected image (as described below in reference to FIG. 19E).

In an embodiment, the user may change the image of any of the displayed panes (e.g., including the comparison images), and the images of the other panes are automatically updated by the system.

In an embodiment, as indicated at block 1614, in some instances some image series may not include a corresponding image to be displayed. For example, one of the displayed image series may not include a particular image slice, a particular image that corresponds to an anatomical position, and/or a particular image of a certain view type. In these instances, as described below in reference to FIG. 19E, the system may advantageously insert placeholder images (e.g., a blank image, a grayscale image, etc.) and/or otherwise not display an image, while maintaining the sorted orders of each respective image series. Thus, the system may avoid displaying unrelated images to the user, and enable continuous, synchronized, and efficient review of multiple images series even where some image data may not be available.

As indicated by arrow 1620, if no input is received from the user the method continues at block 1608, displaying images and waiting for input from the user.

In an embodiment, a first user input (e.g., pressing an arrow or pageup/pagedown key, a side-to-side hand gesture movement, etc.) may change displayed image series, while another user input (e.g., a scroll of a mouse wheel, a forward-and-back hand gesture movement, an hand rotation gesture, etc.) may change displayed images. In an embodiment, user inputs may apply to a one of the panes that is currently selected by, e.g., a mouse cursor hovering over the pane, the user's hand being located near the pane, the pane being highlighted in the user interface, and/or the like. In an embodiment, the user interface may enable a user to "lock" certain panes such that the user's inputs only affect "unlocked" panes. Thus, the user may compare other images/image series to a "frozen" image in one or more of the panes. In another example, the user may similarly select a single pane to be "unlocked," causing all the other panes to be "locked."

Figure 18A:
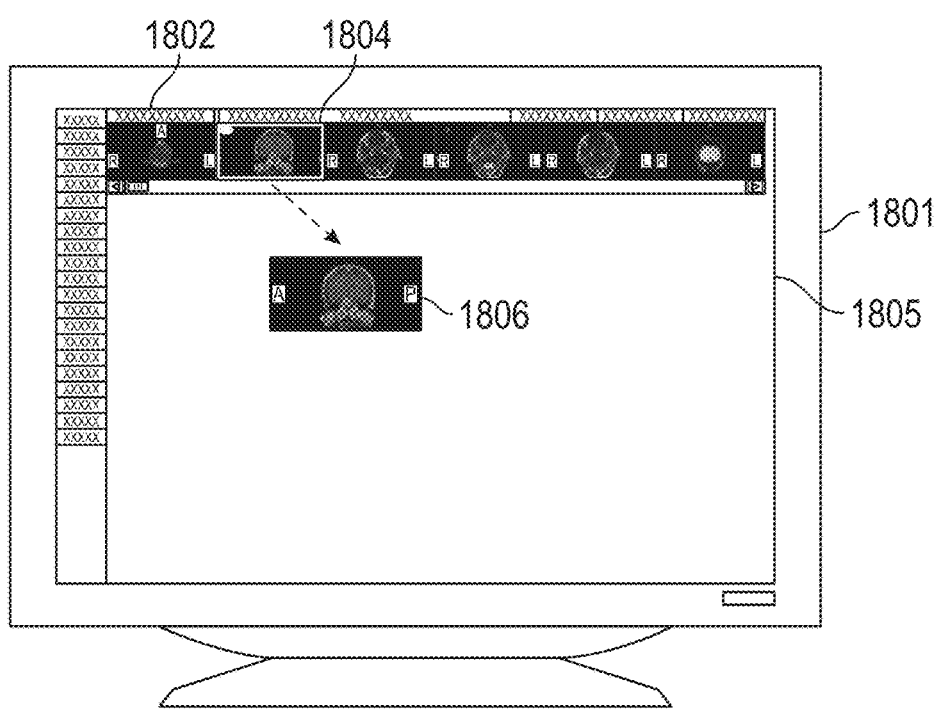
FIGS. 18A-18C illustrate example user interactions with the system via a user interface of the system, according to an embodiment of the present disclosure.
Figure 18B:
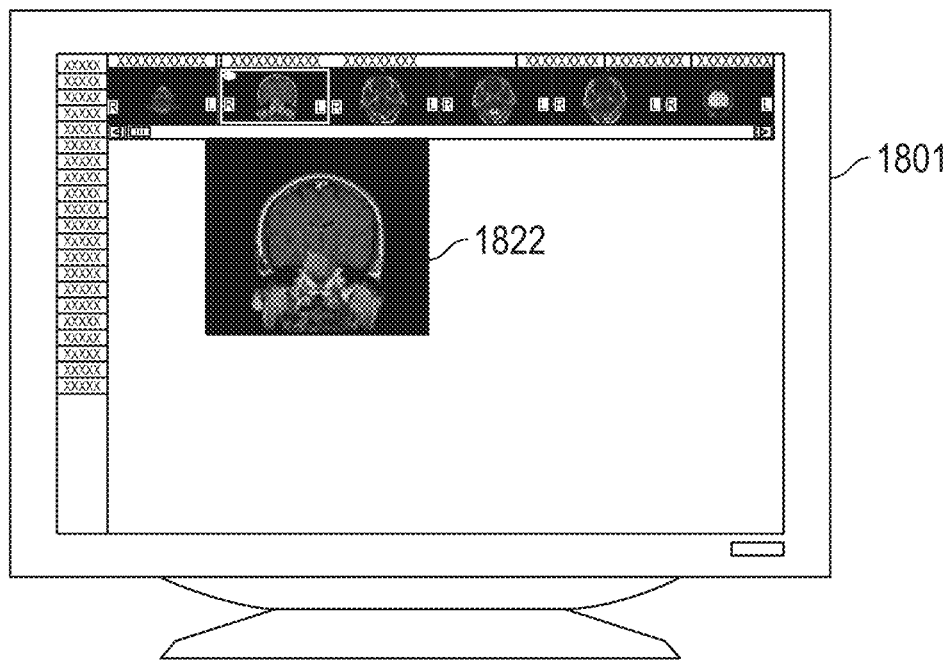
Figure 18C:
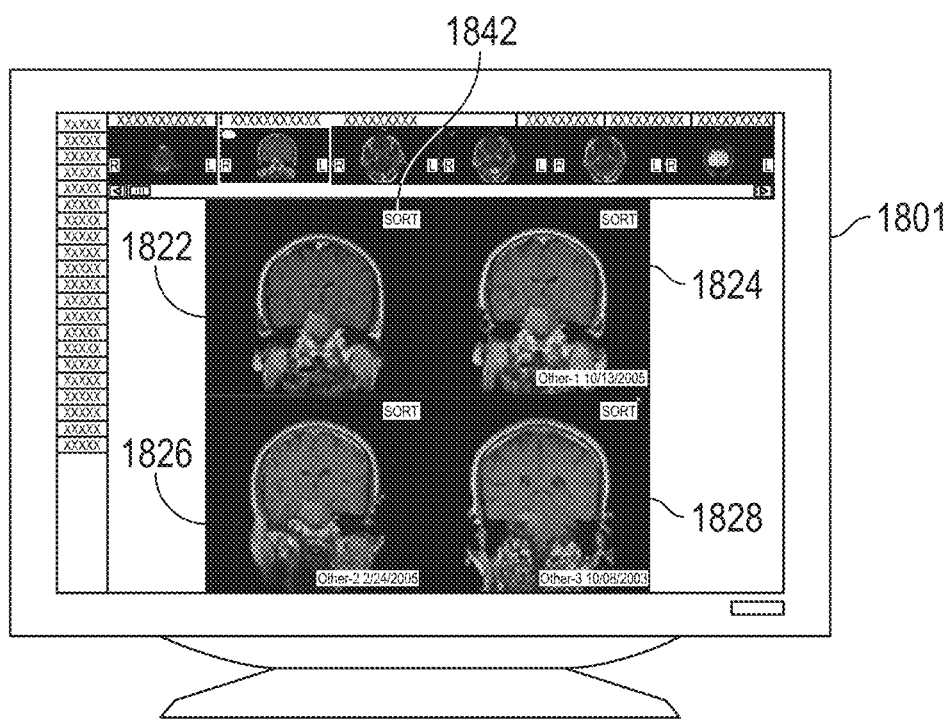

FIGS. 18A-18C illustrate example user interactions with the system via another example user interface of the system, according to an embodiment of the present disclosure. As shown, the user interface of FIG. 18A is displayed on an electronic display 1801 of the system. The user interface includes a row of thumbnail images 1802 along a top portion of the user interface. In various embodiments, the row of thumbnails may be in any location of the display. Each of the thumbnail images 1802 (e.g., thumbnail 1804) may be an image from a different image series. In some instances all the thumbnails are from a same exam, while in other instances each thumbnail is from a different exam. The user may scroll the row of thumbnails images 1802 to view representative images of various series of an exam (and/or multiple exams).

To view one of the images in more detail, the user may provide a user input to select a thumbnail image and/or drag a thumbnail image into a review portion 1805 of the user interface. Dragging of thumbnail image 1804 from the row to location 1806 is illustrated in FIG. 17 by the dashed arrow. As illustrated in FIG. 18B, once selected and/or dragged into the review portion 1805, a larger version 1822 of the image corresponding to the thumbnail may be displayed to the user. The user may then provide user input to move to different images of the image series of the displayed image, and/or provide user input to move to different image series, as described above.

In an embodiment, selecting and/or dragging the thumbnail image to the review portion 1805 causes the system to automatically determine one or more comparison images/series, as described above in reference to FIG. 16 (e.g., blocks 1604, 1606, and 1608) and 17. For example, as shown in FIG. 18C, other comparison series may be determined by the system, and relevant images from those series may be displayed in other images pane of the user interface (e.g., image panes 1824, 1826, and 1828). The user may interact with the user interface of FIG. 18C in various ways as described above in reference to FIG. 17.

In an embodiment, the user interface may include one or more "sort" buttons, such as sort button 1842. Selection of the sort button causes the system to sort, based on various rules and as described above in reference to FIGS. 6 and 14B (among others), either image series previously determined for comparison and displayed in the user interface, or other comparison image series. In an embodiment, upon selection of the "sort" button, a larger image pane may be added to the user interface that overlays the other image panes 1822, 1824, 1826, and 1828. Accordingly, the user may view the images in even greater detail, and quickly flip among the images to so as to have another method of detecting differences among the images/image series.

In an embodiment, a selected image, and/or an image on which the "sort" button is pressed, may be the first image displayed in the image pane displaying the sorted images.

In an embodiment, the selected thumbnail image will be enlarged in a preferred image pane, and/or an image pane to which it is dragged.

In an embodiment, different user inputs when selecting and/or dragging the thumbnail image may cause the selected image to either be displayed alone in greater detail, or compared to other image series (as in FIG. 18C). For example, dragging the thumbnail image by pressing a left mouse button may cause the image to be enlarged on its own, while dragging the thumbnail image by pressing a right mouse button may cause the comparison image series to be determined and displayed in the user interface.

VII. Auto-Registration With Shuffle Mode Presentation of Chest X-Rays

FIGS. 19A-19E illustrate implementations of auto-registration techniques that can be used in conjunction with image shuffling techniques in order to aid a user in comparing medical images (e.g., chest radiographs in these examples). A chest radiograph may be the most common medical imaging procedure in the world. Currently doctors and other healthcare workers compare chest radiographs side by side, such as to compare a previous chest radiograph with a current chest radiograph of a patient.

Figure 19A:
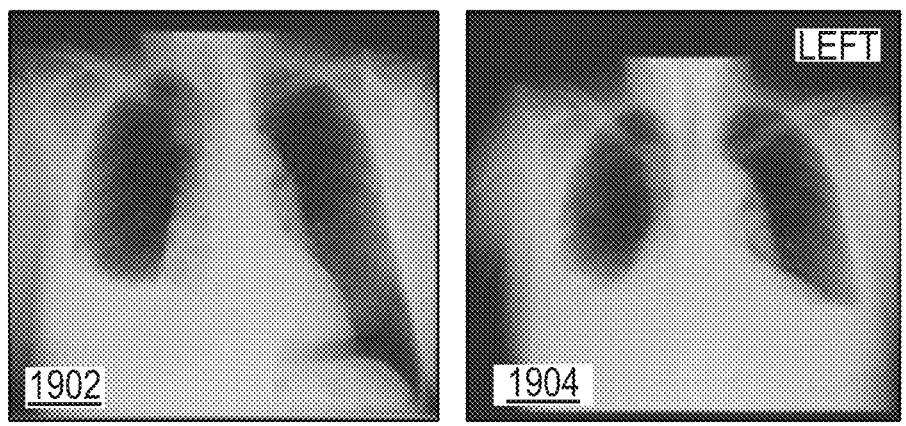
FIGS. 19A-19E illustrate implementations of auto-registration techniques that can be used in conjunction with image shuffling techniques in order to aid a user in comparing medical images, according to embodiments of the present disclosure.

FIG. 19A illustrates two postero-anterior (PA) chest radiographs 1902 and 1904 obtained on the same patient on different dates (e.g., several days, weeks, or months apart). In this example, the centering and field of view of the images 1902 and 1904 are not identical, perhaps due to one or more artifactual differences resulting from differences in the image acquisition environments. Thus, comparison of the images in a sorted series (such as by alternating display of images 1902 and 1904 at a same image pane on a display) would not be optimal in aiding the viewer in identifying small differences between the images overlap between common anatomical portions of the images are not aligned. As a result, without application of auto-registration of the images, they may only be compared side by side.

Figure 19B:
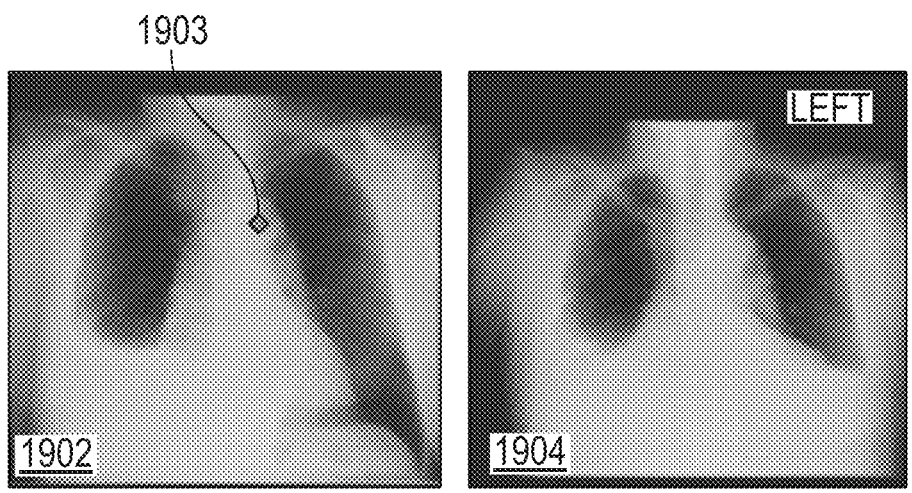

FIG. 19B illustrates the same two images 1902 and 1904, but with the aortic arch (sometimes called the aortic knob on a PA chest radiograph) marked on the left image by marker 1903. Depending on the embodiment, the marker 1903 could be manually provided by a user or, advantageously, identified by a computer algorithm that identifies this landmark structure automatically. Similarly, the aortic arch may be identified in the image 1904, either manually or by an automated process.

Figure 19C:
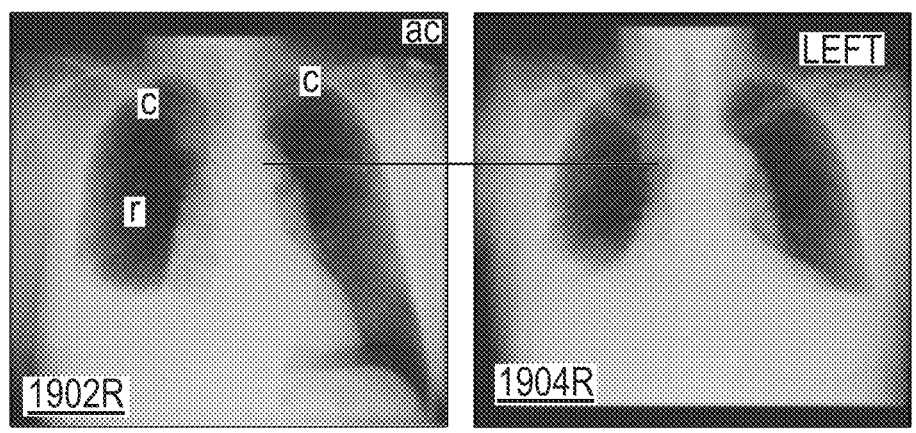

With this landmark structure identified in each of the two chest radiographs 1902 and 1904, an automated registration of the image may be performed, based on this common structure in each image. In FIG. 19C, one or both of the images have been automatically registered/matched (e.g., they have been matched with regards to one or more image characteristics, such as position, magnification level, window, etc.) in their respective image panes based on the identified aortic knob positions on the two side by side images. The images are denoted as images 1902R and 1904R to indicate that one or both of them have been modified from the original images 1902 and 1904, respectively. Depending on the embodiment, only one of the images may be modified (e.g., the comparison images may be 1902 and 1904R, or may be 1902R and 1904).

In the example of FIG. 19C, a horizontal line illustrates that the aortic knobs in images 1902R and 1904R are at a same level (whereas they are at different levels in images 1902 and 1904). As noted above, other registration modifications may be made to one or more of the images 1902 or 1904, such as using information in the DICOM meta-file to automatically adjust the images to a same scale (and/or any other image characteristic).

However, in other embodiments, the computer system may make other adjustments to alter the scales in order to best match the actual anatomy understanding that different radiographic images can show various levels of geometric magnification based on the projection (AP vs PA) or distance of the patient from the detector and x-ray tube.

In the example of FIGS. 19A-19D, the aortic knob is chosen as the landmark for matching chest radiographs because it is more consistently identifiable and relatively central in location than other possible landmarks. Furthermore, the aortic knob may be more consistent in size whether the image is taken AP or PA. In some embodiments, other landmarks, and/or multiple landmarks, could be used for registration purposes, such as in addition to the aortic knob or instead of the aortic knob. For example, clavicles (c), AC joints (ac) or ribs (r), which are labeled in image 1902R of FIG. 19C, may be useful in adjusting for position or obliquity differences (and/or other artifactual differences, such as rotational, translational, or scaling differences) between images.

With images 1902R and 1904R registered in this manner (e.g., via an automated process of identifying the aortic knob in each of the images 1902 and 1904 and adjusting the images to be registered in view of those identified positions), the images can advantageously be presented in a sorted series for comparison, such as by alternative display of the images in a particular comparison pane on a display in order to allow the user to more easily identify actual differences in the images.

Figure 19D:
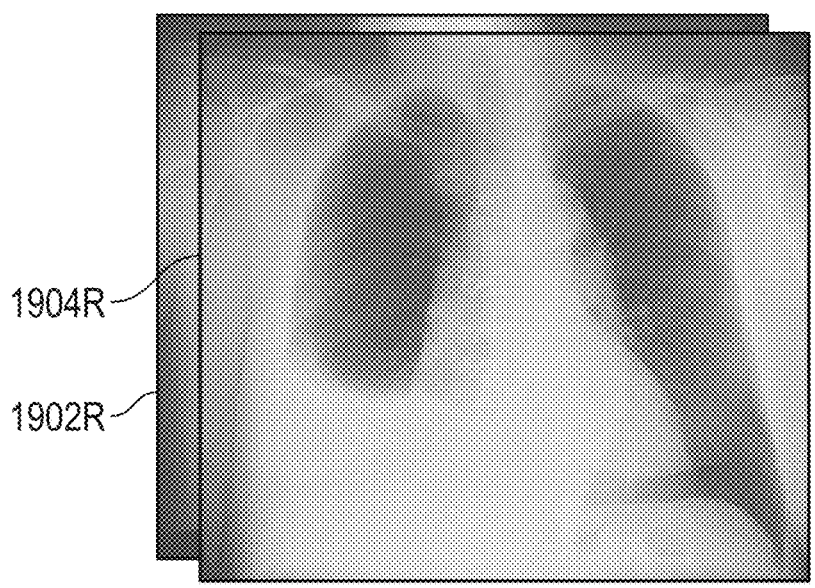

In the example of FIG. 19D, image 1904R is overlaid on image 1902R to illustrate relative positioning of the images when aligned based on the aortic knob landmark (e.g., so that the aortic knob in each of the images 1902R in 1904R is at a same location on the display). Thus, the images can be compared by paging through a stack of images chronologically, or otherwise, ordered instead of comparing them side-by-side.

Figure 19E:
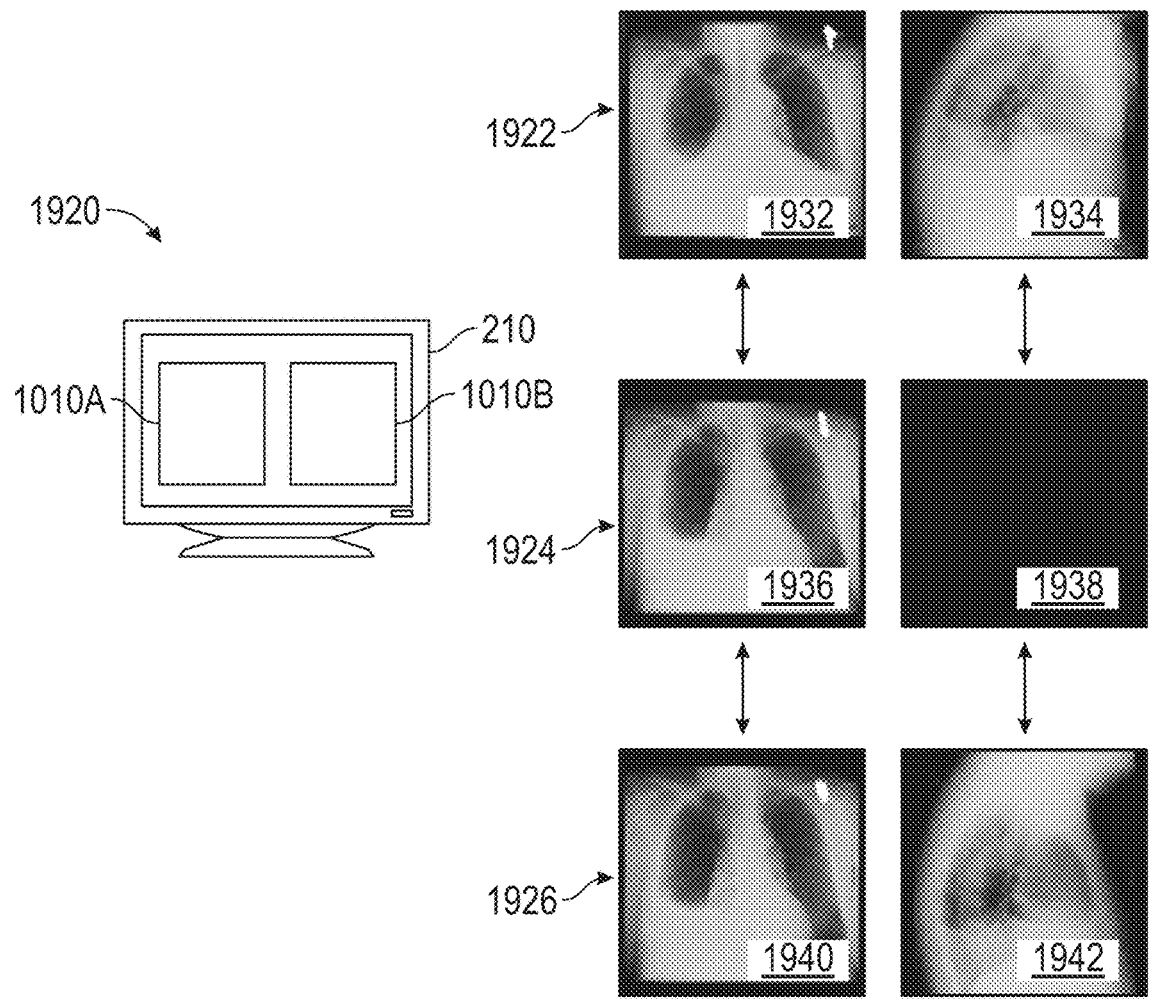

FIG. 19E illustrates an example of comparing multiple images (in this example, chest radiographs) simultaneously. As described above in reference to, for example, FIGS. 10-12, the system may display two or more comparison panes (e.g., 1010A and 1010B) simultaneously on a display device (e.g., display device 210). Further, as described above in reference to, for example, FIG. 16, comparison images may be determined by the system in various ways. Thus, multiple interleaved or otherwise sorted image series may be concurrently displayed in separate comparison panes.

These comparison panes (which may include two, three, four, or more panes) may be organized and/or positioned in various arrangements. For example, the comparison panes may be positioned to the left and right of one another, above and below one another, in a grid, and/or according to any other arrangement. The number and positioning of the comparison panes may be determined based on one or more user preferences, and/or may be predefined by the system. Such comparison pane determinations may be based on one or more display rules as described above in reference to, for example, FIG. 16.

Further, the system may be configured to display particular images, image series, and/or types of images, etc. in each comparison pane. Thus, for example, any image characteristic/attribute may be associated with the comparison panes. These associations between panes and image characteristics/attributes may be determined based on one or more user preferences, and/or may be predefined by the system. Thus, the system may advantageously be configured to display images, which may be flipped through by a user, in particular arrangements (e.g., hanging protocols). For example, one user may prefer to see left-facing lateral view images in one pane, while another user may prefer to see right-facing lateral view images in that pane.

For example, as indicated by image set 1922, a user may view two chest radiograph images 1932 and 1934 side by side (e.g., in comparison panes 1010A and 1010B). Images of image set 1922 may be related, e.g., they may be part of a same exam (e.g., obtained on the same day), and/or otherwise related. The images may also each be of particular types (and/or have a particular one or more image characteristics) and may be associated with respective series of images. For example, image 1932 may be a PA view of a chest (and part of a sorted image series of PA views including images 1936 and 1940) while image 1934 may be a Lateral view of a chest (and part of a sorted image series of Lateral views including image 1942). The image series associated with each image may be comprised of sorted image series that may be sorted according to any method described herein. For example, each image series may comprise multiple images of a same type that were obtained at different times (e.g., as part of different exams), but associated with a same patient. Further, the images of each image series may be registered/matched (e.g., scale, skew, contrast, etc. may be automatically adjusted in one or both images so they match and are more comparable) to enable efficient comparison as the user moves/flips from one image to the next.

As mentioned above, as the user provides input, the system may display (e.g., flip through) images of the multiple image series in a sorted order. Thus, for example, the system may replace images 1932 and 1934 (in their respective comparison panes) with images 1936 and 1938 (in their respective comparison panes, as indicated by 1924). In response to a further input, the system may replace images 1936 and 1938 (in their respective comparison panes) with images 1940 and 1942 (in their respective comparison panes, as indicated by 1926).

As mentioned above, each set of images (1922, 1924, and 1926) may be related (e.g., part of a same exam), however in some instances a particular exam may not include an image or image series of the type associated with a comparison pane. For example, sometimes a patient may have PA and Lateral chest exam one day, a single view AP chest exam the next day, and an AP and Lateral chest exam the day after that. To compare the images associated with these exams by flipping through the images in the comparison panes, the system may (as described above in reference to FIG. 16) advantageously insert placeholder images (e.g., a blank image such as image 1938, a grayscale image, etc.) and/or otherwise not display an image, while maintaining the sorted orders of each respective image series. For example, as the user flips though the two related image series of FIG. 19E, because there is no Lateral chest view image related to PA chest view image 1936, a blank 1938 may be displayed in comparison pane 1010B. Thus, the system may avoid displaying unrelated images to the user, and enable continuous, synchronized, and efficient review of multiple images series even where some image data may not be available.

In various implementations, as described above, images/image series may be determined to be related (e.g., matched) based on various image characteristics and/or other information. For example, DICOM header information may be analyzed to determine related series of images. In an embodiment, the system may perform one or more CAP on images/images series to determine relationships. For example, in the context of chest radiographs, images may be analyzed by the system to determine dates and/or other information contained within the images that may be used for matching images/image series.

Further, in some implementations the system may perform one or more CAP to identify image characteristics (e.g., as may be useful when no DICOM header information is present). For example, in the context of chest radiography, the system may analyze an image to determine that the image is a PA chest view, AP chest view, Lateral chest view, and/or the like.

Thus, the system may automatically determine an image series with which an image should be associated, an ordering of images within the image series, and a comparison pane where images of the images series are to be displayed.

In some implementations, the system may enable the user to manually register images by, for example, overlaying the images and/or placing the images side-by-side and providing tools for efficiently adjusting various image characteristics of one or both images.

As mentioned above, the inventors have found that users using the system to flip through medical images (e.g., to analyze the images and perform diagnoses based on the images) are faster (e.g., 15% faster or more) and more accurate than users using traditional methods of comparing images.

As with other examples herein, shuffling of two images (or two image series or exams) are discussed for purposes of illustration of the various automated processing techniques, but the same processes could be used for more images, so that a user could easily page or scroll through a sorted image series including chest radiographs (or any other image) taken over time to more efficiently and accurately detected changes. For example, registration of chest radiographs of a child taken every 3 months from birth to age 6 may require significant adjustments in various image characteristics in order to register the images such that a "timeline" of changes over those years (e.g., including 20-40 images—none of which have precise alignment prior to auto-registration) can be viewed in a slideshow (or "cine" mode, whether automatically advancing through images at a predefined interval, such as ¼, ½ or 1 second, or manually in response to user input) and can provide to a user visual comparisons that may be useful for diagnosis or treatment of the patient. Without such auto-registration techniques (e.g., based on alignment of the aortic knob that may be automatically detected in each of a plurality of images), such a timeline of multiple images would be difficult to derive useful data from, as positions of anatomical structures (e.g., the or aortic knob) would move from one position to another (as well as having other image characteristics different from one image to another) as each subsequent image is displayed.

In an embodiment, the system generates a chest radiograph sorted series in substantially real-time so that differences in chest radiographs can be identified with relative ease and time constraints on the viewing user. Without such an automated registration and sorting algorithm, a user could not practically make a comparison of chest radiographs in a similarly beneficial manner, especially where the number of chest radiographs is larger than two.

In one example implementation that makes use of certain features discussed herein, the system provides a specific hanging protocol for a chest radiograph combined with shuffling, combined with image analytics to select the proper views, combined with image analytics to result in display with matching orientation, registration, and scale.

VIII. Montage Image Sorting

Figure 20:
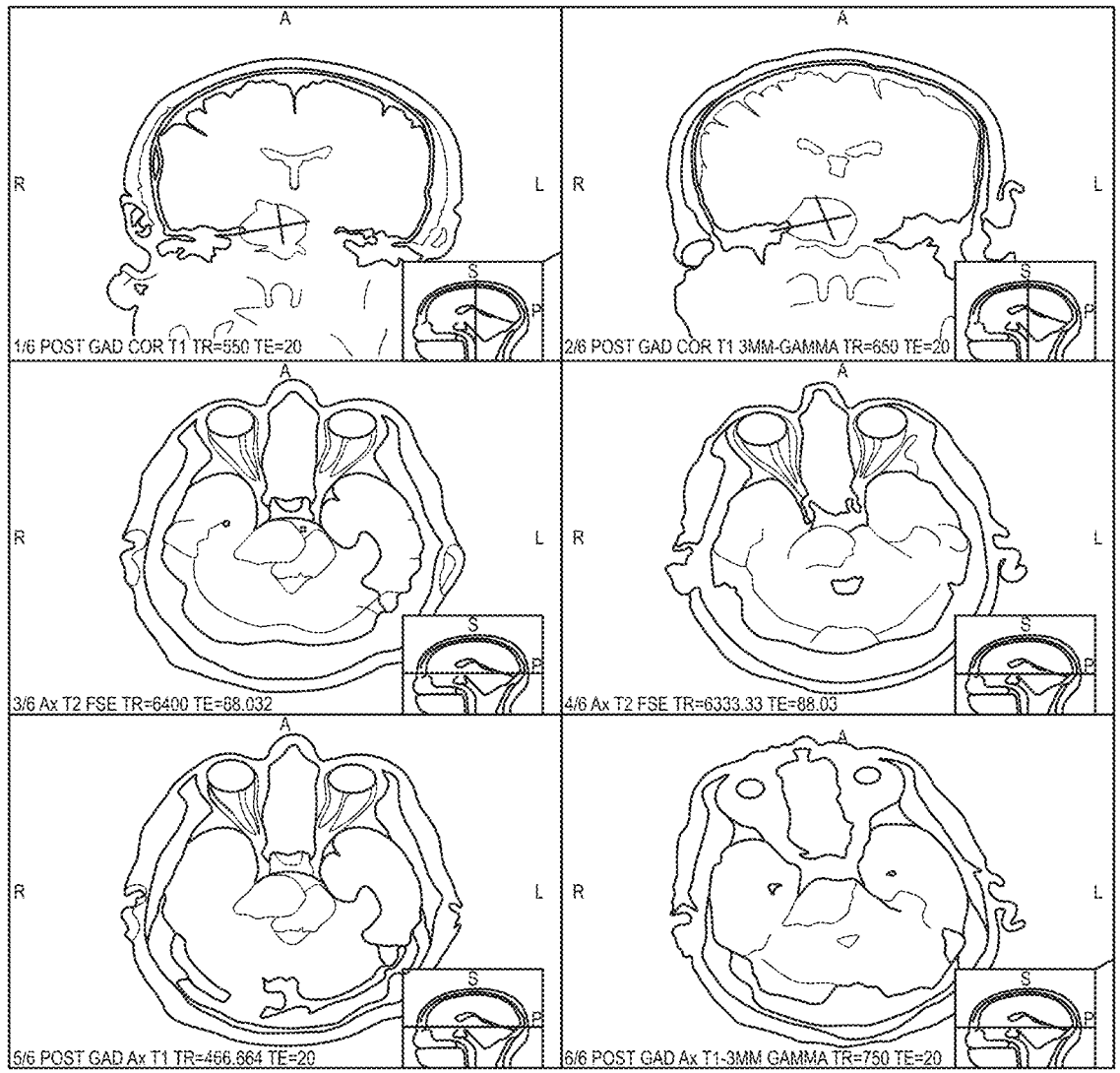
FIG. 20 illustrates an example montage that may be displayed on a computing device of a user, according to an embodiment of the present disclosure.
Figure 21:
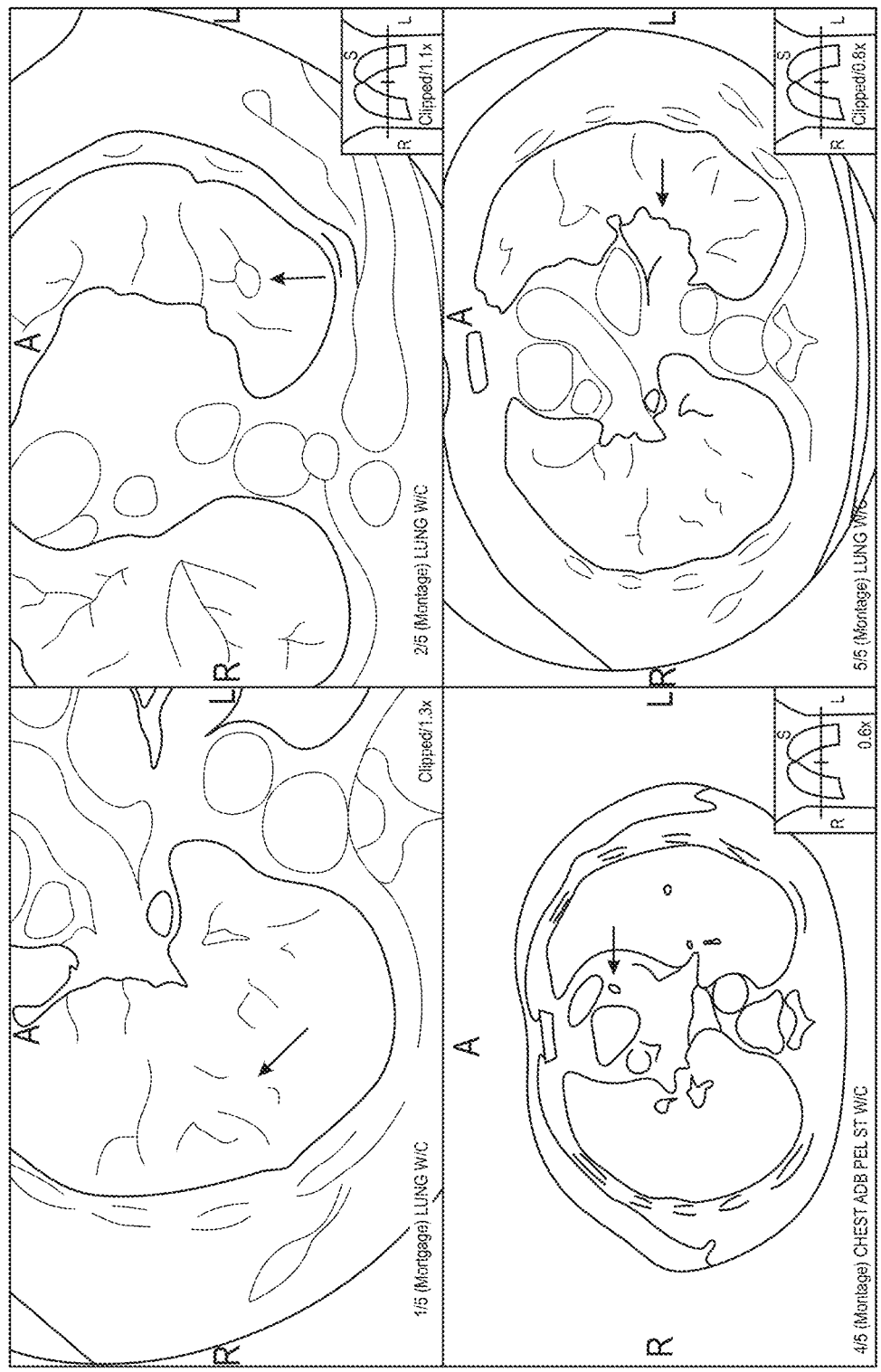
FIG. 21 illustrates another example montage that may be displayed on a computing device of a user, according to an embodiment of the present disclosure.

FIG. 20 illustrates an example montage that may be displayed on a computing device of a user. In the illustration of FIG. 20, the images of the montage are those selected by the user as key images, such as at the time of review of an MRI of the Brain. In one embodiment, the user composes the montage by selecting one or more key images from one or more image series, and by adjusting various image characteristics of the images (e.g., view settings of the images, such as window/level settings, centering, cropping, magnification, annotations, insets, etc.). The same image might be selected more than once, but shown on the montage with different image characteristics. FIG. 21 illustrates another example montage with a different number of images, including images that are formatted differently and include annotations (e.g., arrows pointing to areas of specific interest).

In some implementations, montages are saved as separate files, such as separate image files that are essentially a screenshot of a montage (e.g., a snapshot of the montages of FIG. 20 or 21) or two or more images stitched together into a single image. Thus, the montage that is configured by the user may be recalled at a later time. In one embodiment, the montage image file may be notated as a key image, such as according to the DICOM specification. The montage might include images from multiple exams, or might include reference images such as illustrations or medical images exemplifying pathological or normal conditions. A montage may be added to an exam or series such that it may be sorted with other images, for example.

In some implementations, a montage having one or more images can be stored in one or multiple ways, including (1) storage of the complete composite montage image and/or (2) storage of sufficient information regarding each image so that the entire montage can be recreated upon future display or the individually stored images can be displayed, depending on the user's preferences, depending on the display environment (such as aspect ratio of the display window, monitor resolution, a combination of user preferences and display environment, or other factors.) For example, information regarding the arrangement of images in the montage, as well as information regarding display settings of respective images (e.g., magnification, brightness, centering, cropping, filters, annotations, insets, etc.) may be stored. These montage characteristics may then be recalled at a future time and used to re-build the montage. In this implementation, storage of an image of the entire montage may not be necessary, while in other embodiments the montage image (e.g., a snapshot of the montage) may be stored and used in certain circumstances, such as when the montage is to be displayed on a display having essentially the same resolution and aspect ratio as the display on which the montage was originally created. As used herein, the arrangement information included in montage characteristics may include a number of rows and columns of medical images in the montage, indications of specific locations of each medical image in the montage, indications of an order that medical images of the montage are displayed, and/or any other information that may be usable to construct a montage on the same or another computing device based on the layout of the montage images.

Additional examples of montages and uses of montages are described in U.S. patent application Ser. No. 13/572,397, filed Aug. 10, 2012, and titled "DYNAMIC MONTAGE RECONSTRUCTION," (the "397 application"), the disclosure of which is hereby incorporated by reference in its entirety and for all purposes, as if set forth fully herein.

As mentioned above, and according to any of the image viewing techniques described above, while viewing images (e.g., of one or more exams, series, etc., which may or may not be sorted), the user may designate certain images as key images. For example, the user may click a mouse button, keyboard shortcut, or by other input means indicate that an image is a key image. In some implementations, key images may be placed in a montage. For example, the user may indicate that certain images are to be placed in a montage by designation of those images as key images.

As described above and in the '397 application, images of a montage may be stored as separate files and information necessary to reconstruct the montage may be stored, and/or automatically combined into a single montage image. At the time a user requests to view a montage, the system may generate the montage, if necessary. Further, the system and/or user may determine if the montage is to be presented/ assembled as originally stored, broken up into individual image components, and/or otherwise rearranged.

In some implementations, when an image is designated as a key image, an annotation is added to an image, and/or a user otherwise indicates that they want to add the image to a montage, the system may automatically perform additional actions with respect to that image. The actions performed, and the user input that causes the actions to be performed, may be based on one or more user preferences.

In one implementation, in response to such a user input (e.g., marking an image as a key image), the system automatically adds the indicated image to a series/exam in an appropriate location in the series/exam (e.g., in a sorted location). For example, suppose a series/exam consists of 8 images, some of which are multi-frame images (MF), and some of which are single frame images (SF). In this example, the series/exam may include the following images:

Image 1—MF
Image 2—MF
Image 3—SF
Image 4—MF
Image 5—SF
Image 6—SF In this example, the user may indicate certain sub-images of one or more of the multi-frame images, and/or one or more single frame images, for further actions (e.g., may indicate as key images, may indicate as images to add to a montage, may add annotations, and/or the like). For example, the user may indicate a few frames (e.g., sub-images) of Image 1 (e.g., frames 32 and 38), and also Image 3. Thus, the system may, based on the user preferences add these indicated images to a montage and/or save the indicated images to the series/exam. Accordingly, in the example, the series/exam becomes:

Image 1—MF
Image 1.32—SF
Image 1.34—SF
Image 2—MF
Image 3—SF
Image 3.1—SF
Image 4—MF
Image 5—SF
Image 6—SF
Montage As shown, the images are automatically added to the series/exam and are further automatically sorted such that they are located in appropriate locations in the series/exam. Images of a series/exam may be sorted based on one or more sorting rules and/or user preferences, as described herein. Advantageously, adding the images to the series/exam in the sorted locations may enable the user to easily display the series/exam's initial images and the added images in sequence (e.g., via any of the methods described above), and also be able to see the montage in a separate sequence.

In various implementations, the images that are added to the series/exam may be sorted based on various sorting rules, image characteristics, user preferences, and/or any other criteria, as described above in reference to the various embodiments of the disclosure. For example, the images may be sorted based on image numbers such that added images are added near (e.g., immediately after) an existing image from which the added image is derived.

In an implementation, the user may indicate where in a series/exam an image is to be added. Additionally, as mentioned above, the indicated images may be added based on one or more user preferences and/or image characteristics.

Figure 22:
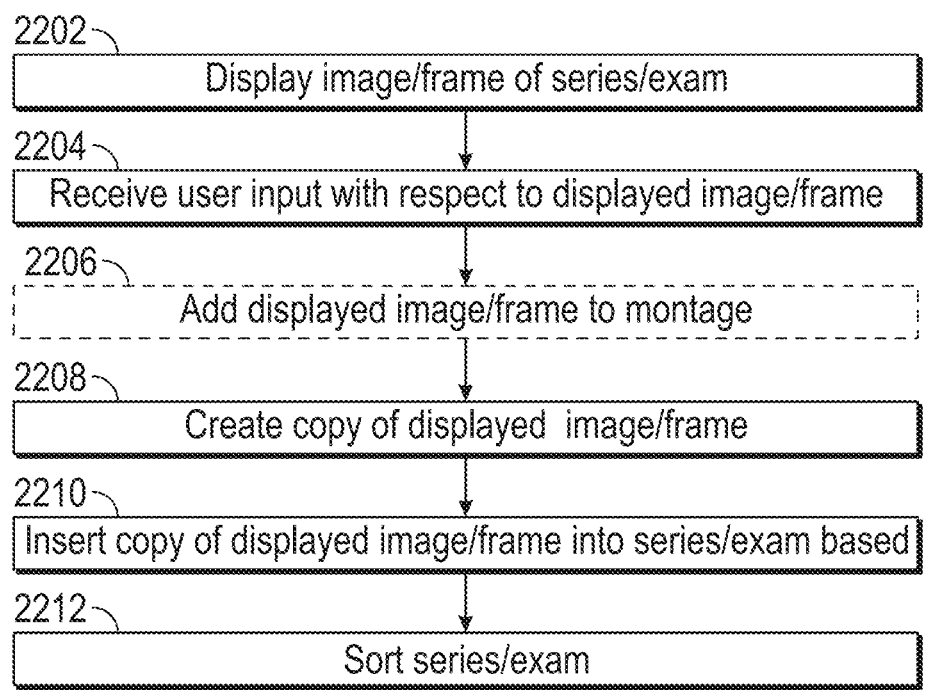
FIG. 22 is a flowchart illustrating another example operation of the system, according to an embodiment of the present disclosure.

FIG. 22 is a flowchart illustrating an example operation of the system, according to an embodiment of the present disclosure. Depending on the implementation, the system may perform methods having more and/or fewer blocks than are shown, and/or the blocks may occur in a different order and/or in parallel in order to accomplish certain methods and/or processes of the system. In an embodiment, one or more blocks in the flowchart may be performed by, or implemented in, one or more computer modules and/or processors, as is described above and below with reference to FIG. 1.

FIG. 22 illustrated a method of generating montages and/or inserting particular images indicated by a user into a series or exam. At block 2202, the system displays an image (or frame of an image, e.g., a sub-image) of a series or exam according to any of the methods described herein.

At block 2204, the system receives a user input with respect to the displayed image/frame. For example, the user may indicate an image/frame is a key image/frame, may annotate the image/frame, and/or may otherwise indicate the image/frame is to be processed according to the method described below. The user inputs that cause the system to perform the method described below may be based on one or more user preferences, one or more image characteristics, and/or the like.

At block 2206, the system optionally adds the displayed image/frame that has been indicated by the user to a montage, as described above. Further, the montage may be added to the series/exam of the image/frame, or to another series/exam. In some implementations, the user may indicate image characteristics to be applied to the image/frame added to the montage, may indicate a location of the image/frame in the montage, may indicate annotations to the image/frame, and/or the like.

At block 2208, the system may create a copy of the displayed image/frame that has been indicated by the user. In various implementations, the user may indicate image characteristics to be applied to a copy of the image/frame, may indicate annotations to the image/frame, and/or the like. In some implementations, an actual copy of the image/frame is not created, but rather data necessary to identify the indicated image/frame and update the indicated image/frame (e.g., with annotations, changed image characteristics, etc.) is created and stored by the system in the series/exam. This implementation may advantageously save data stores requirements and/or bandwidth requirements as a copy of a high resolution image may not need to be stored/transferred. Rather, system may generate the "copy" of the image/frame based on the data and the original copy of the image/frame when display is requested by the user. In some implementations the "copy" of the image/frame may be generated preemptively, prior to the user requesting to display the image/frame.

At block 2210, the system may insert the copy of the displayed image/frame into the series/exam of the image/frame, or another series/exam. As mentioned above, in some implementations only data necessary to create the image/frame is generated and inserted into the series/exam.

At block 2212, the images/frames, including the inserted copies, are sorted according to any other methods described here. For example, the inserted copy of the image/frame may be added to the series/exam at a location following an original copy of the image/exam, as described above. In other implementations, the images/frames may be sorted in other ways.

The user may view the images/frames of the series/exam according to any of the methods described herein. In some implementations, the indicated image/frame may be automatically processed in any other way by the system, including by one or more CAP, as described herein.

Advantageously, according to certain embodiments, the original copies of images/frames may be preserved while updated copies of the images/frames (e.g., with annotations, with changed image characteristics, etc.) may be added to series/exams automatically. Advantageously, according to certain embodiments, frames may be extracted from multi-images and automatically added to a series/exam for further review by a user. Advantageously, according to certain embodiments, images/frames of a series/exam may be sorted for efficient review by a user. Advantageously, according to certain embodiments, the system may accordingly enable a user to efficiently review and compare images/frames of a series/exam, including copies (which may be updated/changed) of images/frames indicated by the user.

IX. Example Computing Systems

Referring again to FIG. 1, various configurations of the computing system 150 and network environment 100 may be used to implement and/or accomplish the systems and methods disclosed herein. For example, the computing system 150 may be configured to display and/or enable a user to view and/or interact with various types of data including two-dimensional images, three-dimensional volumes, and/or other types of information, as described above.

As described above, the computing system may take various forms. In one embodiment, the computing system 150 may be an information display computing device and/or system, a server, a computer workstation, a desktop computer, a Picture Archiving and Communication System (PACS) workstation, a laptop computer, a mobile computer, a smartphone, a tablet computer, a wearable computer (for example, a head-mounted computer and/or a computer in communication with a head-mounted display), a smartwatch, a mobile computer, a cell phone, a personal digital assistant, a gaming system, a kiosk, an audio player, and/or any other device that utilizes a graphical user interface, such as office equipment, automobiles, airplane cockpits, household appliances, automated teller machines, self-service checkouts at stores, information and other kiosks, ticketing kiosks, vending machines, industrial equipment, and/or a television, for example. In an embodiment the computing system 150 comprises one or more computing devices in communication with one another.

The computing system 150 may include various components including, for example, one or more processors 152, memory and/or data storage 153 (including one or more software modules 151 and/or a rules engine 163 (which may itself comprise a software module)), an operating system 154, a display 155, one or more input devices 156, one or more interfaces 157, an audio input/output 158, and/or one or more sensors 161 (including, for example, zero or more motion sensors 159, zero or more orientation sensors 160, and/or zero or more location sensors 162). Each of the components of the computing system 150 may be connected and/or in communication with each other using, for example, a standard based bus system. In different embodiments, the standard based bus system could be Peripheral Component Interconnect ("PCI"), PCI Express, Accelerated Graphics Port ("AGP"), Micro channel, Small Computer System Interface ("SCSI"), Industrial Standard Architecture ("ISA") and Extended ISA ("EISA") architectures, for example. In addition, the functionality provided for in the components and modules of computing system 150 (as described above and below) may be combined into fewer components and modules or further separated into additional components and modules.

In various embodiments the software modules 151 may provide functionality as described above with reference to the various figures. For example, modules 151 of the computing system 150 may include user input modules, image display modules, motion detection/determination modules, orientation detection/determination modules, position detection/determination modules, location detection/determination modules, patient information display modules, rules engine modules (for example, rules engine 163), user interface modules, and/or the like. For example, each of the motion, orientation, position, and/or location detection/determination modules may determine user inputs and/or gestures such that the user may interact with medical images, as described above. Further, the image display modules and/or the user interface modules may display user interfaces, images, and/or other data on the display 155 in response to user inputs (as described in reference to various embodiments of the present disclosure). Further, the image display modules and/or the user interface modules may be configured and/or designed to generate user interface data useable for rendering the interactive user interfaces described herein, such as a web application and/or a dynamic web page displayed by a computing device. In various embodiments the user interface data may be used by the computing system 150, and/or communicated to any other computing device, such that the example user interfaces are displayed to a user. For example, the user interface data may be executed by a browser (and/or other software program) accessing a web service and configured to render the user interfaces based on the user interface data.

The rules engine 163 may operate in conjunction with the other modules to perform various functionality of the data navigation systems described above. For example, the rules engine 163 may determine, based on one or more rules of the user preferences and rules database 124, that a user input (e.g., a particular type of movement or input) is to be translated into a particular adjustment of a displayed image and/or other data. Further, the rules engine 163 may determine, based on one or more rules of the user preferences and rules database 124, certain types of images are to be sorted (and/or selected for comparison) based on certain attributes of those images, automatic selection of images for comparison with a user selected image, preferences for registration of sorted and/or comparison images, selection of CDS data, and/or the like. Such determinations may be based on, for example, a type of data displayed and/or an identify or characteristic associated with a user. As described above, rules of the user preferences and rules database 124 that may be executed by the rules engine 163 may include sorting rules, matching rules, and/or any other types of rules.

As described below, the software modules 151 may include various software instructions, code, logic instructions, and/or the like that may be executed by the one or more processors 152 to accomplish the functionality described above. In other embodiments, software modules 151 may reside on another computing device and/or system, such as a web server or other server (for example, server 120) or other server, and a user may directly interact with a second computing device and/or system that is connected to the other computing device and/or system via a computer network.

The computing system 150 may run an off-the-shelf operating system 154 such as a Windows, Linux, MacOS, Android, or iOS, or mobile versions of such operating systems. The computing system 150 may also run a more specialized operating system which may be designed for the specific tasks performed by the computing system 150, or any other available operating system.

The computing system 150 may include one or more computer processors 152, for example, hardware computer processors. The computer processors 152 may include central processing units (CPUs), and may further include dedicated processors such as graphics processor chips, or other specialized processors. The processors may be used to execute computer instructions based on the software modules 151 to cause the computing system 150 to perform operations as specified by the modules 151. The software modules 151 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. For example, modules may include software code written in a programming language, such as, for example, Java, Objective-C, Swift, JavaScript, ActionScript, Visual Basic, HTML, Lua, C, C++, or C#. While "modules" are generally discussed herein with reference to software, any modules may alternatively be represented in hardware or firmware. In various embodiments, the modules described herein refer to logical modules that may be combined with other modules or divided into sub-modules despite their physical organization or storage.

The computing system 150 may also include memory 153. The memory 153 may include volatile data storage such as RAM or SDRAM. The memory may also include more permanent forms of storage such as a hard disk drive, a flash disk, flash memory, a solid state drive, or some other type of non-volatile storage, as described below.

The computing system 150 may also include or be interfaced to one or more display devices that provide information to the users. Display devices 155 may include a video display, such as one or more high-resolution computer monitors, or a display device integrated into or attached to a laptop computer, handheld computer, smartphone, smartwatch, wearable computer, computer tablet device, or medical scanner. In other embodiments, the display device 155 may include an LCD, OLED, or other thin screen display surface, a monitor, television, projector, a display integrated into wearable glasses, or any other device that visually depicts user interfaces and data to viewers. As described above, images and other information may be displayed to the user via the display devices 155 such that the user may efficiently view and interact with such images and information.

The computing system 150 may also include or be interfaced to one or more input devices 156 which receive input from users, such as a keyboard, trackball, mouse, 3D mouse, dial and/or knob (for example, a smartwatch crown), drawing tablet, joystick, game controller, touch sensitive surface (for example, capacitive or resistive touch screen), touchpad, accelerometer, video camera and/or microphone.

The computing system 150 may also include one or more interfaces 157 which allow information exchange between the computing system 150 and other computers and input/output devices using systems such as Ethernet, Wi-Fi, Bluetooth, as well as other wired and wireless data communications techniques.

The computing system 150 may include the audio input/output 158 for receiving, for example, audio commands or other input from the user. The audio system may also provide audio output to provide audio information to a user, for example via a speaker or headset. As described above, various sensors of the computing system 150 may include, for example, gyroscopes, accelerometers, cameras, Global Positioning System (GPS) transceivers and devices, near field communication (NFC) technology devices, Radio Frequency Identification (RFID) device, systems and devices utilizing WiFi, systems and devices utilizing Bluetooth such as iBeacons, and/or the like. The various sensors may provide input/data to the computing system 150 related to the location, position, orientation, and/or motion of a user, a user's appendage (such as an arm and/or hand), and/or another input device operated by the user. Such information may be processed by, for example, one or more software modules 151 (such as the rules engine 163) as described above, such that displayed image data (or other types of data) may be updated. Additionally, as described above, the system may also include, in some embodiments, external sensors 125 that may also provide data related to user inputs. External sensors 125 may include any of the sensors described herein, and may provide functionality similar to that described herein with reference to the various sensors. In various embodiments, the functionality provided by image storage 122, server 120, and/or CDS server 171, may reside within computing system 150.

The computing system 150 may communicate and/or interface with other systems and/or devices. In one or more embodiments, the computing system 150 may be connected to the computer network 190. The computer network 190 may take various forms. For example, the computer network 190 may be a wired network or a wireless network, or it may be some combination of both. The computer network 190 may be a single computer network, or it may be a combination or collection of different networks and network protocols. Additionally, the computer network 190 may include one or more local area networks (LAN), wide area networks (WAN), personal area networks (PAN), cellular or data networks, and/or the Internet.

Various devices and subsystems may be connected to the network 190. As shown in FIG. 1, for example, the computing system 150 may be in communication with the image storage 122, the server 120, the external sensor(s) 125, the imaging devices 170, and/or the CDS server 171. Image storage 122 may be a database, data store, and/or other electronic or computer-readable medium storage device configured to store, for example, medical images and/or three-dimensional imaging data. Such medical images and/or three-dimensional imaging data may be processed, for example, by the server 120 and/or the computing system 150. Further, the various components of the network environment 100 may be in communication with various other devices that may, for example, capture and provide images and/or other data to the computing system 150. For example, imaging devices 170 may include one or more medical scanners may be connected, such as MRI scanners. The MRI scanner may be used to acquire MRI images from patients, and may share the acquired images with other devices on the network 190. The imaging devices 170 may also include one or more CT scanners and/or X-Ray scanners. The CT scanners and/or X-Ray scanners may also be used to acquire images and, like the MRI scanner, may then store those images and/or share those images with other devices via the network 190. Any other scanner or device capable of inputting or generating information that may be presented to the user as images, graphics, text or sound may be connected to the network 190, including, for example, computing systems used in the fields of ultrasound, angiography, nuclear medicine, radiography, endoscopy, pathology, dermatology, and the like.

Also connected to the network 190 may be a Picture Archiving and Communications System (PACS) and/or PACS workstation. The PACS System may be used for the storage, retrieval, distribution and presentation of images (such as those created and/or generated by the MRI scanner and/or CT Scanner). The medical images may be stored in an independent format, an open source format, or some other proprietary format. A common format for image storage in the PACS system is the Digital Imaging and Communications in Medicine (DICOM) format. In various embodiments, the stored images may be transmitted digitally via the PACS system, often reducing or eliminating the need for manually creating, filing, or transporting film jackets.

The network 190 may also be connected to a Radiology Information System (RIS). In an embodiment, the radiology information system may be a computerized system that is used by radiology departments to store, manipulate and distribute patient radiological information.

Also attached to the network 190 may be an Electronic Medical Record (EMR) system. The EMR system may be configured to store and make accessible to a plurality of medical practitioners computerized medical records. Also attached to the network 190 may be a Laboratory Information System. In an embodiment, the Laboratory Information System may be a software system which stores information created or generated by clinical laboratories. Also attached to the network 190 may be a Digital Pathology System that may be used to digitally manage and store information related to medical pathology.

Also attached to the network 190 may be one or more Computer Aided Diagnosis Systems (CAD) systems that are generally used to perform Computer-Aided Processing (CAP) such as, for example, CAD processes. In one embodiment, the CAD systems functionality may reside in a computing device and/or system separate from computing system 150 while in another embodiment the CAD systems functionality may reside within computing system 150.

Also attached to the network 190 may be one or more Processing Systems that may be used to perform computerized advanced processing such as, for example, computations on imaging information to create new views of the information, for example, volume rendering and/or other types of processing, for example image enhancement, volume quantification, blood-flow quantification, and the like. In one embodiment, such processing functionality may reside in a computing device and/or system separate from computing system 150 while in another embodiment the processing functionality may reside within computing system 150.

In other embodiments, other computing devices and/or systems that store, provide, acquire, and/or otherwise manipulate medical data may also be coupled to the network 190 and may be in communication with one or more of the devices illustrated in FIG. 1, such as with the computing system 150.

Depending on the embodiment, other devices discussed herein may include some or all of the same components discussed above with reference to the computing system 150 and may perform some or all of the functionality discussed herein.

As mentioned above, various of the image storage 122, the server 120, the user preferences and rules database 124, the external sensor(s) 125, the imaging devices 170, the CDS server 171, and/or other components described above may or may not be considered a part of the computing system 150. For example, in some embodiments one or more of these components may be implemented as part of the computing system 150, may be in direct communication with the computing system 150, and/or may be in indirect communication (e.g., over network 190) with the computing system 150.

X. Additional Embodiments

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure.

For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid state drive) either before or after execution by the computer processor.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. For example, any of the processes, methods, algorithms, elements, blocks, applications, or other functionality (or portions of functionality) described in the preceding sections may be embodied in, and/or fully or partially automated via, electronic hardware such application-specific processors (e.g., application-specific integrated circuits (ASICs)), programmable processors (e.g., field programmable gate arrays (FPGAs)), application-specific circuitry, and/or the like (any of which may also combine custom hard-wired logic, logic circuits, ASICs, FPGAs, etc. with custom programming/execution of software instructions to accomplish the techniques).

Any of the above-mentioned processors, and/or devices incorporating any of the above-mentioned processors, may be referred to herein as, for example, "computers," "computer devices," "computing devices," "hardware computing devices," "hardware processors," "processing units," and/or the like. Computing devices of the above-embodiments may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In other embodiments, the computing devices may be controlled by a proprietary operating system. Conventional operating systems control and schedule computer processes for execution, perform memory management, provide file system, networking, I/O services, and provide a user interface functionality, such as a graphical user interface ("GUI"), among other things.

As described above, in various embodiments certain functionality may be accessible by a user through a web-based viewer (such as a web browser), or other suitable software program. In such implementations, the user interface may be generated by a server computing system and transmitted to a web browser of the user (e.g., running on the user's computing system). Alternatively, data (e.g., user interface data) necessary for generating the user interface may be provided by the server computing system to the browser, where the user interface may be generated (e.g., the user interface data may be executed by a browser accessing a web service and may be configured to render the user interfaces based on the user interface data). The user may then interact with the user interface through the web-browser. User interfaces of certain implementations may be accessible through one or more dedicated software applications. In certain embodiments, one or more of the computing devices and/or systems of the disclosure may include mobile computing devices, and user interfaces may be accessible through such mobile computing devices (for example, smartphones and/or tablets).

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A database computing system for processing digital medical images, the computing system comprising:
   an electronic display;
   an input device; and
   one or more computer processors in communication with the electronic display, the input device, and a non-transitory computer-readable medium storing software modules including software instructions that are executable by the one or more computer processors in order to cause the one or more computer processors to:
   access an image series comprising a plurality of images, wherein at least some of the plurality of images comprise multi-frame images;
   display a first image of the plurality of images at a location on the electronic display;
   in response to a first input, received via the input device, display a frame of a second image of the plurality of images at the location on the electronic display, wherein the frame of the second image replaces the first image on the electronic display, wherein the second image comprises a multi-frame image;
   in response to a second input, received via the input device:
   create a copy of the frame of the second image directly in response to the second input;
   add the copy of the frame of the second image to the image series as a new image directly in response to the second input; and
   sort the image series such that the new image is located adjacent to the second image in the image series directly in response to the second input.

2. The computing system of claim 1, wherein the one or more computer processors are configured to execute the software instructions in order to further cause the computing system to:
   directly in response to the second input, add the copy of the frame of the second image to a montage; and
   add the montage to the image series.

3. The computing system of claim 1, wherein the one or more computer processors are configured to execute the software instructions in order to further cause the computing system to:
   directly in response to the second input, generate data necessary to create a montage including the frame of the second image and any changes to the frame of the second image indicated by the second input; and
   add an indication of the montage to the image series.

4. The computing system of claim 1, wherein the second input indicates adding an annotation to the frame of the second image.

5. The computing system of claim 1, wherein the second input indicates the frame of the second image is a key image.

6. The computing system of claim 1, wherein the second input indicates a change of an image characteristic of the frame of the second image.

7. The computing system of claim 1, wherein the one or more computer processors are configured to execute the software instructions in order to further cause the computing system to:
 retrieve the image series from an image store to access the image series; and
 directly in response to the second input, store the image series including the copy of the frame of the second image in the image store.

8. The computing system of claim 1, wherein the one or more computer processors are configured to execute the software instructions in order to further cause the computing system to:
 retrieve the image series from an image store to access the image series; and
 generate update data for the copy of the frame of the second image directly in response to the second input; and
 store the image series including identification data for the frame of the second image and the update data in the image store directly in response to the second input.

9. A database computing system for processing digital images, the computing system comprising:
 an electronic display;
 an input device; and
 one or more computer processors in communication with the electronic display, the input device, and a non-transitory computer-readable medium storing software modules including software instructions that are executable by the one or more computer processors in order to cause the one or more computer processors to:
  access an image series comprising a plurality of images, wherein at least some of the plurality of images comprise multi-frame images;
  display a first image of the plurality of images at a location on the electronic display;
  in response to a first input, received via the input device, display a frame of a second image of the plurality of images at the location on the electronic display, wherein the frame of the second image replaces the first image on the electronic display, wherein the second image comprises a multi-frame image;
  in response to a second input, received via the input device:
   create data including an indication of the frame of the second image and update information associated with the frame of the second image directly in response to the second input;
   add the data to the image series as an indication of an additional image directly in response to the second input; and
   sort the image series such that the additional image is located adjacent to the second image in the image series directly in response to the second input.

10. The computing system of claim 9, wherein the information associated with the second input includes at least one of:
 an indication that the frame of the second image is a key image, an addition of an annotation to the frame of the second image, or an adjustment to an image characteristic of the frame of the second image.

11. The computing system of claim 9, wherein the one or more computer processors are configured to execute the software instructions in order to further cause the computing system to:
 in response to a third input, received via the input device, indicating that the additional image is to be displayed:
  generate the additional image based on the data including the indication of the frame of the second image and the information associated with the second input; and
  display the additional image in the location on the electronic display.

12. The computing system of claim 9, wherein the one or more computer processors are configured to execute the software instructions in order to further cause the computing system to:
 directly in response to the second input, add a copy of the frame of the second image to a montage; and add the montage to the image series.

13. The computing system of claim 9, wherein the one or more computer processors are configured to execute the software instructions in order to further cause the computing system to:
 directly in response to the second input, generate data necessary to create a montage including the frame of the second image and any changes to the frame of the second image indicated by the second input; and add an indication of the montage to the image series.

14. The database computing system of claim 9, wherein the one or more computer processors are configured to execute the software instructions in order to further cause the computing system to:
 retrieve the image series from an image store to access the image series; and
 directly in response to the first input, store the image series including the data including the indication of the frame of the second image and the update information in the image store.

15. A database computing system for processing digital images, the computing system comprising:
 an electronic display;
 an input device; and
 one or more computer processors in communication with the electronic display, the input device, and a non-transitory computer-readable medium storing software modules including software instructions that are executable by the one or more computer processors in order to cause the one or more computer processors to:
  access an image series comprising a plurality of images, wherein at least some of the plurality of images comprise multi-frame images;
  display a first image of the plurality of images at a location on the electronic display;
  in response to a first input, received via the input device:
   create a copy of the first image directly in response to the first input;
   add the copy of the first image to the image series as a new image directly in response to the first input; and
   sort the image series, including the new image, based one or more user preferences or sorting rules directly in response to the first input.

16. The computing system of claim 15, wherein sorting the image series comprises:
 accessing a first one or more sorting rules indicating a first attribute and a second attribute; and
 sorting the image series by at least: sorting images of the image series based on the first attribute; and further images of the image series based on the second attribute such that the images of the image series are sorted based on both the first and second attributes.

17. The computing system of claim 15, wherein the one or more computer processors are configured to execute the software instructions in order to further cause the computing system to:
   directly in response to the first input, add the copy of the first image to a montage; and
   add the montage to the image series directly in response to the first input.

18. The computing system of claim 15, wherein the one or more computer processors are configured to execute the software instructions in order to further cause the computing system to:
   directly in response to the first input, generate data necessary to create a montage including the first image and any changes to the first image indicated by the input; and
   add an indication of the montage to the image series directly in response to the first input.

19. The computing system of claim 15, wherein the second input indicates adding an annotation to the first image.

20. The computing system of claim 15, wherein the second input indicates the first image is a key image.

21. The computing system of claim 15, wherein the second input indicates a change of an image characteristic of the first image.

22. The computing system of claim 15, wherein the one or more computer processors are configured to execute the software instructions in order to further cause the computing system to:
   retrieve the image series from an image store to access the image series; and
   directly in response to the first input, store the image series including the copy of the first image in the image store.

23. The computing system of claim 15, wherein the one or more computer processors are configured to execute the software instructions in order to further cause the computing system to:
   retrieve the image series from an image store to access the image series; and
   directly in response to the first input:
      generate update data for the first image; and
      store the image series including identification data for the first image and the update data in the image store.

* * * * *